(12) United States Patent
Dodge et al.

(10) Patent No.: US 7,217,734 B2
(45) Date of Patent: May 15, 2007

(54) SUBSTITUTED BENZOPYRANS AS SELECTIVE ESTROGEN RECEPTOR-BETA AGONISTS

(75) Inventors: Jeffrey Alan Dodge, Indianapolis, IN (US); Venkatesh Krishnan, Fishers, IN (US); Charles Willis Lugar, III, McCordsville, IN (US); Blake Lee Neubauer, Carmel, IN (US); Bryan Hurst Norman, Indianapolis, IN (US); Lance Allen Pfeifer, Indianapolis, IN (US); Timothy Ivo Richardson, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/493,092

(22) PCT Filed: Nov. 7, 2002

(86) PCT No.: PCT/US02/33622

§ 371 (c)(1),
(2), (4) Date: Apr. 20, 2004

(87) PCT Pub. No.: WO03/044006

PCT Pub. Date: May 30, 2003

(65) Prior Publication Data

US 2004/0249167 A1    Dec. 9, 2004

Related U.S. Application Data

(60) Provisional application No. 60/363,622, filed on Mar. 11, 2002, provisional application No. 60/332,766, filed on Nov. 19, 2001.

(51) Int. Cl.
*A61K 31/35* (2006.01)
(52) U.S. Cl. .................. 514/454; 549/385; 549/390
(58) Field of Classification Search ................ 549/390, 549/385; 514/454
See application file for complete search history.

(56) References Cited

U.S. PATENT DOCUMENTS

| | | |
|---|---|---|
| 3,901,926 A | 8/1975 | Winn et al. |
| 6,436,923 B1 | 8/2002 | Bhagwat et al. |
| 6,518,301 B1 | 2/2003 | Barlaam et al. |
| 6,593,322 B1 | 7/2003 | Bhagwat et al. |
| 6,630,508 B1 | 10/2003 | Dodge et al. |
| 6,794,403 B2 | 9/2004 | Malamas et al. |

FOREIGN PATENT DOCUMENTS

| | | |
|---|---|---|
| GB | 2 361 642 A | 10/2000 |
| WO | WO 97/09348 | 9/1996 |
| WO | WO 99 02512 A | 1/1999 |
| WO | WO 01/49673 A2 | 7/2001 |
| WO | WO 01 64665 A | 9/2001 |
| WO | WO 01/72713 A1 | 10/2001 |
| WO | WO 03/051805 A2 | 6/2003 |

OTHER PUBLICATIONS

Shrestha KS et al, 'Facil synthesis of the fused 6-6-5ring system containing chroman ring form 2-(1-1hydroxy-5-alkenyl)phenyl derivatives via intramolecular inverse-electron-demand diels-alder reaction' CA 130:196557 (1999).*
Anderson WK et al , 'Snythesis of 6,9-bisnormethyl-8-methoxy-12, 13-epoxy-6,8, 10-trichothecatriene' CA 86:121542 (1977).*
Oude-Alink, BAM et al, 'Photolysis of 2-keto-2,3-dihydrobenzofurans, o-hydroxystyrenes and 1-(o-hydroxyphenyl)-1,5-hexadienes' CA 79:17767 (1973).*
Weihua et al, Estrogen receptor beta in the prostate, Molecular and Cellular Endocrinology 193 (2002) 1-5.*
Balfe et al, Estrogen receptor beta and breast cancer, PMID:1552549.*
Speirs, Oestrogen receptor in breast cancer: good, bad or still too early to tell?, J. Pathol 2002, 197:143-147.*
K SH. Shrestha, et al.: "*Facile Synthesis of the Fused 6,6,5 Ring System Containing Chroman Ring from 2-(1-Hydroxy-5-alkenyl)phenol Derivatives via Intromolecular Inverse-Election-Demand Diels-Alder Reaction*": Bull. Chem. Soc. Japan, vol. 72, No. 1, (1999), pp. 73-83.
K.W. Anderson, et al.: "Synthesis of 6,9-bisnormethyl-8-methoxy-12, 13-epoxy-6,8, 10-trichothecatriene": Journal of Organic Chemistry, vol. 42, No. 6, (1977), pp. 1045-1050.
B.A. M. Oude-Alink, et al.: "*Photolysis of 2-keto-2, 3-dihydrobenzofurans, o-hydroxystyrenes and 1-o-hydroxyphenyl)-1, 5-hexadienes*": Journal of Organic Chemistry, vol. 38, No. 11, (1973), pp. 1993-2001.
Welhua, Zhang, et al.: "*A Role for Estrogen Receptor β in the Regulation of Growth of the Ventral Prostate*"; PNAS; vol. 98, No. 11, (2001), pp. 6330-6335.
Mortensen, Deborah S., et al.: "*Synthesis and Biological Evaluation of a Novel Series of Furans: Ligands Selectie for Estrogen Receptor α*"; Journal of Medicinal Chemistry; A-K, (May 11, 2001), PAGE EST: 10:8.
Meyers, Marvin J., et al.: "*Estrogen Receptor-β Potency-Selective Ligands: Structure-Activity Relationship Studies of Diarylpropionitriles and Their Acetylene and Polar Analogues*"; Journal of Medicinal Chemistry, A-V, (Jun. 6, 2001), PAGE EST:21:3.

(Continued)

*Primary Examiner*—Amelia A. Owens
(74) *Attorney, Agent, or Firm*—John C. Demeter

(57) ABSTRACT

The present invention relates to substituted benzopyran derivatives, stereoisomers, and pharmaceutical acceptable salts thereof and processes for the preparation of the same. The compounds of the present invention are useful as Estrogen Receptor β agonists. Such agonists are useful for the treating Estrogen Receptor β mediated diseases such as prostate cancer.

52 Claims, No Drawings

OTHER PUBLICATIONS

Kuiper, et al., "Cloning of a novel estrogen receptor expressed in rat prostate of ovary," *Proc. Natl. Acad. Sci. USA*, vol. 93, pp. 5925-5930 (1996).

Tremblay, et al., "Cloning, Chromosomal Localization, and Functional Analysis of the Murine Estrogen Receptor β," *Molecular Endocrinology*, vol. 11, No. 3, pp. 353-365 (1997).

Weihua, et al., "Estrogen receptor beta in the prostate," *Molecular and Cellular Endocrinology*, vol. 193, pp. 1-5 (2002).

Balfe, et al., "Estrogen receptor β and breast cancer," *EJSO*, vol. 30, pp. 1043-1050 (2004).

Speirs, "oestrogen receptor β in breast cancer: good, bad or still too early to tell?" *Journal of Pathology*, vol. 197, pp. 143-147 (2002).

Muchmore, "Raloxifene: A Selective Estrogen Receptor Modulator (SERM) with Multiple Target System Effects," *The Oncologist*, vol. 5, pp. 388-392 (2000).

Katzenellenbogen, et al., "Editorial: A New Actor in the Estrogen Receptor Drama—Enter ER-β," *Endocrinology*, vol. 138. No. 3, pp. 861-862 (1997).

Mosselmann, et al., "ERβ: identification and characterization of a novel human estrogen receptor," *FEBS Letters*, vol. 392, pp. 49-53 (1996).

Paech, et al., "Differential Ligand Activation of Estrogen Receptors Erα and ERβ at AP1 Sites," *Science*, vol. 277, pp. 1508-1510 (1997).

Sun, et al., "Novel Ligands the Function as Selective Estrogens or Antiestrogens for Estrogen Receptor-α or Estrogen Receptor-β*," *Endocrinology*, vol. 140, No. 2, pp. 800-804 (1999).

Couse, et al., "Tissue Distribution and Quantitative Analysis of Estrogen Receptor-α (ERα) and Estrogen Receptor-β (ERβ) Messenger Ribonucleic Acid in the Wild-Type and ERα-Knockout Mouse," *Endocrinology*, vol. 138, No. 11, pp. 4613-4621 (1997).

Kuiper, et al., "Comparison of the Ligand Binding specificity and Transcript Tissue Distribution of Estrogen Receptors α and β," *Endocrinology*, vol. 138, No. 3, pp. 863-870 (1997).

Brandenberger, et al., "Estrogen Receptor Alpha (ER-α) and Beta (ER-β) mRNAs in Normal Ovary, Ovarian Serous Cystadenocarcinoma and Ovarian Cancer Cell Lines: Down-Regulation of ER-β in Neoplastic Tissues," *Journal of Clinical Endocrinology and Metabolism*, vol. 83, No. 3. pp. 1025-1028 (1998).

Enmark, et al., "Human Estrogen Receptor β-Gene Structure, Chromosomal Localization, and Expression Pattern," *Journal of Clinical Endocrinology and Metabolism*, vol. 82, No. 12, pp. 4258-4265 (1997).

Laflamme, et al., "Expression and Neuropeptidergic Characterization of Estrogen Receptors (ERα and ERβ) throughout the Rat Brain: Anatomical Evidence of Distinct Roles of Each Subtype," *J. Neurobiol.* vol. 36, No. 3, pp. 357-578 (1998).

Sar, et al., "Differential Expression of Estrogen Receptor-β and Estrogen Receptor-α in the Rat Ovary," *Endocrinology*, vol. 140, No. 2, pp. 963-971 (1999).

Shughrue, et al., "The Distribution of Estrogen Receptor-β nRNA in Forebrain Regions of the Estrogen Receptor-a Knockout Mouse," *Endocrinology*, vol. 138, No. 12, pp. 5649-5652 (1997).

Shughrue, et al., "Comparative Distribution of Estrogen Receptor-α and -β nRNA in the Rat Central Nervous System," *The Journal of Comparative Neurology*, vol. 388, No. 4, pp. 507-525 (1997).

Chang, et al., "Estrogen Receptor-β: Implications for the Prostate Gland," *The Prostate*, vol. 40, pp. 115-124 (1999).

Korach, "Insights from the Study of Animals Lacking Functional Estrogen Receptor," *Science*, vol. 266, pp. 1524-1527 (1994).

Krege, et al., "Generation and reproductive phenotypes of mice lacking estrogen receptor β," *Proc. Natl. Acad. Sci USA*, vol. 95, pp. 15677-15682 (1998).

Cooke, et al., "Mechanism of Estrogen Action: Lessons from the Estrogen Receptor-α Knockout Mouse," *Biology of Reproduction*, vol. 59, pp. 470-475 (1998).

Das, et al., "Estrogenic responses in estrogen receptor-α deficient mice reveal a distinct estrogen signaling pathway," *Proc. Natl. Acad. Sci. USA*, vol. 94, pp. 12786-12791 (1997).

Ogawa, et al., "Behavioral effects of estrogen receptor gene disruption in male mice," *Proc. Natl. Acad. Sci, USA*, vol. 94, pp. 1476-1481 (1997).

Rissman et al., "Estrogen Receptors are Essential for Female Sexual Receptivity," *Endocrinology*, vol. 138, No. 1, pp. 507-510 (1997).

Rissman, et al., "Estrogen Receptor Function as Revealed by Knockout Studies: Neuroendocrine and Behavioral Aspects," *Hormones and Behavior.*, vol. 31, pp. 232-243 (1997).

Sughrue, et al., "Responses in the brain of estrogen receptor α-disrupted mice," *Proc. Natl. Acad. Sci. USA*, vol. 94, pp. 11008-11012 (1997).

Iafrati, et al., "Estrogen inhibits the vascular injury response in estrogen receptor α-deficient mice," *Nature Medicine*, vol. 3, No. 5, pp. 545-548 (1997).

Couse, et al., "Postnatal Sex Reversal of the Ovaries in Mice Lacking Estrogen Receptors α and β," *Science*, vol. 286, pp. 2328-2331 (1999).

Barkhem, et al., "Differential Response of Estrogen Receptor α and Estrogen Receptor β to Partial Estrogen Agonists/Antagonists," *Molecular Pharmacology*, vol. 54, pp. 105-112 (1998).

Farhat, et al., "The vascular protective effects of estrogen," *The FASEB Journal*, vol. 10, pp. 615-624 (1996).

Gustafsson, "Therapeutic potential of selective estrogen receptor modulators," *Chem. Biol*, vol. 2, pp. 508-511 (1998).

Tremblay, et al., "EM-800, a Novel Antiestrogen, Acts as a Pure Antagonist of the Transcriptional Functions of Estrogen Receptors α and β," *Endocrinology*, vol. 139, No. 1, pp. 111-118 (1998).

Turner, et al., "Differential Responses of Estrogen Target Tissues in Rats Including Bone to Clomiphene, Enclomiphene, and Zuclomiphene," *Endocrinology*, vol. 139, No. 9, pp. 3712-3720 (1998).

Clinton, et al., "Estrogen action in human ovarian cancer," *Critical Reviews in Oncology/Hematology*, vol. 25, pp. 1-9 (1997).

Hata, et al., "Role of Estrogen and Estrogen-Related Growth Factor in the Mechanism of Hormone Dependency of Endometrial Carcinoma Cells," *Oncology*, vol. 55, Suppl. 1, pp. 35-44 (1998).

Rohlff, et al.., "Prostate Cancer Cell Growth Inhibition by Tamoxifen Is Associated With Inhibition of Protein Kinase C and Induction of $p21^{waft/cip1}$," *The Prostate*, vol. 37, pp. 51-59 (1998).

Simpson, et al., "Estrogen Regulation of Transforming Growth Factor-a in Ovarian Cancer," *J. Steroid Biochem. Molec, Biol.*, vol. 64, No. 3-4, pp. 137-145 (1998).

Yamashita, et al., "Endocrine Therapy in Pancreatic Carcinoma," *Oncology*, vol. 55, Suppl. 1, pp. 17-22 (1998).

Nilsson, et al., "ERβ: a Novel Estrogen Receptor Offers the Potential for New Drug Development," *TEM*, vol. 9, No. 10, pp. 387-395 (1998).

Risbridger, et al., "Evidence That Epithelial and Mesenchymal Estrogen Receptor-α Mediates Effects of Estrogen on Prostatic Epithelium" *Developmental Biology*, vol. 229, pp. 432-442 (2001).

Weihua, et al., "A role of estrogen receptor β in the regulation of growth of the ventral prostate," *PNAS*, vol. 98, No. 11, pp. 6330-6335 (2001).

Maruyama, et al., "Expression of Estrogen Receptor α and β mRNAs in Prostate Cancers Treated with Leuprorelin Acetate," *European Urology*, vol. 38, pp. 635-639 (2000).

Steiner, et al., "Selective Estrogen Receptor Modulators for the Chemoprevention of Prostate Cancer," *Urology*, vol. 57, Suppl. 4A, pp. 68-72 (2001).

Leav, et al., "Comparative Studies of the Estrogen Receptors β and α and the Androgen Receptor in Normal Human Prostate Glands, Dysplasia, and in Primary and Metastatic Carcinoma, " *American Journal of Pathology*, vol. 159, No. 1, pp. 79-92 (2001).

Meyers, et al., "Estrogen Receptor-b Potency-Selective Ligands: Structure-Activity Relationship Studies of Diarylpropionitriles and Their Acetylene and Polar Analogues," *J. Med. Chem*, vol. 44, pp. 4230-4251 (2001).

\* cited by examiner

SUBSTITUTED BENZOPYRANS AS SELECTIVE ESTROGEN RECEPTOR-BETA AGONISTS

This application claims the benefit under 35 U.S.C. §120 of International Application No. PCT/US02/33622, filed Nov. 7, 2002, which claims the benefit under 35 U.S.C. §119(e) of U.S. Ser. No. 60/332,766, filed Nov. 19, 2001 and U.S. Ser. No. 60/363,622, filed Mar. 11, 2002.

BACKGROUND OF THE INVENTION

The present invention relates to novel cycloalkyl-benzopyrans and derivatives thereof, compositions containing those compounds, their use as selective estrogen receptor-beta agonists, and their use in the treatment of estrogen receptor-beta mediated diseases such as prostate cancer, benign prostatic hyperplasia, testicular cancer, ovarian cancer, lung cancer, cardiovascular diseases, neurodegenerative disorders, urinary incontinence, central nervous system (CNS) disorders, gastrointestinal (GI) tract disorders, and osteoporosis.

Estrogens play important roles in the development and homeostasis of the reproductive, central nervous, skeletal, and cardiovascular systems of both males and females. The estrogen receptor (ER) is currently the only member of the steroid subfamily of nuclear receptors that has different subtypes. Recently, a new ER isoform, ER-beta (also known as ER-beta1) was cloned from a rat prostatic cDNA library and is present in murine and human prostates. Consequently, the previous ER is now designated as ER-alpha. ER-alpha and ER-beta share high amino acid homology, have similar 17-β Estradiol (E2) binding affinities, and can hetero- or homodimerize to form a signaling complex; Kuiper G G, et al., Endocrinol. 138: 863–70 (1997); Kuiper G G et al., Proc. Natl. Acad. Sci. USA 93: 5925–30 (1996). Although E2 activates both ER-alpha and ER-beta, ER-alpha stimulates transcription and cellular proliferation, while ER-beta suppresses ER-alpha activation. Interestingly, 3-beta, 17-beta-androstanediol and 5-alpha-androstane have been proposed to be endogenous ligands for ER-beta; Weihua Z. et al. PNAS 98: 6330–5 (2001). 3-Beta, 17-beta-androstanediol is a major metabolite of dihydrotestosterone (DHT), the 5-alpha-reduced active intracellular androgen in male accessory sex organs. ER-beta activation also stimulates increased glutathione S-transferase and quinone reductase expression. These two enzymes have been shown to possess chemoprotective detoxification properties; Chang W Y et al., Prostate 40: 115–24 (1999); Montano M M et al., J. Biol. Chem. 273: 25443–9 (1998).

With the recent identification of ER-beta, and the recognition that ER-alpha and ER-beta have different biological roles, ER-selective modulators would similarly possess significant clinical utility. Since ER-beta is strongly expressed in a number of tissues including prostate, bladder, ovary, testis, lung, small intestine, vascular endothelium, and various parts of the brain, compounds that selectively modulate ER-beta would be of clinical importance in the treatment of a variety of disease conditions, such as prostate cancer, testicular cancer, ovarian cancer, lung cancer, cardiovascular diseases, neurodegenerative disorders, urinary incontinence, CNS disorders, GI tract disorders, and osteoporosis. Such compounds would have minimal effect on tissues that contain ER-alpha, and thus exhibit different side-effect profiles. Thus, ER-beta agonists will display different therapeutic profiles compared to ER-alpha antagonists or agonists, and would be preferentially beneficial in tissues relying on ER-beta signaling.

The prostate gland produces components that are found in the semen and blood. Some of these are regulatory peptides. The prostate gland comprises stroma and epithelium cells, the latter group consisting of columnar secretory cells and basal non-secretory cells. The proliferation of these basal cells, as well as stroma cells gives rise to benign prostatic hyperplasia (BPH), which is one common prostate disease. BPH is a progressive condition that is characterized by the nodular enlargement of the prostatic tissue resulting in obstruction of the urethra. This results in increased frequency of urination, noncuria, poor urine stream, and hesitation or delay in starting the urine flow. Consequences of BPH can include hypertrophy of bladder smooth muscle, decompensated bladder, and increased incidence of urinary tract infection. The development of BPH is considered to be an inescapable phenomenon for the aging male population. BPH is observed in approximately 70% of males over the age of 70. Drug treatment for BPH currently employs alpha andrenergic antagonists for symptomatic relief or steroid 5-alpha reductase inhibitors to reduce hyperplastic tissue bulk. These approaches are of limited therapeutic benefit.

Mortality due to prostatic cancer when the strategem of watchful waiting is adopted is generally low (9%–15%) in men who have localized tumors. However, these rates pertain to patients with localized disease; they do not necessarily apply to younger men at higher risk. Younger men with stage T1a tumors have a longer projected period of risk than older men with the same stage of the disease and are therefore candidates for a potentially curative treatment. In studies of watchful waiting, the high rates of disease progression (34%–80%) indicate that few clinically evident prostate cancers are dormant.

BRIEF SUMMARY OF THE INVENTION

The present invention relates to novel benzopyran derivatives of formula (I):

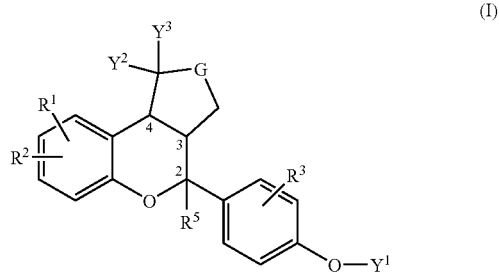

(I)

or derivatives of formula II

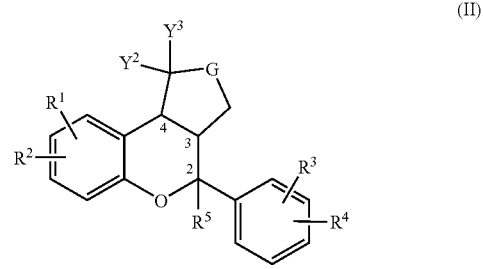

(II)

wherein

R¹, R², R³ and R⁴, are each independently —H, $C_1$–$C_6$ alkyl, —OH, $C_1$–$C_6$ alkoxy, halo, amido or —$CF_3$;

R⁵ is hydrogen or $C_1$–$C_6$ alkyl;

Y¹, Y², and Y³ are each independently —H or $C_1$–$C_6$ alkyl; and G is —$CH_2$—, —$CH_2$—$CH_2$—, or —$CH_2$—$CH_2$—$CH_2$—;

or a pharmaceutically acceptable salt thereof.

Compounds of the invention include the following, which should not be construed as in any way limiting the compounds included in the invention:

a) (±)-2-(4-hydroxyphenyl)-6-hydroxy-cyclopentyl[c]3,4-dihydro-2H-1-benzopyran
b) (±)-2-(4-hydroxyphenyl)-6-trifluoromethyl-cyclopentyl[c]3,4-dihydro-2H-1-benzopyran
c) (±)-2-(4-hydroxyphenyl)-6-methyl-cyclopentyl[c]3,4-dihydro-2H-1-benzopyran
d) (±)-2-(4-hydroxyphenyl)-6-fluoro-cyclopentyl[c]3,4-dihydro-2H-1-benzopyran
e) (±)-2-(4-hydroxyphenyl)-5-hydroxy-cyclopentyl[c]3,4-dihydro-2H-1-benzopyran
f) (±)-2-(4-hydroxyphenyl)-7-hydroxy-cyclopentyl[c]3,4-dihydro-2H-1-benzopyran
g) (±)-2-(4-hydroxyphenyl)-6-hydroxy-8-methyl-cyclopentyl[c]3,4-dihydro-2H-1-benzopyran
h) (±)-2-(4-hydroxyphenyl)-6-hydroxy-cycloheptyl[c]3,4-dihydro-2H-1-benzopyran
i) (±)-2-(4-hydroxyphenyl)-6-hydroxy-8-methoxy-cyclopentyl[c]3,4-dihydro-2H-1-benzopyran
j) (±)-2-(4-hydroxyphenyl)-6-hydroxy-11,11-dimethyl-cyclopentyl[c]3,4-dihydro-2H-1-benzopyran,
k) (±)-2-(4-hydroxyphenyl)-6-hydroxy-11,11-diethyl-cyclopentyl[c]3,4-dihydro-2H-1-benzopyran,
l) (±)-2-(4-hydroxyphenyl)-6-methoxy-cyclopentyl[c]3,4-dihydro-2H-1-benzopyran,
m) (±)-2-(4-hydroxy-3-methylphenyl)-6-hydroxy-cyclopentyl[c]3,4-dihydro-2H-1-benzopyran,
n) (±)-2-(2-methyl-4-hydroxyphenyl)-6-hydroxy-cyclopentyl[c]3,4-dihydro-2H-1-benzopyran,
o) (±)-2-(4-hydroxyphenyl)-cyclopentyl[c]3,4-dihydro-2H-1-benzopyran,
p) (±)-2-(4-hydroxyphenyl)-6-hydroxy-7-methyl-cyclopentyl[c]3,4-dihydro-2H-1-benzopyran,
q) (±)-2-(4-hydroxyphenyl)-6-hydroxy-cyclohexyl[c]3,4-dihydro-2H-1-benzopyran,
r) (±)-2-(4-methoxyphenyl)-6-methoxy-cyclopentyl[c]3,4-dihydro-2H-1-benzopyran,
s) (±)-2-(4-aminocarbonylphenyl)-6-aminocarbonyl-cyclopentyl[c]3,4-dihydro-2H-1-benzopyran,
t) (±)-2-(4-aminocarbonylphenyl)-6-hydroxy-cyclopentyl[c]3,4-dihydro-2H-1-benzopyran,
u) (±)-2-(4-hydroxyphenyl)-6-aminocarbonyl-cyclopentyl[c]3,4-dihydro-2H-1-benzopyran,
v) (±)-2-(4-methoxyphenyl)-6-hydroxy-cyclopentyl[c]3,4-dihydro-2H-1-benzopyran,
w) (±)-2-methyl-2-(4-hydroxyphenyl)-6-hydroxy-cyclopentyl[c]3,4-dihydro-2H-1-benzopyran,
x) (±)-2-ethyl-2-(4-hydroxyphenyl)-6-hydroxy-cyclopentyl[c]3,4-dihydro-2H-1-benzopyran,
y) (±)-2-(1-methylethyl)-2-(4-hydroxyphenyl)-6-hydroxy-cyclopentyl[c]3,4-dihydro-2H-1-benzopyran a pharmaceutically acceptable salt or enantiomer thereof.

In a second embodiment, the present invention provides a pharmaceutical composition comprising a therapeutically effective amount of a compound of formula (I) and a pharmaceutically acceptable carrier.

In a further embodiment, the present invention provides medical methods of employing compounds formula (I) as agonists of estrogen receptor ("ER") beta, further utilized for the treatment of ER beta-mediated diseases such as prostate cancer, benign prostatic hyperplasia, testicular cancer, cardiovascular diseases, neurodegenerative disorders, urinary incontinence, central nervous system (CNS) disorders, gastrointestinal (GI) tract disorders, and osteoporosis.

DETAILED DESCRIPTION OF THE INVENTION

As used in this application:

a) the term "amido" refers to an aminocarbonyl (—C(O)NH2) group;

b) the term "halo" refers to a fluorine atom, chlorine atom, bromine atom, or iodine atom;

b) the term "$C_1$–$C_6$ alkyl" refers to a branched or straight chained alkyl radical containing from 1 to 6 carbon atoms, such as methyl, ethyl, n-propyl, isopropyl, n-butyl, isobutyl, sec butyl, t-butyl, pentyl, hexyl, etc.;

c) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, sec-butoxy, t-butoxy, pentoxy, hexoxy, etc;

d) the designation "⌇" refers to a bond for which the stereochemistry is not designated;

e) the designation "▬" refers to a bond that protrudes forward out of the plane of the page;

f) the designation "▮▮▮▮" refers to a bond that protrudes backward out of the plane of the page;

g) as used in the preparations and examples the following terms have the indicated meanings; "ng" refers to nanograms; "μg" refers to micrograms; "mg" refers to milligrams; "g" refers to grams; "kg" refers to kilograms; "nmole" refers to nanomoles; "mmol" refers to millimoles; "mol" refers to moles; "μL" refers to microliters; "mL" refers to milliliters; "L" refers to liters; "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]^2_D{}^0$" refer to specific rotation of the D line of sodium at 20° C. obtained in a 1 decimeter cell; "c" refers to concentration in g/mL; "nM" refers to nanomolar; "μM" refers to micromolar; "mM" refers to millimolar; "M" refers to molar; "$K_i$" refers to inhibiton constant; "$K_d$" refers to dissociation constant; "psi" refers to pounds per square inch; "rpm" refers to revolutions per minute; "HPLC" refers to high performance liquid chromatography; "HRMS" refers to high resolution mass spectrum; "THF" refers to tetrahydrofuran; "brine" refers to a saturated aqueous solution of sodium chloride; "L.O.D." refers to loss on drying; "μCi" refers to microcuries; "i.p." refers to intraperitoneally; "i.v." refers to intravenously; and "DPM" refers to disintegrations per minute;

h) by the designation

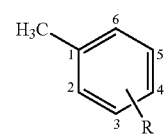

it is understood that the methyl is attached at the 1-position and the substituent or substituents represented by R can be attached in any of the 2, 3, 4, 5, or 6 positions;

i) the designation

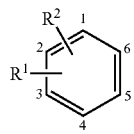

refers to a phenyl or substituted phenyl and it is understood that either substituent can be attached at any one of positions 1, 2, 3, 4, 5, or 6. It is further understood that when one of the substituents is attached at the 1-position the other substituent represented by R can be attached in any of the 2, 3, 4, 5, or 6 positions, that when one of the substituents is attached at the 2-position the other substituent represented by R can be attached in any of the 1, 3, 4, 5, or 6 positions, that when one of the substituents is attached at the 3-position the other substituent represented by R can be attached in any of the 1, 2, 4, 5, or 6 positions, that when one of the substituents is attached at the 4-position the other substituent represented by R can be attached in any of the 1, 2, 3, 5, or 6 positions, that when one of the substituents is attached at the 5-position the other substituent represented by R can be attached in any of the 1, 2, 3, 4, or 6 positions, and that when one of the substituents is attached at the 6-position the other substituent represented by R can be attached in any of the 1, 2, 3, 4, or 5 positions;

j) the numbering system and naming of the tricyclic ring system of formula (I) and formula (II) are as follows:

where G is —CH2-

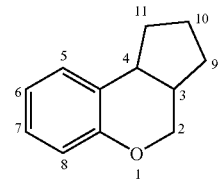

cyclopentyl[c]3,4-dihydro-2H-1-benzopyran where G is —CH2-CH2-

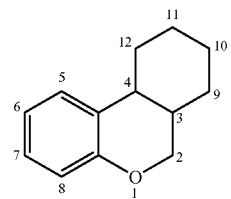

cyclohexyl[c]3,4-dihydro-2H-1-benzopyran where G is —CH2-CH2-CH2-

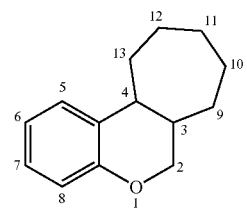

cycloheptyl[c]3,4-dihydro-2H-1-benzopyran k) the term "enantiomeric excess" or "ee" refers to the percent by which one enantiomer, E1, is in excess in a mixture of the two enantiomers, E1 plus E2, such that $\{(E1-E2)\div(E1+E2)\}\times 100=ee$;

The compounds used in the method of the present invention may have one or more asymmetric centers. As a consequence of these chiral centers, the compounds of the present invention occur as racemates and as individual enantiomers, as well as diastereomers and mixtures of diastereomers. All asymmetric forms, individual isomers and combinations thereof, are within the scope of the present invention. The three main chiral centers, signified as 2, 3, and 4, are illustrated in formula (I). The preferred relative stereochemistry of compounds of formula (I) is when chiral centers 2, 3, and 4 are all in the cis-configuration, as demonstrated by formulae IB and IC below:

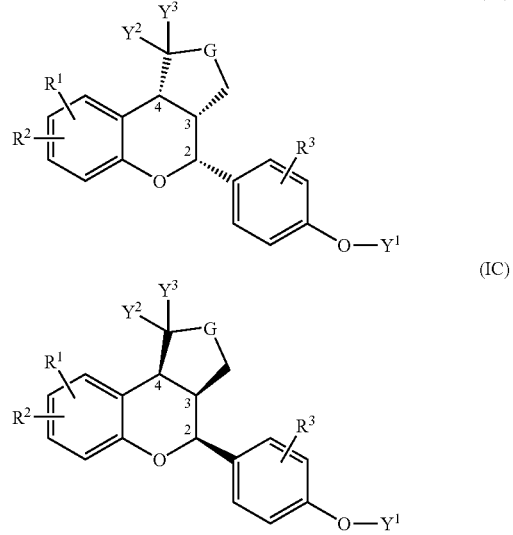

For the purpose of this invention, a compound designated "IB racemic" or "IC racemic", or their structure, indicates a racemic structure of compound IB and IC. Also, for the purpose of this invention, a compound designated "ID racemic" or "IE racemic", or their structure as shown below, indicates a racemic structure of compound ID and IE.

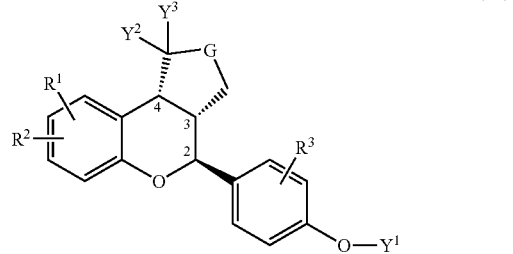

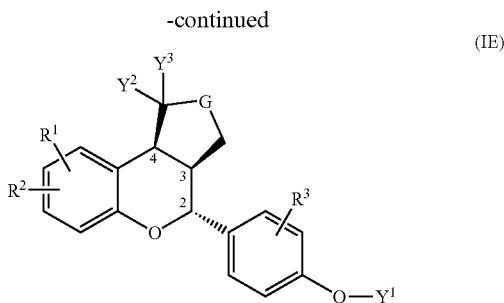

(IE)

In order to preferentially prepare one optical isomer over its enantiomer, a number of routes are available. As an example, a mixture of enantiomers may be prepared, and then the two enantiomers may be separated. A commonly employed method for the separation of a racemic mixture is the use of chiral high pressure liquid chromatography. Further details regarding resolution of enantiomeric mixtures may be found in J. Jacques, et al., Enantiomers, Racemates, and Resolutions, (1991). "The term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (I). Illustrative inorganic acids that form suitable salts include hydrochloric, hydrobromic, sulphuric, and phosphoric acid and acid metal salts such as sodium monohydrogen orthophosphate, and potassium hydrogen sulfate. Illustrative organic acids that form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxy-benzoic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (I). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Preferred embodiments of formula (I) are provided below:
(1) Compounds in which the chiral centers designated as 2, 3, and 4 are all in the cis-position;
(2) Compounds in which G is $CH_2$— are preferred;
(3) Compounds in which $Y^2$ and $Y^3$ are both —H are preferred;
(4) Compounds in which one of $R^1$ and $R^2$ is —OH are preferred;
(5) Compounds in which $R^3$ is —H are preferred;
(6) Compounds in which $Y^1$ is —H are preferred;
(7) Compounds in which one of $R^1$ and $R^2$ is —OH and the other is —H are preferred.

It is understood that further preferred embodiments of formula (I) can be selected by requiring one or more of the preferred embodiments above. For example, the limitations of (1) can be combined with the limitations of (2); the limitations of (3) can be combined with the limitations of (4); the limitations of (1), (2), (3), (5), (6), and (7) can be combined; and the like.

Another embodiment of the present invention are compounds of the formula III:

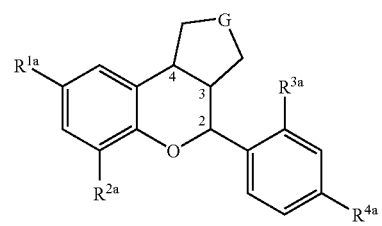

III wherein
$R^{1a}$ is —H, —OH, or —F;
$R^{2a}$ is —H, —$CH_3$, or —$OCH_3$;
$R^{3a}$ is —H or —$CH_3$;
G is —$CH_2$—, —$CH_2$—$CH_2$—, or —$CH_2$—$CH_2$—$CH_2$—; and or a pharmaceutically acceptable salt thereof.

Another embodiment of the present invention are compounds of the formula IV:

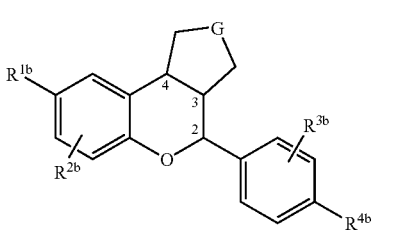

(IV)

wherein
$R^{1b}$ is amido or hydroxy;
$R^{2b}$ is —H, or $C_1$–$C_6$alkyl;
$R^{3b}$ is —H or $C_1$–$C_6$ alkyl;
$R^{4b}$ is amido or hydroxy; and
G is —$CH_2$—, —$CH_2CH_2$—, —$CH_2CH_2CH_2$—;

or a pharmaceutically acceptable salt thereof.

Illustrative examples of the compounds encompassed by the present invention include the racemic mixtures and the specific enantiomers of the following compounds:

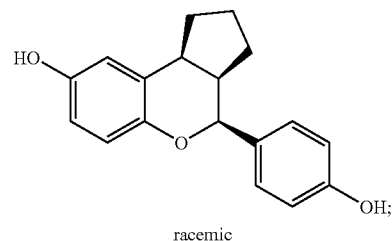

racemic

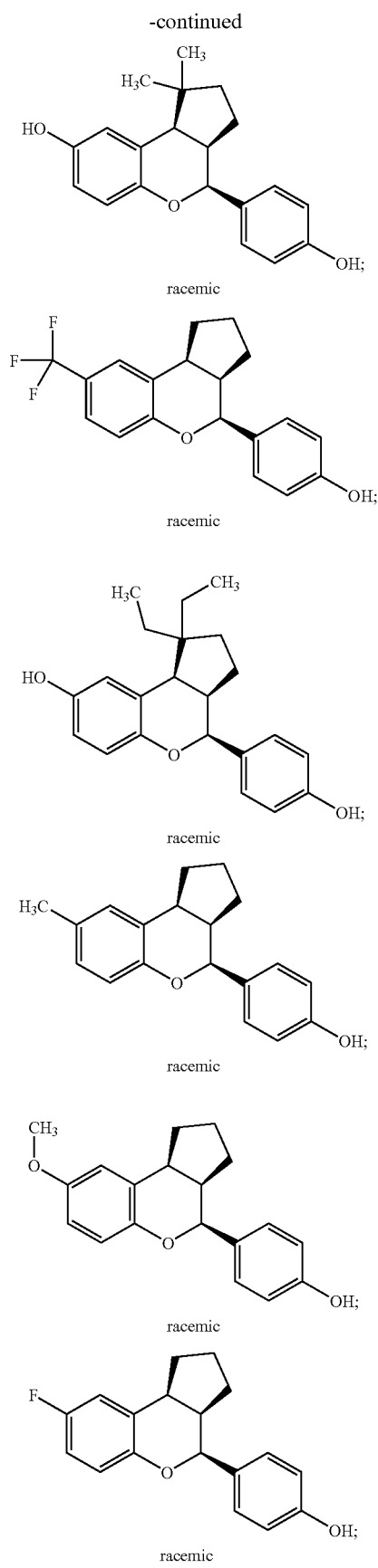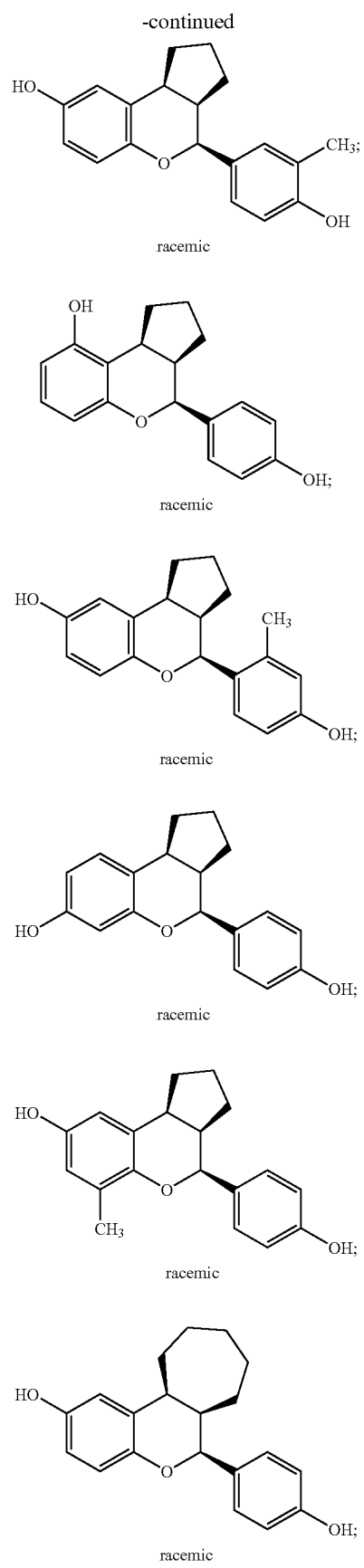

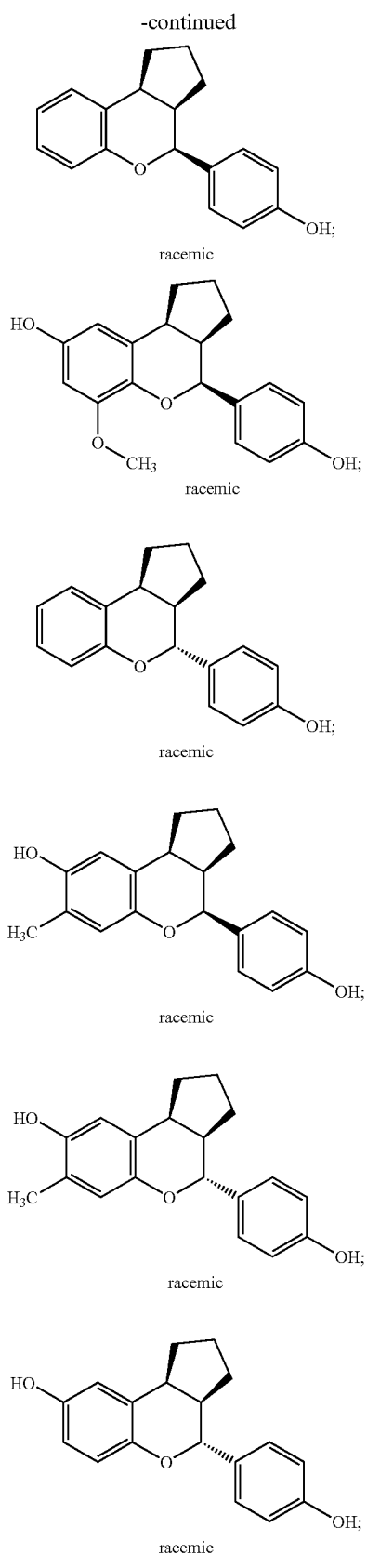
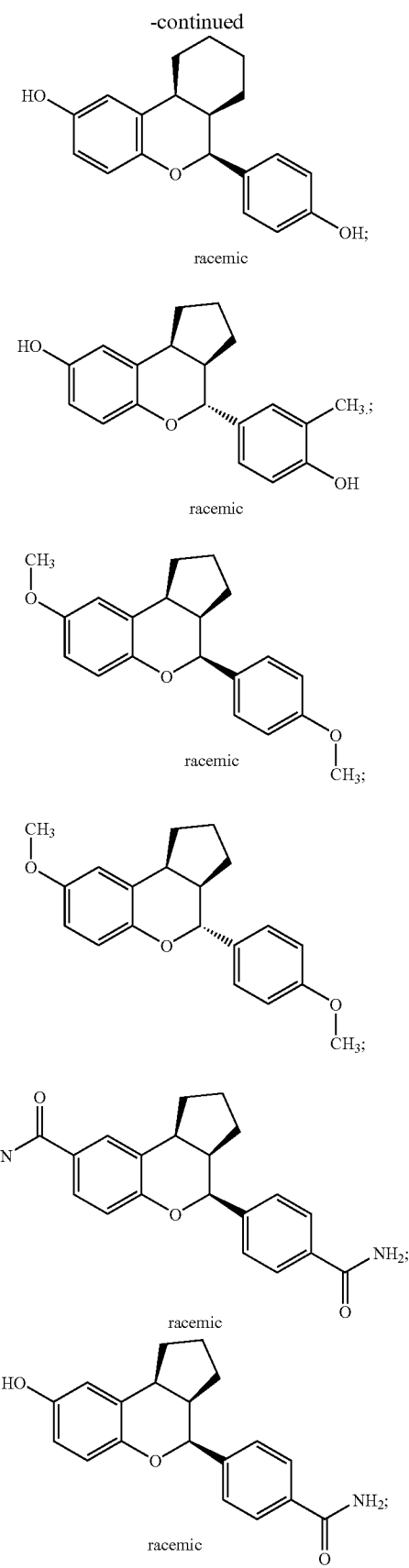

-continued
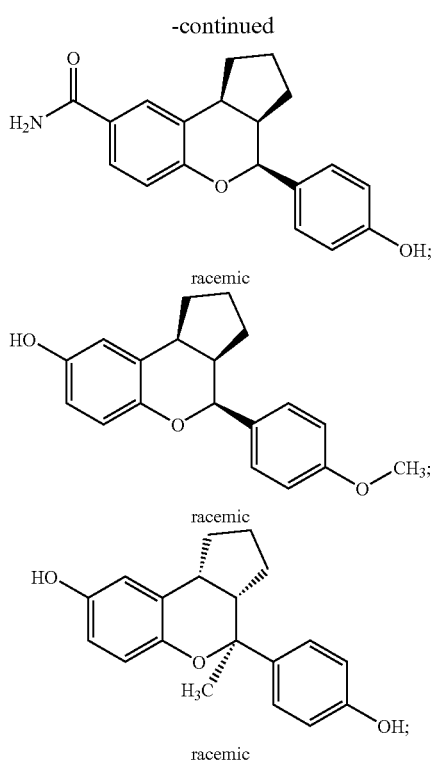
racemic
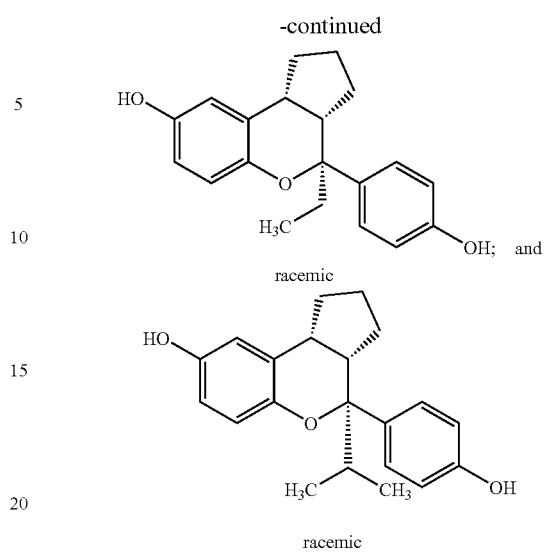
racemic
Reaction Schemes
Compounds of formula (I) and intermediates thereof can be prepared as described in Reaction Schemes A through D below. All substituents, unless otherwise indicated, are previously defined. The reagents and starting materials are readily available to one of ordinary skill in the art.
SCHEME A
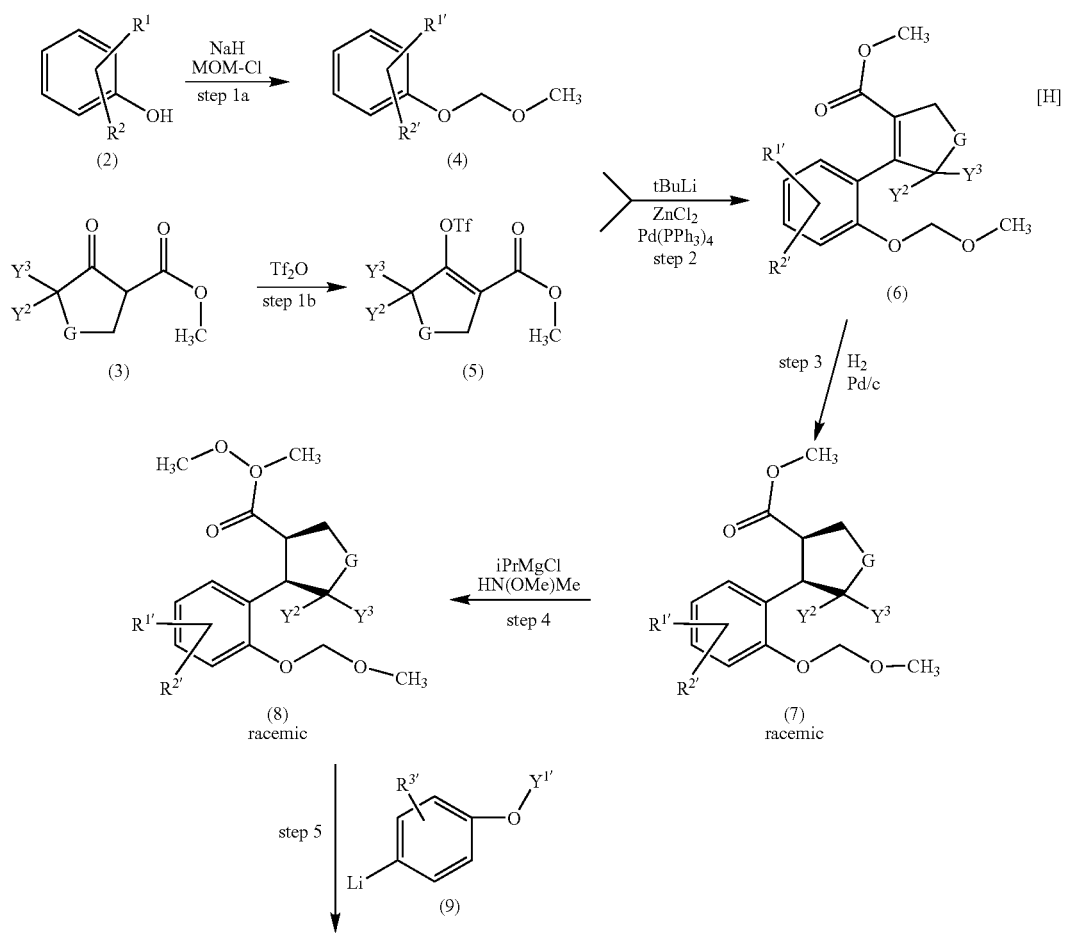

-continued

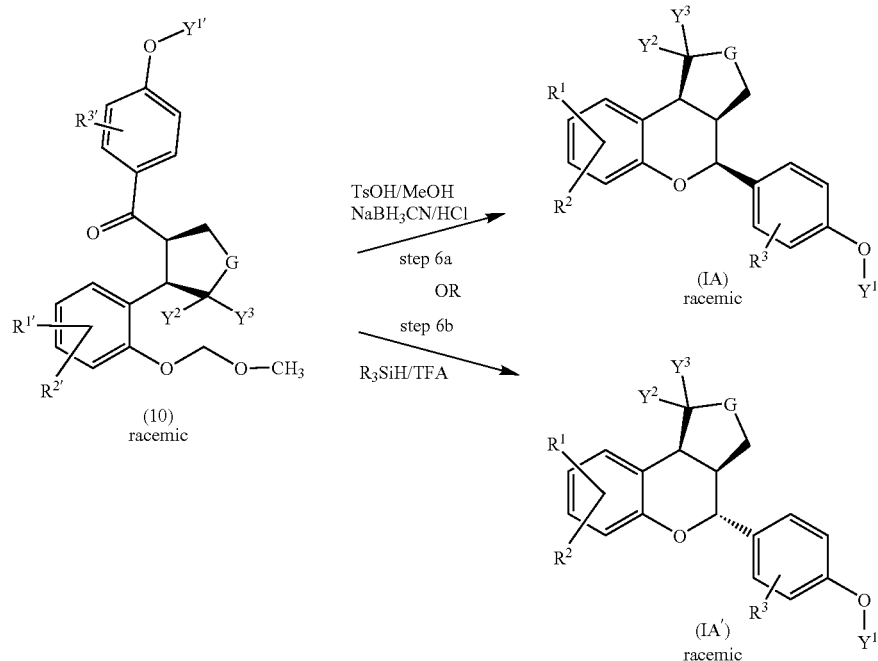

As used herein, $R^{1'}$, $R^{2'}$, $R^{3'}$, and $Y^{1'}$ correspond to the substituents $R^1$, $R^2$, $R^3$, and $Y^1$, respectively, except for when the $R^1$, $R^2$, and $R^3$ substituents would be hydroxy and the $Y^1$ substituent would be —H (making the —O—$Y^1$ group a hydroxy). In these cases, the corresponding hydroxy group is protected with an alkoxymethylether, such as methoxymethyl ("MOM") or methoxyethoxymethyl ("MEM").

In reaction Scheme A, step 1a, the hydroxy groups on the phenol of formula (2) are protected with a suitable protecting group to provide the protected phenol of formula (4) utilizing techniques and procedures well know to one of ordinary skill in the art. For example, the phenol of formula (2) is combined with a suspension comprising a suitable anhydrous solvent such as anhydrous dimethylformamide (DMF) and a suitable strong base such as a metal hydride, most preferably sodium hydride. To this suspension is added an amount of alkoxymethyl ether chloride, preferably MOM—Cl, which corresponds to a roughly equimolar amount depending on the number of hydroxy groups to be protected on the phenol of formula (2). The reaction may be conducted at room temperature for a time ranging from about 30 minutes to about 2 days. The reaction is then quenched with water and an appropriate ether, such as diethyl ether or EtOAc, and the organic layer is washed with an appropriate base, such as sodium hydroxide or NaHCO$_3$, and brine. The protected phenol of formula (4) may be isolated and purified by techniques well known in the art, such as extraction, evaporation, trituration, chromatography, and recrystallization.

In Scheme A, step 1b, a 2-oxocycloalkanecarboxylate of formula (3) is activated via the triflate to provide the activated cycloalkane carboxylate of formula (5) utilizing procedures and techniques well known in the art; G. T. Crisp et al., *J. Org. Chem.* 57, 6972–6975 (1992). For example, a methyl-2-oxocycloalkanecarboxylate of formula (3) is dissolved under anhydrous conditions in a suitable solvent, such as tetrahydrofuran, dichloromethane, acetone, ethyl acetate, toluene, or diethyl ether and contacted with a suitable activating agent such as triflic anhydride. The reaction is carried out in the presence of a base, such as N-methylmorpholine, sodium carbonate, triethylamine, N,N-diisopropylethylamine, potassium carbonate, sodium bicarbonate, pyridine and 2,6-di-tert-butyl-4-methyl-pyridine. The reaction is generally carried out at temperatures of from –78° C. to ambient temperature. Generally, the reactions require 1 to 24 hours. The reaction may then be quenched. The product of formula (5) can be isolated and purified by techniques well known in the art, such as extraction, evaporation, trituration, chromatography, and recrystallization.

In Scheme A, step 2, the protected phenol of formula (4) is coupled with the activated cycloalkane carboxylate of formula (5) to provide the coupled product of formula (6). For example, the coupling reaction is conducted in the presence of butyllithium, zinc chloride and a Pd species. The reaction is preferably carried out in a suitable solvent such as tetrahydrofuran (THF), and may initially be carried out under anhydrous condition. Preferably, the protected phenol of formula (4) is dissolved in a suitable solvent such as THF, treated with butyllithium at reduced temperature, zinc chloride in solvent is then added and the temperature allowed to rise to ambient. The palladium species, such as tetrakis (triphenylphosphine)Pd(0), is added together with the activated cycloalkane carboxylate of formula (5) and the temperature is preferably raised to the reflux temperature of the solvent for a period of time ranging from about 6 to 24 hours. The coupled product of formula (6) can be isolated and purified by techniques well known in the art, such as extraction, evaporation, trituration, chromatography, and recrystallization.

In Scheme A, step 3, the coupled product of formula (6) is reduced with a suitable reducing agent to provide the reduced product of formula (7) utilizing techniques and procedures well known in the art. For example, the coupled product of formula (6) is contacted with a suitable reducing agent, such as a palladium species, preferably 5% or 10% carbon on palladium, in a suitable solvent or solvent mixture, such as methanol. The reaction is preferably carried out in the presence of a suitable base, such as a trialkylamine, more preferably, triethylamine. The reaction mixture is then heated to a temperature ranging from about 30° C. to about reflux for a period of time ranging from about 2 to 24 hours. The reduced product of formula (7) can be isolated and purified by techniques well known in the art, such as extraction, evaporation, trituration, chromatography, and recrystallization.

In Scheme A, step 4, the reduced product of formula (7) can be converted to the Weinreb-amide of formula (8). This reaction can be performed utilizing a reactin of the type described by J. M. Williams, et al., *Tetrahedron Letters* 36, 5461–5464 (1995). For example, the reduced product of formula (7) is combined with N,O-dimethylhydroxylamine hydrochloride in a suitable aprotic solvent, such as tetrahydrofuran, preferably under anhydrous conditions and cooled to a temperature ranging from about 0° C. to about −30° C., more preferably about −10° C. A suitable Grignard reagent, preferably isopropyl magnesium chloride, is then added in a molar ratio of about 1.5 and reaction mixture is stirred for about 15 minutes to 2 hours. The reaction is then quenched with a proton source such as, for example, saturated ammonium chloride. The Weinreb-amide of formula (8) can be isolated and purified by techniques well known in the art, such as extraction, evaporation, trituration, chromatography, and recrystallization.

In Scheme A, step 5, the Weinreb-amide of formula (8) is combined with the aryl lithium of formula (9) to form the ketone of formula (10). For example, the aryl lithium of formula (9) is added to a solution of Weinreb-amide of formula (8) in a suitable aprotic solvent, such as anhydrous THF, cooled to a temperature ranging from about −20° C. to about 5° C., preferably 0° C., and stirred for a period of time ranging from about 15 minutes to 3 hours. The reaction is then quenched with a proton source, such as, for example, saturated sodium bicarbonate. The ketone of formula (10) can be isolated and purified by techniques well known in the art, such as extraction, evaporation, trituration, chromatography, and recrystallization.

In Scheme A, step 6a or 6b, the ketone of formula (10) is subjected to an acid-catalyzed cyclization followed by reduction of the resulting hemiketal to provide a compound of formula (IA or IA'), which represents the racemic mixture of a compound of formula (I). For example, in step 6a, p-toluenesulfonic acid is added in roughly equimolar proportions to the ketone of formula (10) in a suitable alcohol solvent, such as anhydrous methanol. The mixture is then heated at a temperature ranging from 40° C. to 60° C., preferably 50° C., for a period of time ranging from 12 to 24 hours, preferably 18 hours. The reaction is then cooled to ambient temperature and a suitable reducing agent, such as sodium cyanoborohydride, is added along with a suitable indicator such as bromocreosol green in a procedure similar to that described by A. Srikrishna, et. Al., Tetrahedron, vol. 51, no. 11, pp. 3339–3344, 1995. Methanol saturated with hydrochloric acid is then slowly added until a yellow color is maintained. The reaction is stirred for about 1 to 2 hours past the point of final color change. The reaction is then quenched with a suitable proton acceptor, such as saturated sodium bicarbonate. This set of reaction conditions for step 6a will result in a cis-configuration of the chiral centers (e.g., those compounds in IB or IC). The R3SiH/TFA conditions of step 6b will result in a trans-configuration of the chiral centers (e.g., those compounds in ID or IE). The product of formula (IA) or (IA') can then be isolated and purified by techniques well known in the art, such as extraction, evaporation, trituration, chromatography, and recrystallization.

Alternatively, the coupled product of formula (6) may be synthesized as described in reaction Scheme B. All substituents, unless otherwise indicated, are previously defined. The reagents and starting materials are readily available to one of ordinary skill in the art.

SCHEME B

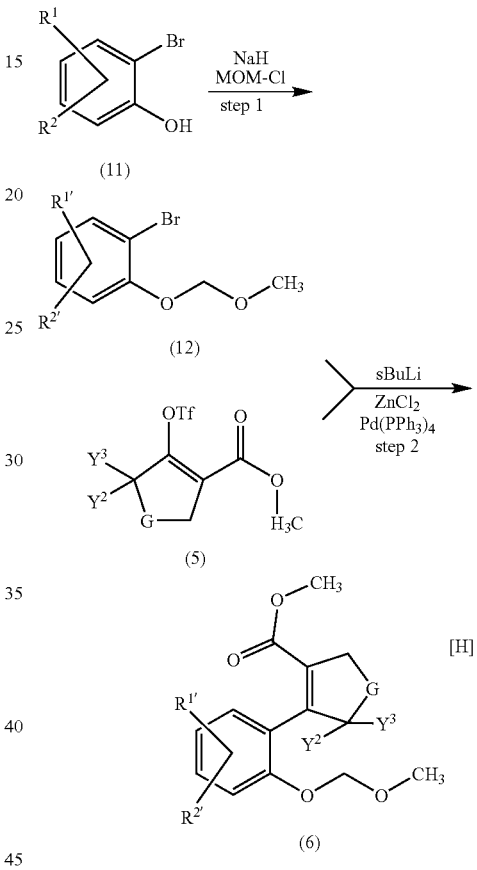

In Scheme B, step 1, the hydroxy groups on the bromophenol of formula (11) are protected with a suitable protecting group to provide the protected bromophenol of formula (12) utilizing techniques and procedures as set forth in Scheme A, step 1a.

In Scheme B, step 2, the protected bromophenol of formula (12) is coupled with the activated cycloalkane carboxylate of formula (5) to provide the coupled product of formula (6) according the techniques and procedures set forth in Scheme A, step 2.

An alternative method for providing specific bromo-substituted intermediates are provided in Scheme C.

SCHEME C

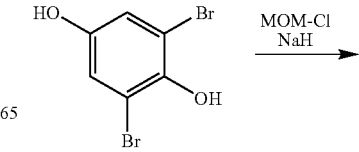

-continued
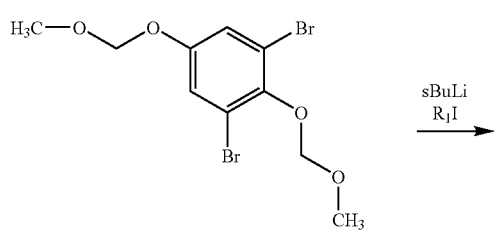
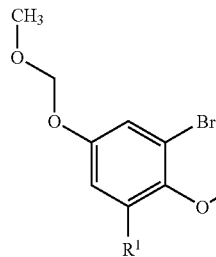
Additionally, specific compounds of formula (I) wherein $Y^1$ is methyl can be prepared according to Scheme D.
SCHEME D
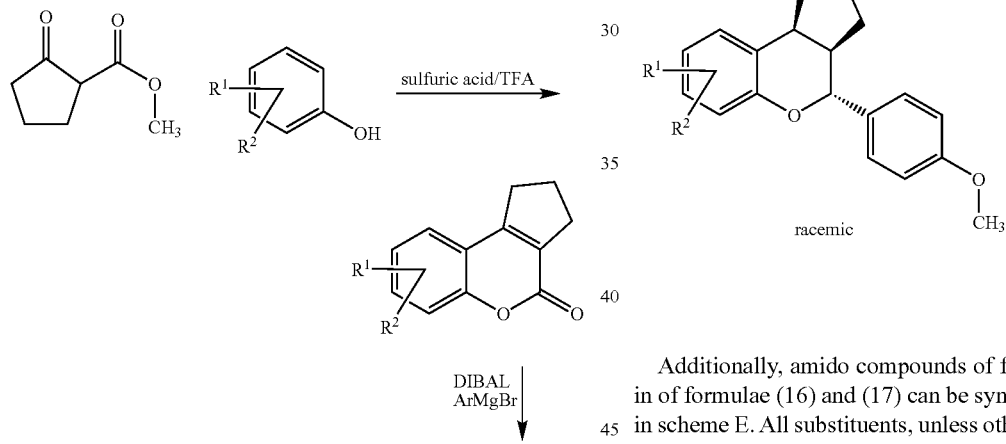
-continued
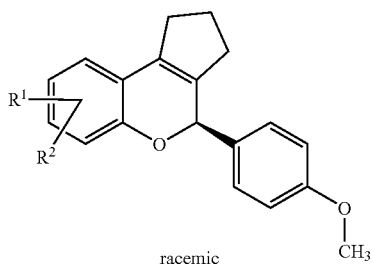
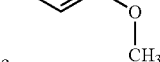
Additionally, amido compounds of formula (II) as shown in of formulae (16) and (17) can be synthesized as described in scheme E. All substituents, unless otherwise indicated, are previously defined.
SCHEME E
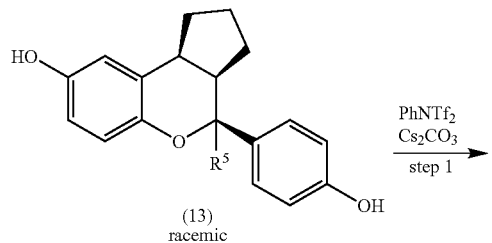

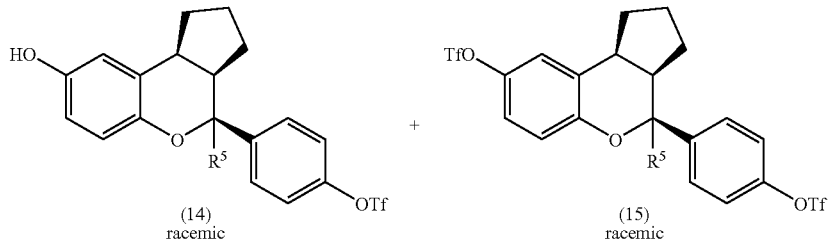

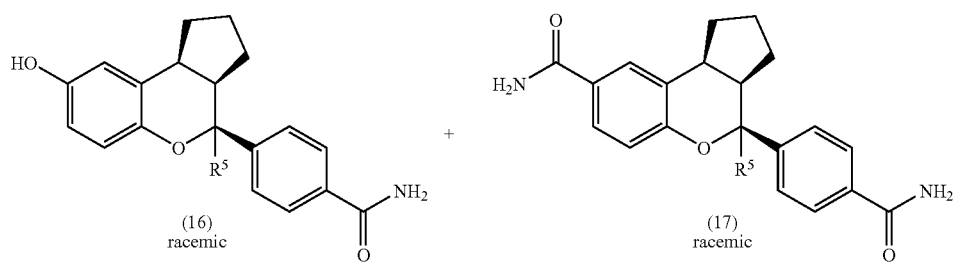

The reagents and starting materials are readily available to one of ordinary skill in the art. In scheme E, step 1, a dihydroxy of formula (13) can be converted to a mixture of the monotriflate of formula (14) and the ditriflate of formula (15). The resulting mixture can be separated using conventional chromatography. In scheme E, step 2, the monotriflate of formula (14) and the ditriflate of formula (15) are cross coupled under palladium catalyzed carbonylation conditions with 1,1,1,3,3,3-hexamethyldisilylazane to afford carboxamides of formulae (16) and (17).

Additionally, the amido of formula (19) can be synthesized as described in scheme F. All substituents, unless otherwise indicated, are previously defined.

SCHEME F

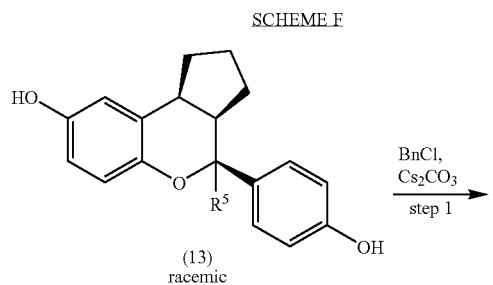

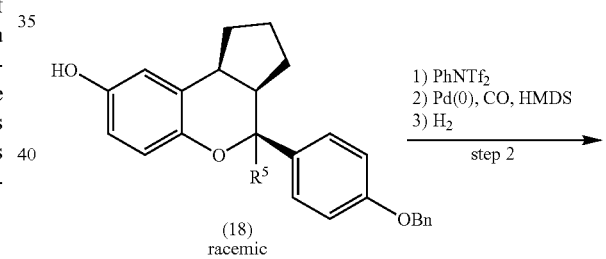

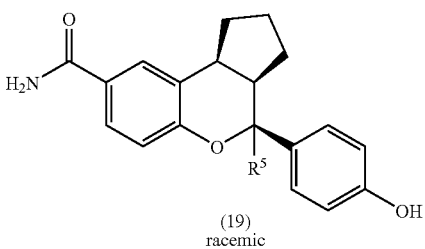

The reagents and starting materials are readily available to one of ordinary skill in the art. In scheme F, step 1, the dihydroxy of formula (13) can be selectively converted to the benzyl ether of formula (18). In scheme F, step 2, the remaining phenol is triflated, then immediately cross-coupled under identical conditions as scheme E, step 2. Finally, the benzyl group is removed to afford the carboxamide of formula (19) after HPLC purification.

Additionally, compounds where $R^5$ is $C_1$–$C_6$ alkyl can be prepared as described in Scheme G.

SCHEME G

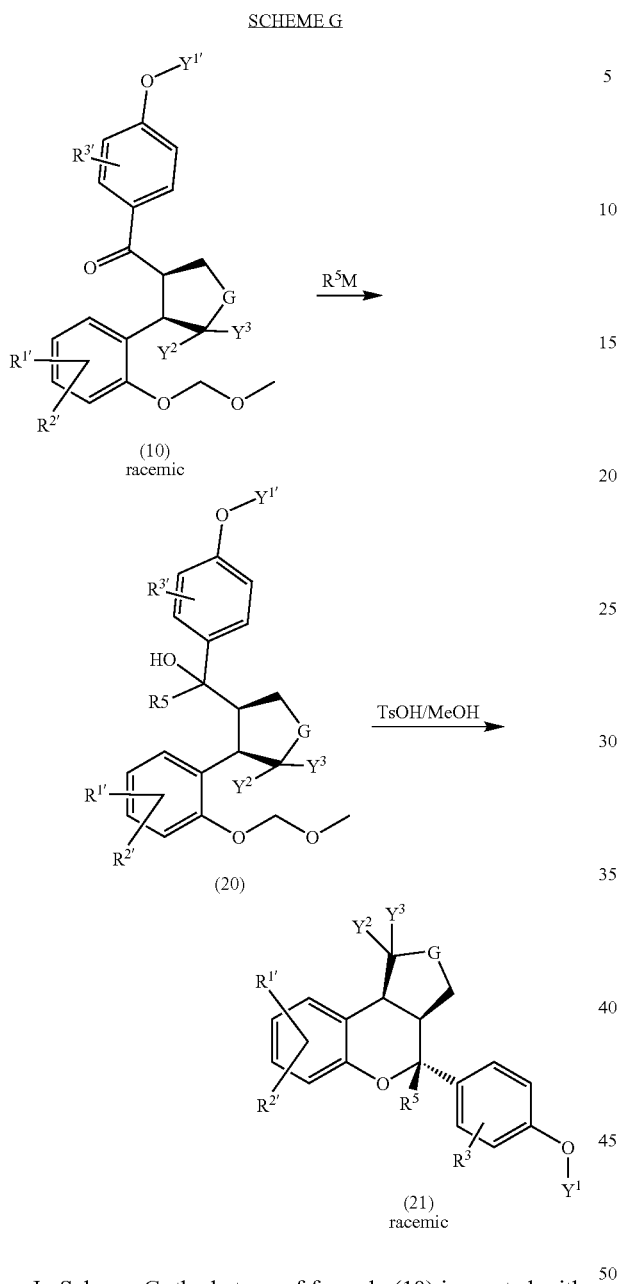

In Scheme G, the ketone of formula (10) is reacted with an alkyl organometallic reagent such as methyl lithium or ethyl magnesium bromide to form tertiary alcohols of formula (20). Under the acidic conditions described in Scheme A, step 6a, the tertiary alcohols form benzopyrans of formula (21).

Preparation 1

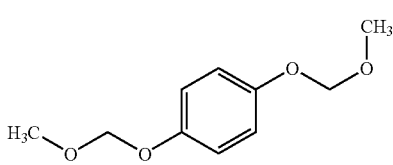

Stir a suspension of sodium hydride (60% in mineral oil, 3.81 g, 95.45 mmol) in anhydrous DMF (50 mL) under nitrogen atmosphere at 0° C. and add a solution of hydroquinone (5.00 g, 45.45 mmol) in anhydrous DMF (50 mL) dropwise. Add to this suspension methoxymethyl chloride (7.2 mL, 95.45 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 1 (5.64 g, 63%) as a clear oil. $^1$H NMR (CDCl$_3$): 6.97 (s, 4H), 5.11 (s, 4H), 3.47 (s, 6H).

Preparation 2

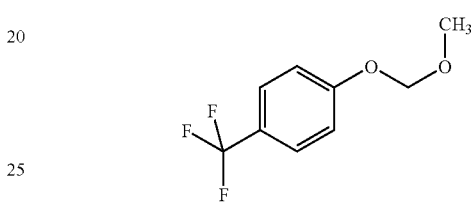

Stir a suspension of sodium hydride (60% in mineral oil, 0.67 g, 16.67 mmol) in anhydrous DMF (25 mL) under nitrogen atmosphere at 0° C. and add a solution of α,α,α-triflouromethyl-p-creosol (2.50 g, 15.15 mmol) in anhydrous DMF (25 mL) dropwise. Add to this suspension methoxymethyl chloride (1.3 mL, 16.67 mmol) dropwise. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 2 (2.50 g, 80%) as a clear oil. $^1$H NMR (CDCl$_3$): 7.25 (d, J=8.6, 2H), 6.83 (d, J=8.3, 2H), 4.93 (s, 2H), 3.19 (s, 3H).

Preparation 3

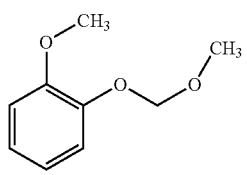

Stir a suspension of sodium hydride (60% in mineral oil, 0.89 g, 22.17 mmol) in anhydrous DMF (25 mL) under nitrogen atmosphere at 0° C. and add a solution of gualacol (2.50 g, 20.16 mmol) in anhydrous DMF (25 mL) dropwise. Add to this suspension methoxymethyl chloride (1.7 mL, 22.17 mmol) dropwise. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 3 (2.22 g, 66%) as a clear oil. $^1$H NMR (CDCl$_3$): 6.97–6.89 (m, 4H), 5.01 (s, 2H), 3.89 (s, 3H), 3.22 (s, 3H).

Preparation 4

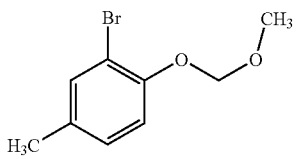

Stir a suspension of sodium hydride (60% in mineral oil, 0.41 g, 10.30 mmol) in anhydrous DMF (25 mL) under nitrogen atmosphere at 0° C. and add a solution of 2-bromo-4-methylphenol (2.50 g, 14.71 mmol) in anhydrous DMF (25 mL) dropwise. Add to this suspension methoxymethyl chloride (0.78 mL, 10.30 mmol) dropwise. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 4 (2.45 g, 72%) as a clear oil.

Preparation 5

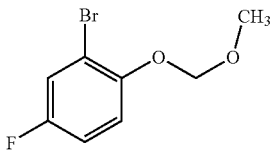

Stir a suspension of sodium hydride (60% in mineral oil, 0.58 g, 14.40 mmol) in anhydrous DMF (25 mL) under nitrogen atmosphere at 0° C. and add a solution 2-bromo-4-flourophenol (2.50 g, 13.09 mmol) in anhydrous DMF (25 mL) dropwise. Add to this suspension methoxymethyl chloride (1.1 mL, 14.40 mmol) dropwise. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 5 (2.71 g, 88%) as a clear oil. $^1$H NMR (CDCl$_3$): 7.40–7.35 (m, 1H), 7.01–6.89 (m, 1H), 6.85–6.79 (m, 1H), 4.99 (s, 2H), 3.87 (s, 3H).

Preparation 6

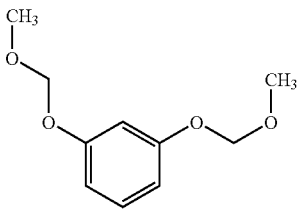

Stir a suspension of sodium hydride (60% in mineral oil, 1.90 g, 47.68 mmol) in anhydrous DMF (25 mL) under nitrogen atmosphere at 0° C. and add a solution of resorcinol (2.50 g, 22.70 mmol) in anhydrous DMF (25 mL) dropwise. Add to this suspension methoxymethyl chloride (3.6 mL, 47.68 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 6 (2.49 g, 55%) as a clear oil. $^1$H NMR (CDCl$_3$): 7.20 (t, J=8.2, 1H), 6.74–6.68 (m, 3H), 5.16 (s, 4H), 3.48 (s, 6H). MS calcd. 198.2; MS (M+1) 199.0.

Preparation 7

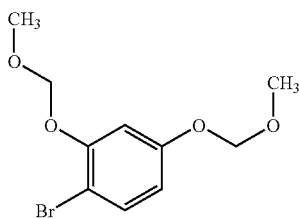

Stir a suspension of sodium hydride (60% in mineral oil, 1.11 g, 27.78 mmol) in anhydrous DMF (25 mL) under nitrogen atmosphere at 0° C. and add a solution of 4-bromoresorcinol (2.50 g, 13.22 mmol) in anhydrous DMF (25 mL) dropwise. Add to this suspension methoxymethyl chloride (2.1 mL, 27.78 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 7 (2.46 g, 67%) as a clear oil. $^1$H NMR (CDCl$_3$): 7.40 (d, J=7.8, 1H), 6.87 (d, J=2.7, 1H), 6.63 (dd, J=2.7, 7.8, 1H), 5.22 (s, 2H), 5.14 (s, 2H), 3.51 (s, 3H), 3.46 (s, 3H). MS calcd 277.12; MS (M+1) 277.2, 279.2.

Preparation 8

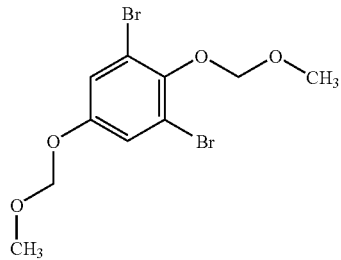

Stir a suspension of sodium hydride (60% in mineral oil, 1.58 g, 39.21 mmol) in anhydrous DMF (50 mL) under nitrogen atmosphere at 0° C. and add a solution of 2,6-dibromohydroquinone (5.00 g, 18.67 mmol) in anhydrous DMF (50 mL) dropwise. Add to this suspension methoxymethyl chloride (3.0 mL, 39.21 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 8 (3.49 g, 53%) as a clear oil. $^1$H NMR (CDCl$_3$): 7.23 (s, 2H), 5.10 (s, 4H), 3.46 (s, 6H).

Preparation 9

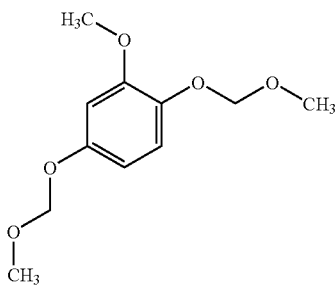

Stir a suspension of sodium hydride (60% in mineral oil, 3.00 g, 74.92 mmol) in anhydrous DMF (50 mL) under nitrogen atmosphere at 0° C. and add a solution of methoxyhydroquinone (5.00 g, 35.67 mmol) in anhydrous DMF (50 mL) dropwise. Add to this suspension methoxymethyl chloride (5.2 mL, 74.92 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 9 (5.84 g, 72%) as a clear oil. $^1$H NMR (CDCl$_3$): 7.05 (d, J=8.6, 1H), 6.63 (d, J=2.7, 1H), 6.55 (dd, J=9.0, 2.7, 1H), 5.14 (s, 2H), 5.12 (s, 2H), 3.86 (s, 3H), 3.51 (s, 3H), 3.47 (s, 3H).

Preparation 10

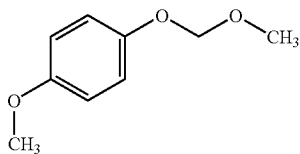

Stir a suspension of sodium hydride (60% in mineral oil, 3.54 g, 88.61 mmol) in anhydrous DMF (100 mL) under nitrogen atmosphere at 0° C. and add a solution of 4-methoxyphenol (10.00 g, 80.55 mmol) in anhydrous DMF (50 mL) dropwise. Add to this suspension methoxymethyl chloride (6.7 mL, 88.61 mmol) dropwise. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield Preparation 10 (11.55 g, 85%) as a clear oil.

Preparation 11

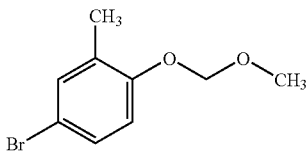

To a suspension of hexane washed sodium hydride (60% in mineral oil, 1.64 g, 68.2 mmol) in anhydrous THF (70 mL) under a nitrogen atmosphere at room temperature was added a solution of 4-bromo-2-cresol (10.6 g, 56.8 mmol) plus methoxymethyl bromide (5.6 mL, 68.2 mmol) in anhydrous THF (30 mL) dropwise. After stirring 18 h, the mixture was partitioned between dilute sodium bicarbonate aqueous and diethylether. The organic layer was washed with water and brine, dried over anhydrous sodium sulfate, concentrated in vacuo to yield Preparation 11 (12.74 g, 97%) as a clear oil.

Preparation 12

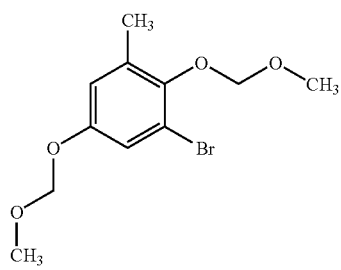

Cool a solution of Preparation 8 (1.00 g, 2.81 mmol) to −78° C. and add s-BuLi (1.3 M in cylcohexane, 2.10 mL, 2.81 mmol) dropwise. Stir the solution for 15 minutes, then add methyl iodide (0.18 mL, 2.81 mmol) and stir overnight, allowing to warm to ambient temperature. Quench with saturated sodium bicarbonate and add ethyl acetate. Wash with brine, dry the organic layer over sodium sulfate, concentrate in vacuo, and flash chromatograph with 10% ethyl acetate/hexane to yield Preparation 12 (0.66 g, 81%) as a clear oil. $^1$H NMR (CDCl$_3$): 7.12 (d, J=2.9, 1H), 6.83 (d, J=2.9, 1H), 5.10 (s, 2H), 5.04 (s, 2H), 3.63 (s, 3H), 3.48 (s, 3H), 2.30 (s, 3H). MS calcd 291.1; MS (M+1) 291.2, 293.2.

Preparation 13

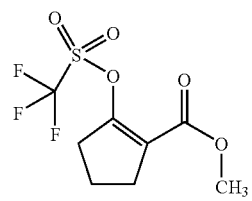

This preparation was followed according to J. Org. Chem. 57, 1992, 6972–6975. Stir a solution of methyl 2-oxocylcopentanecarboxylate (10.0 g, 70.42 mmol) in anhydrous dichloromethane (300 mL) cooled to −78° C. and add diisopropylethylamine (61.5 mL, 352.1 mmol) and triflic anhydride (14.2 mL, 84.51 mmol). Stir the reaction was stir for 16 hours, allowing it to warm to ambient temperature. Quench the reaction with water and wash with 10% citric acid followed by brine. Dry the organic layer over sodium sulfate, concentrate in vacuo, and flash chromatograph with 15% ethyl acetate/hexane to yield Preparation 13 (12.0 g, 63%) as a dark oil which is used without further purification. $^1$H NMR (CDCl$_3$): 3.79 (s, 3H), 2.75–2.68 (m, 4H), 2.03–1.98 (m, 2H).

Preparation 14

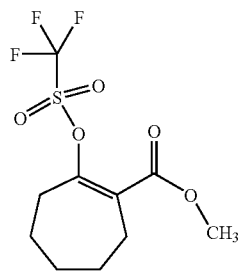

Using a method similar to the preparation of Preparation 13, with an exception of using methyl 2-oxo-1-cycloheptanecarboxylate (5.00 g, 29.37 mmol) to yield Preparation 14 (4.34 g, 49%) as a dark oil.

Preparation 15

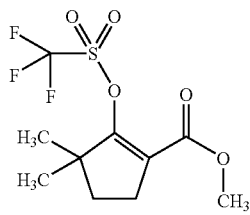

Stir a solution of methyl 2-oxo-5,5-dimethyl-cyclopentanecarboxylate (J. Chem. Soc., 1996, 1539–1540) (0.85 g, 5.00 mmol) in anhydrous dichloromethane (15 mL) cooled to −78° C. and add diisopropylethylamine (4.4 mL, 25.00 mmol) and triflic anhydride (1.0 mL, 6.00 mmol). Stir the reaction was stir for 16 hours, allowing it to warm to ambient temperature. Quench the reaction with water and wash with 10% citric acid followed by brine. Dry the organic layer over sodium sulfate, concentrate in vacuo, and flash chromatograph with 15% ethyl acetate/hexane to yield Preparation 15 (1.16 g, 77%) as a dark oil which is used without further purification. $^1$H NMR (CDCl$_3$): 3.78 (s, 3H), 2.64 (t, J=7.1, 2H), 1.83 (t, J=7.1, 2H), 1.18 (s, 6H).

Preparation 16

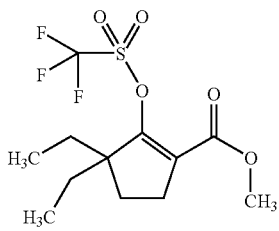

Stir a solution of methyl 2-oxo-5,5-diethyl-cyclopentanecarboxylate (J. Chem. Soc., 1996, 1539–1540) (2.94 g, 14.85 mmol) in anhydrous dichloromethane (100 mL) cooled to −78° C. and add diisopropylethylamine (13.0 mL, 74.25 mmol) and triflic anhydride (3.0 mL, 17.82 mmol). Stir the reaction was stir for 16 hours, allowing it to warm to ambient temperature. Quench the reaction with water and wash with 10% citric acid followed by brine. Dry the organic layer over sodium sulfate, concentrate in vacuo, and flash chromatograph with 15% ethyl acetate/hexane to yield Preparation 16 (3.96 g, 82%) as a dark oil which is used without further purification. $^1$H NMR (CDCl$_3$): 3.78 (s, 3H), 2.60 (t, J=7.4, 7.8, 2H), 1.83 (t, J=7.8, 7.1, 2H), 1.46 (q, J=7.4, 7.4, 7.4, 4H), 0.91 (t, J=7.4, 7.4, 6H).

Preparation 17

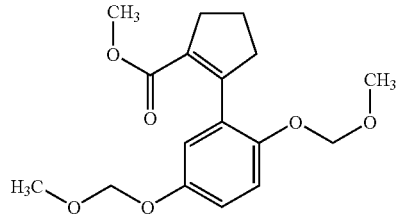

Cool a solution of Preparation 1 (0.95 g, 4.81 mmol) in anhydrous THF (25 mL) to −78° C. and add t-BuLi (1.7M in pentane, 2.8 mL, 4.81 mmol). Stir the solution 15 minutes, then warm to 0° C. Add a solution of zinc chloride (1.0 M in diethyl ether, 4.8 mL, 4.81 mmol) dropwise and allow the resulting solution to warm to ambient temperature. Cannulate this solution into a solution of Preparation 13 (0.88 g, 3.21 mmol) and tetrakis(triphenylphosphine)Pd(0) (0.37 g, 0.32 mmol) in anhydrous THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 30% ethyl acetate/hexane to yield Preparation 17 (0.56 g, 55%) as a clear oil. $^1$H NMR (CDCl$_3$): 7.04 (d, J=9.0, 1H), 6.90 (dd, J=3.1, 9.0, 1H), 6.81 (d, J=3.1, 1H), 5.10 (s, 2H), 5.02 (s, 2H), 3.56 (s, 3H), 3.46 (s, 3"), 3.42 (s, 3H), 2.80 (t, J=8.6, 8.2, 4H), 2.05–1.95 (m, 2H). MS calcd 322.2; MS (M+1) 323.1.

Preparation 18

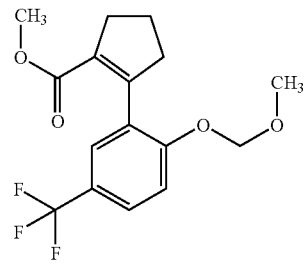

Cool a solution of Preparation 2 (2.50 g, 12.14 mmol) in anhydrous THF (40 mL) to −78° C. and add t-BuLi (1.7M in pentane, 7.9 mL, 13.35 mmol). Stir the solution 15 minutes, then warm to 0° C. Add a solution of zinc chloride (1.0 M in diethyl ether, 12.1 mL, 12.14 mmol) dropwise and allow the resulting solution to warm to ambient temperature. Cannulate this solution into a solution of Preparation 13 (3.32 g, 12.14 mmol) and tetrakis(triphenylphosphine)Pd(0) (0.70 g, 0.61 mmol) in anhydrous THF (40 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 15% ethyl acetate/hexane to yield Preparation 18 (2.87 g, 72%) as a clear oil. $^1$H NMR (CDCl$_3$): 7.49 (dd, J=1.9, 8.2, 1H), 7.37 (d, J=2.3, 1H), 7.20 (d, 8.6, 1H), 5.16 (s, 2H), 3.55 (s, 3H), 3.43 (s, 3H), 2.80 (t, J=7.4, 7.8, 4H), 2.06–1.98 (m, 2H). MS calcd 330.1; MS (M+1) 331.1.

Preparation 19

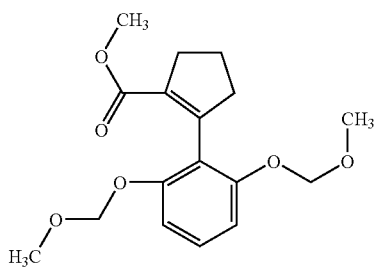

Cool a solution of Preparation 6 (2.49 g, 12.57 mmol) in anhydrous THF (25 mL) to −78° C. and add t-BuLi (1.7M in pentane, 7.4 mL, 12.57 mmol). Stir the solution 15 minutes, then warm to 0° C. Add a solution of zinc chloride (1.0 M in diethyl ether, 12.6 mL, 12.57 mmol) dropwise and allow the resulting solution to warm to ambient temperature. Cannulate this solution into a solution of Preparation 13 (2.30 g, 8.38 mmol) and tetrakis(triphenylphosphine)Pd(0) (0.48 g, 0.41 mmol) in anhydrous THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield Preparation 19 (1.70 g, 41%) as a colorless oil. $^1$H NMR (CDCl$_3$): 7.15 (t, J=8.2, 8.6, 1H), 6.78 (d, J=8.2, 2H), 5.09 (bs, 4H), 3.52 (s, 3H), 3.42 (s, 6H), 2.83–2.77 (m, 4H), 2.04–1.99 (m, 2H). MS calcd 322.1; MS (M+1) 323.1.

Preparation 20

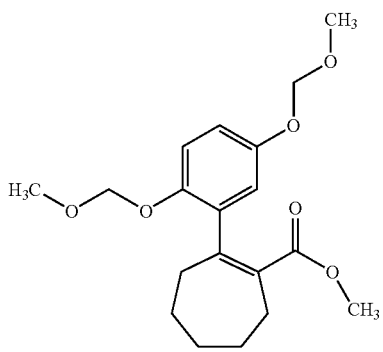

Cool a solution of Preparation 1 (2.00 g, 10.13 mmol) in anhydrous THF (25 mL) to −78° C. and add t-BuLi (1.7M in pentane, 5.9 mL, 10.13 mmol). Stir the solution 15 minutes, then warm to 0° C. Add a solution of zinc chloride (1.0 M in diethyl ether, 10.1 mL, 10.13 mmol) dropwise and allow the resulting solution to warm to ambient temperature. Cannulate this solution into a solution Preparation 14 (2.04 g, 6.75 mmol) and tetrakis(triphenylphosphine)Pd(0) (0.40 g, 0.34 mmol) in anhydrous THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield Preparation 20 (2.13 g, 90%) as a colorless oil. $^1$H NMR (CDCl$_3$): 6.98 (d, J=9.0, 1H), 6.85 (dd, J=3.1, 9.0, 1H), 6.65 (d, J=3.1, 1H), 5.10 (s, 4H), 3.45 (s, 3H), 3.44 (s, 3H), 3.38 (s, 3H), 2.56–2.50 (m, 4H), 1.84–1.80 (m, 2H), 1.65–1.60 (m, 4H). MS calcd 350.1; MS (M+1) 351.1.

Preparation 21

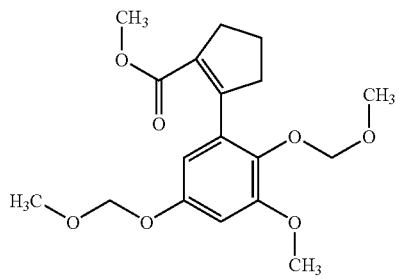

Cool a solution of Preparation 9 (2.18 g, 9.56 mmol) in anhydrous THF (40 mL) to −78° C. and add t-BuLi (1.7M in pentane, 6.2 mL, 10.52 mmol). Stir the solution 15 minutes, then warm to 0° C. Add a solution of zinc chloride (1.0 M in diethyl ether, 9.6 mL, 9.56 mmol) dropwise and allow the resulting solution to warm to ambient temperature. Cannulate this solution into a solution of Preparation 13 (2.62 g, 9.56 mmol) and tetrakis(triphenylphosphine)Pd(0) (0.55 g, 0.48 mmol) in anhydrous THF (40 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield Preparation 21 (0.62 g, 18%) as a colorless oil. $^1$H NMR (CDCl$_3$): 6.57 (d, J=2.7, 1H), 6.40 (d, J=2.7, 1H), 5.11 (s, 2H), 4.89 (s, 2H), 3.81 (s, 3H), 3.58 (S, 3H), 3.47, (s, 3H), 3.44 (s, 3H), 2.83–2.77 (m, 4H), 2.03–1.96 (m, 2H). MS calcd 352.1; MS (M+1) 353.1.

Preparation 22

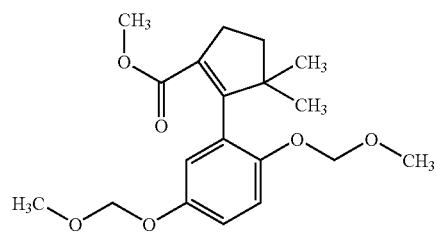

Cool a solution of Preparation 1 (1.13 g, 5.71 mmol) in anhydrous THF (40 mL) to −78° C. and add t-BuLi (1.7M in pentane, 3.4 mL, 5.71 mmol). Stir the solution 15 minutes, then warm to 0° C. Add a solution of zinc chloride (1.0 M in diethyl ether, 5.7 mL, 5.71 mmol) dropwise and allow the resulting solution to warm to ambient temperature. Cannulate this solution into a solution of Preparation 15 (1.15 g, 3.80 mmol) and tetrakis(triphenylphosphine)Pd(0) (0.55 g, 0.48 mmol) in anhydrous THF (40 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 15% ethyl acetate/hexane to yield Preparation 22 (0.42 g, 32%) as a colorless oil. $^1$H NMR (CDCl$_3$): 7.05 (d, J=9.0, 1H), 6.92 (dd, J=3.1, 9.0, 1H), 6.62 (d, J=3.1, 1H), 5.11 (S, 2H), 5.01 (s, 2H), 3.49 (s, 3H), 3.46 (s, 3H), 3.40 (s, 3H), 2.70 (t, J=7.0, 7.4, 2H), 1.86 (t, J=7.4, 7.0, 2H), 1.59 (bs, 6H). MS calcd 350.1; MS (M+1) 351.1.

Preparation 23

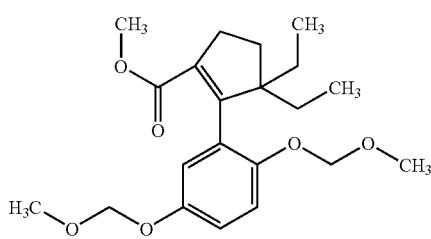

Cool a solution of Preparation 1 (3.64 g, 18.38 mmol) in anhydrous THF (50 mL) to −78° C. and add t-BuLi (1.7M in pentane, 3.4 mL, 5.71 mmol). Stir the solution 15 minutes, then warm to 0° C. Add a solution of zinc chloride (1.0 M in diethyl ether, 10.8 mL, 18.38 mmol) dropwise and allow the resulting solution to warm to ambient temperature. Cannulate this solution into a solution of Preparation 16 (3.96 g, 12.25 mmol) and tetrakis(triphenylphosphine)Pd(0) (0.71 g, 0.61 mmol) in anhydrous THF (50 mL) and heat the resulting solution to 50 C for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 15% ethyl acetate/hexane to yield Preparation 23 (3.30 g, 84%) as a colorless oil. $^1$H NMR (CDCl$_3$): 7.05 (d, J=9.0, 1H), 6.89 (dd, J=3.1, 9.0, 1H), 6.62 (d, J=2.7, 1H), 5.11 (s, 2H), 5.00 (s, 2H), 3.49 (s, 3H), 3.46 (s, 3H), 3.40 (s, 3H), 2.65 (bt, J=7.8, 7.0, 2H), 1.87 (t, J=7.8, 7.4, 2H), 1.45–1.38 (m, 4H), 0.90–0.82 (m, 6H). MS calcd 378.1; MS (M+1) 379.1.

Preparation 24

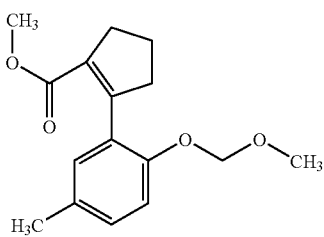

Cool a solution of Preparation 4 (2.43 g, 10.51 mmol) in anhydrous THF (25 mL) to −78° C. and add s-BuLi (1.3M in cyclohexane, 8.9 mL, 11.56 mmol). Stir the solution 15 minutes, then warm to 0° C. Add a solution of zinc chloride (1.0 M in diethyl ether, 10.51 mL, 10.51 mmol) dropwise and allow the resulting solution to warm to ambient temperature. Cannulate this solution into a solution of Preparation 13 (2.88 g, 10.51 mmol) and tetrakis(triphenylphosphine)Pd(0) (0.60 g, 0.52 mmol) in THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield Preparation 24 (1.07 g, 26%) as a pale yellow oil. $^1$H NMR (CDCl$_3$): 7.05 (bs, 2H), 6.95 (bs, 1H), 5.10 (s, 2H), 3.59 (s, 3H), 3.48 (s, 3H), 2.85 (t, J=7.0, 7.0, 4H), 2.32 (s, 3H), 2.06–1.99 (m, 2H). MS calcd 276.1; MS (M+1) 277.1.

Preparation 25

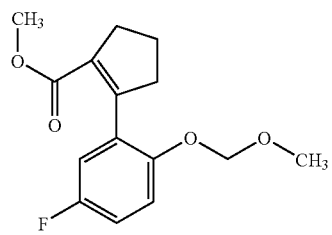

Cool a solution of Preparation 5 (2.60 g, 11.06 mmol) in anhydrous THF (25 mL) to −78° C. and add s-BuLi (1.3M in cyclohexane, 9.3 mL, 12.16 mmol). Stir the solution 15 minutes, then warm to 0° C. Add a solution of zinc chloride (1.0 M in diethyl ether, 11.0 mL, 11.06 mmol) dropwise and allow the resulting solution to warm to ambient temperature. Cannulate this solution into a solution of Preparation 13 (3.03 g, 11.06 mmol) and tetrakis(triphenylphosphine)Pd(0) (0.63 g, 0.50 mmol) in THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 15% ethyl acetate/hexane to yield Preparation 25 (1.49 g, 48%) as a pale yellow oil. $^1$H NMR (CDCl$_3$): 7.07–7.04 (m, 1H), 6.93–6.90 (m, 1H), 6.82 (dd, J=3.1, 9.0, 1H), 5.05 (s, 2H), 3.56 (s, 3H), 3.42 (s, 3H), 2.82–2.78 (m, 4H), 2.03–1.96 (m, 2H). MS calcd 280.1; MS (M+1) 281.1.

Preparation 26

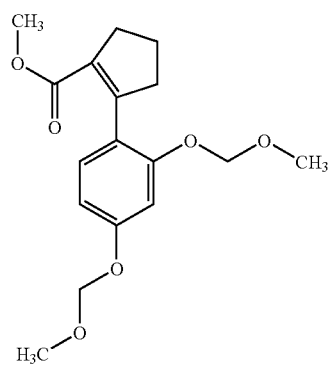

Cool a solution of Preparation 7 (2.46 g, 8.88 mmol) in anhydrous THF (25 mL) to −78° C. and add s-BuLi (1.3M in cyclohexane, 6.8 mL, 8.88 mmol). Stir the solution 15 minutes, then warm to 0° C. Add a solution of zinc chloride (1.0 M in diethyl ether, 8.9 mL, 8.88 mmol) dropwise and allow the resulting solution to warm to ambient temperature. Cannulate this solution into a solution of Preparation 13 (1.60 g, 5.86 mmol) and tetrakis(triphenylphosphine)Pd(0) (0.51 g, 0.44 mmol) in THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield Preparation 26 (1.20 g, 42%) as a colorless oil. $^1$H NMR (CDCl$_3$): 7.05 (d, J=8.6, 1H), 6.81 (d, J=2.0, 1H), 6.69 (dd, J=2.3, 8.6, 1H), 5.15 (s, 2H), 5.09 (s, 2H), 3.58 (s, 3H), 3.48 (s, 3H), 3.43 (s, 3H), 2.79 (t, J=7.0, 7.4, 4H), 2.04–1.95 (m, 2H). MS calcd 322.2; MS (M+1) 323.1.

Preparation 27

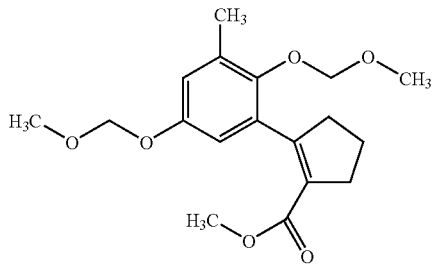

Cool a solution of Preparation 12 (1.24 g, 4.26 mmol) in anhydrous THF (20 mL) to −78° C. and add s-BuLi (1.3M in cyclohexane, 3.3 mL, 4.26 mmol). Stir the solution 15 minutes, then warm to 0° C. Add a solution of zinc chloride (1.0 M in diethyl ether, 4.3 mL, 4.26 mmol) dropwise and allow the resulting solution to warm to ambient temperature. Cannulate this solution into a solution of Preparation 13 (1.17 g, 4.26 mmol) and tetrakis(triphenylphosphine)Pd(0) (0.24 g, 0.21 mmol) in THF (20 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield Preparation 27 (0.54 g, 38%) as a colorless oil. $^1$H NMR (CDCl$_3$): 6.80 (d, J=2.4, 11H), 6.61 (d, J=2.3, 1H), 5.09 (s, 2H), 4.79 (s, 2H), 3.57 (s, 3H), 3.48 (s, 3H), 3.46 (s, 3H), 2.83–2.76 (m, 4H), 2.29 (s, 3H), 2.02–1.96 (m, 2H). MS calcd 336.2; MS (M+1) 337.2.

Preparation 28

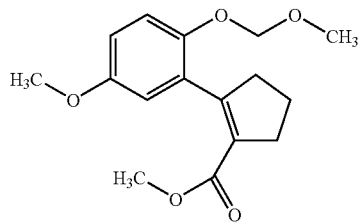

Cool a solution of Preparation 10 (2.00 g, 11.90 mmol) in anhydrous THF (20 mL) to −78° C. and add s-BuLi (1.3M in cyclohexane, 7.7 mL, 13.09 mmol). Stir the solution 15 minutes, then warm to 0° C. Add a solution of zinc chloride (1.0 M in diethyl ether, 11.9 mL, 11.90 mmol) dropwise and allow the resulting solution to warm to ambient temperature. Cannulate this solution into a solution of Preparation 13 (3.26 g, 11.90 mmol) and tetrakis(triphenylphosphine)Pd(0) (0.69 g, 0.58 mmol) in THF (20 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield the title compound (1.28 g, 38%) as a colorless oil, which is a mixture of regioisomers by $^1$H NMR. MS calcd 292.1; MS (M+1) 293.1.

Preparation 29

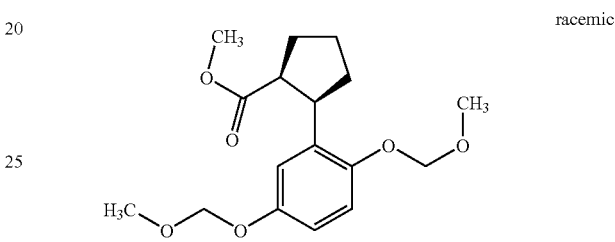

To a suspension of 5% palladium on carbon (0.27 g) in methanol (15 mL) add a solution of Preparation 17 (0.27 g, 0.84 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 30% ethyl acetate/hexane to yield Preparation 29 (0.20 g, 75%) as a clear oil. $^1$H NMR (CDCl$_3$): 6.98 (d, J=8.6, 1H), 6.86 (d, J=3.1, 1H), 6.81 (dd, J=3.1, 9.0, 1H), 5.1 (s, 2H), 5.08 (s, 2H), 3.64–3.59 (m, 1H), 3.50 (s, 3H), 3.45 (s, 3H), 3.39–3.30 (m, 1H), 3.19 (s, 3H), 2.12–1.98 (m, 4H), 1.93–1.82 (m, 1H), 1.72–1.63 (m, 1H). MS calcd 324.2; MS (M+1) 325.2.

Preparation 30

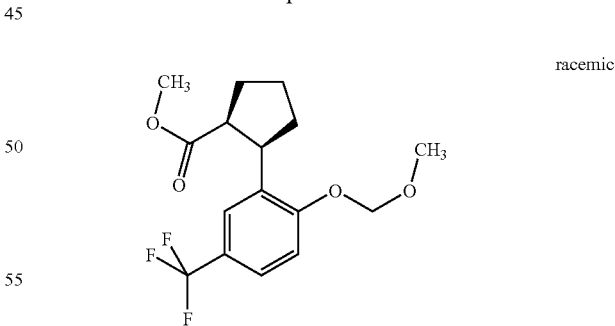

To a suspension of 5% palladium on carbon (0.19 g) in methanol (50 mL)/triethylamine (1.0 mL) add a solution of the compound of Preparation 18 (1.51 g, 4.58 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 30% ethyl acetate/hexane to yield Preparation 30 (0.95 g, 63%) as a clear oil. $^1$H NMR (CDCl$_3$): 7.42 (m, 2H), 7.15 (d, J=9.0, 1H), 5.26 (s, 2H), 3.65–3.62 (m, 1H), 3.51 (s, 3H), 3.35–3.31 (m, 1H), 3.15 (s, 3H), 2.16–2.00 (m, 4H), 1.90–1.86 (m, 1H), 1.70–1.68 (m, 1H). MS calcd 332.1; MS (M+1) 333.1.

Preparation 31

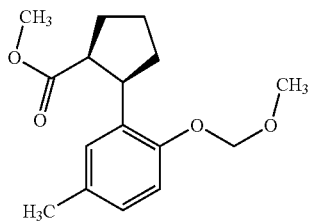

racemic

To a suspension of 5% palladium on carbon (0.13 g) in methanol (50 mL)/triethylamine (1.0 mL) add a solution of Preparation 24 (1.07 g, 3.88 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 30% ethyl acetate/hexane to yield Preparation 31 (0.72 g, 67%) as a clear oil. $^1$H NMR (CDCl$_3$): 6.96–6.93 (m, 3H), 5.17 (s, 2H), 3.67–3.60 (m, 1H), 3.50 (s, 3H), 3.34–3.28 (m, 1H), 3.15 (s, 3H), 2.25 (s, 3H), 2.15–1.99 (m, 4H), 1.90–1.83 (m, 1H), 1.70–1.63 (m, 1H). MS calcd 294.1; MS (M+1) 295.1.

Preparation 32

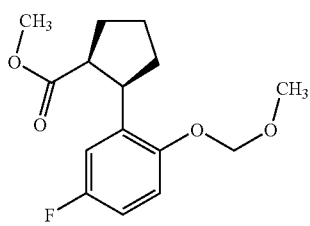

racemic

To a suspension of 5% palladium on carbon (0.24 g) in methanol (50 mL)/triethylamine (1.0 mL) add a solution of Preparation 25 (1.31 g, 4.68 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 30% ethyl acetate/hexane to yield Preparation 32 (1.01 g, 77%) as a clear oil. MS calcd 282.1; MS (M+1) 283.1.

Preparation 33

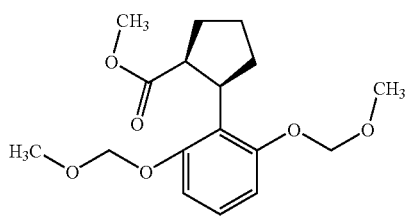

racemic

To a suspension of 5% palladium on carbon (0.34 g) in methanol (50 mL) add a solution of Preparation 19 (1.70 g, 5.28 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 30% ethyl acetate/hexane to yield Preparation 33 (0.99 g, 58%) as a clear oil. $^1$H NMR (CDCl$_3$): 7.05 (t, J=8.6, 8.2, 1H), 6.78 (d, J=8.2, 2H), 5.11 (dd, J=6.6, 18.4, 4H), 4.18–4.11 (m, 1H), 3.49 (s, 6H), 3.21 (s, 3H), 3.15–3.08 (m, 1H), 2.28–2.19 (m, 2H), 2.03–1.89 (m, 3H), 1.62–1.50 (m, 1H). MS calcd 324.2; MS (M+1) 325.2.

Preparation 34

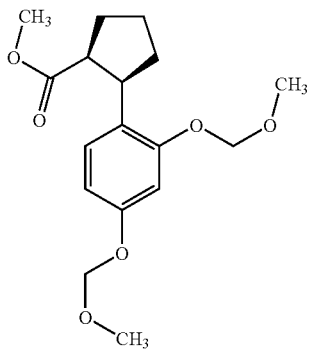

racemic

To a suspension of 5% palladium on carbon (0.60 g) in methanol (25 mL) add a solution of Preparation 26 (1.20 g, 3.73 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield Preparation 34 (0.82 g, 68%) as a clear oil. $^1$H NMR (CDCl$_3$): 7.06 (d, J=8.6, 1H), 6.77 (d, J=2.3, 1H), 6.60 (dd, J=2.4, 8.6, 1H), 5.20 (s, 2H), 5.14 (dd, J=6.6, 9.7, 2H), 3.61–3.54 (m, 1H), 3.50 (s, 6H), 3.45 (s, 3H), 3.31–3.26 (m, 1H), 2.16–1.94 (m, 4H), 1.86–1.80 (m, 1H), 1.71–1.60 (m, 1H). MS calcd 324.2; MS (M+1) 325.2.

Preparation 35

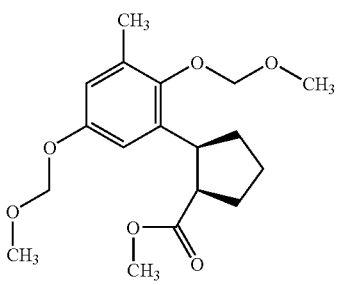

racemic

To a suspension of 5% palladium on carbon (0.25 g) in methanol (25 mL) add a solution Preparation 27 (0.54 g, 1.61 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield Preparation 35 (0.49 g, 89%) as a clear oil. $^1$H NMR (CDCl$_3$): 6.69 (d, J=2.8, 1H), 6.65 (d, J=3.1, 1H), 5.04 (m, 2H), 4.93 (dd, J=5.9, 16.0, 2H), 3.73–3.67 (m, 1H), 3.57 (s, 3H), 3.42 (s, 3H), 3.25–3.19 (m, 4H), 2.25 (s, 3H), 2.17–2.12 (m, 1H), 2.05–1.85 (m, 4H), 1.70–1.60 (m, 1H). MS calcd 338.2; MS (M+1) 339.2.

Preparation 36

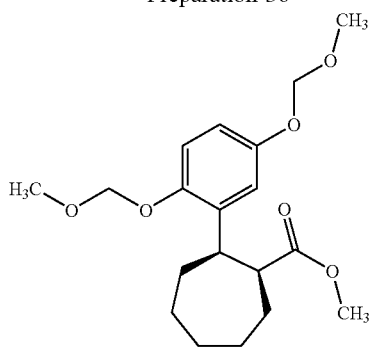

racemic

To a suspension of 5% palladium on carbon (0.38 g) in methanol (35 mL) add a solution of Preparation 20 (0.75 g, 2.14 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield Preparation 36 (0.63 g, 84%) as a clear oil. $^1$H NMR (CDCl$_3$): 6.95 (d, J=9.0, 1H), 6.85 (d, J=3.1, 1H), 6.79 (dd, J=3.1, 9.0, 1H), 5.15 (s, 2H), 5.13–5.05 (m, 2H), 3.56–3.51 (m, 1H), 3.50(s, 3H), 3.45 (s, 3H), 3.30 (s, 3H), 3.08–3.04 (m, 1H), 2.23–2.17 (m, 1H), 2.04–1.80 (m, 6H), 1.55–1.40 (m, 3H). MS calcd 352.2; MS (M+1) 353.2.

Preparation 37

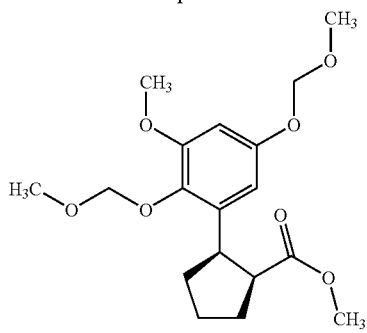

racemic

To a suspension of 5% palladium on carbon (0.08 g) in methanol (50 mL)/triethylamine (1.0 mL) add a solution of Preparation 21 (0.62 g, 1.76 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield Preparation 37 (0.50 g, 81%) as a clear oil. $^1$H NMR (CDCl$_3$): 6.50 (d, J=2.7, 1H), 6.44 (d, J=2.7, 1H), 5.14–5.05 (m, 4H), 3.80 (m, 4H), 3.58 (s, 3H), 3.46 (s, 3H), 3.25 (m, 4H), 2.15–2.09 (m, 1H), 2.07–1.90 (m, 4H), 1.72–1.64 (m, 1H). MS calcd 354.1; MS (M+1) 355.1.

Preparation 38

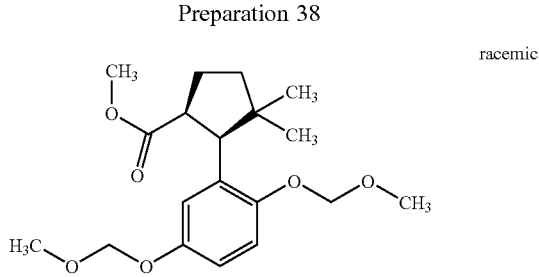

racemic

To a suspension of 5% palladium on carbon (0.05 g) in methanol (50 mL)/triethylamine (1.0 mL) add a solution of Preparation 22 (0.42 g, 1.19 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield Preparation 38 (0.16 g, 38%) as a clear oil. $^1$H NMR (CDCl$_3$): 7.00 (d, J=8.2, 0.5H), 6.94 (d, J=7.8, 0.5H), 6.84–6.75 (m, 1.5H), 6.67 (d, J=3.1, 0.5H), 5.12–5.01 (m, 4H), 3.77 (d, J=9.0, 0.5H), 3.64 (d, J=11.3, 0.5H), 3.52 (s, 1.5H), 3.49 (s, 1.5H), 3.48–3.43 (s, 4.5H), 3.35 (s, 1.5H), 2.55–2.42 (m, 0.5H), 2.17–2.02 (m, 1H), 1.95–1.88 (m, 0.5H), 1.81–1.75 (m, 1H), 1.69–1.60 (m, 0.5H), 1.55–1.50 (m, 0.5H), 1.15 (s, 1.5H), 1.01 (s, 1.5H), 0.78 (s, 3H). MS calcd 352.2; MS (M+1) 353.2.

Preparation 39

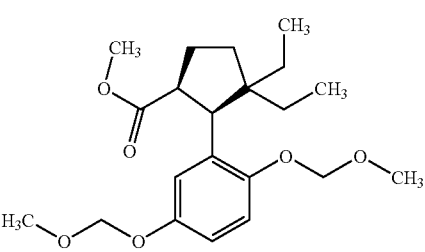

racemic

To a suspension of 5% palladium on carbon (0.58 g) in methanol (50 mL)/triethylamine (1.0 mL) add a solution of Preparation 23 (1.25 g, 3.89 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 15% ethyl acetate/hexane to yield Preparation 39 (0.89 g, 72%) as a clear oil. MS calcd 380.2; MS (M+1) 381.2.

Preparation 40

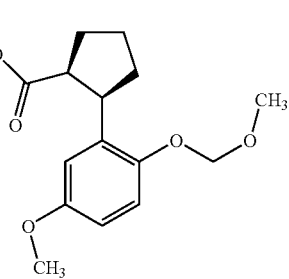

racemic

To a suspension of 5% palladium on carbon (0.15 g) in methanol (50 mL)/triethylamine (1.0 mL) add a solution of Preparation 28 (0.58 g, 1.80 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 15% ethyl acetate/hexane to yield Preparation 40 (0.25 g, 43%) as a clear oil. MS calcd 294.1; MS (M+1) 295.1.

Preparation 41

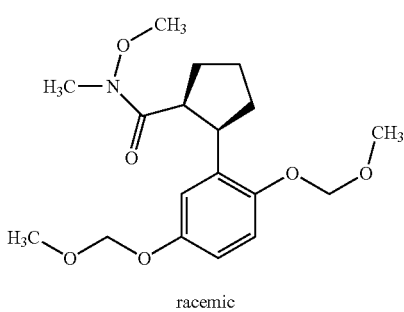

racemic

This preparation follows that in Tet. Letters 36, 31, 1995, 5461–5464. Cool a suspension of Preparation 29 (0.50 g, 1.54 mmol) and N,O-dimethylhydroxylamine hydrochloride (0.23 g, 2.31 mmol) in anhydrous THF (25 mL) to −10° C. in an ice/acetone bath, add isopropyl magnesium chloride (2.0M, 2.3 mL, 4.62 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 41 (0.49 g, 90%) as a clear oil, which is used without further characterization.

Preparation 42

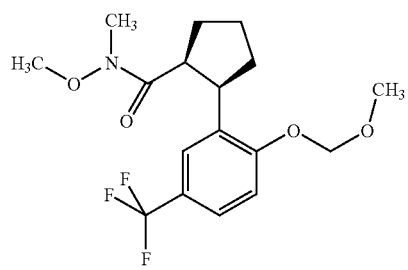

racemic

Cool a suspension of Preparation 30 (0.95 g, 2.86 mmol) and N,O-dimethylhydroxylamine hydrochloride (0.42 g, 4.29 mmol) in anhydrous THF (40 mL) to −10° C. in an ice/acetone bath, add isopropyl magnesium chloride (2.0M, 4.3 mL, 8.58 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 42 (0.86 g, 83%) as a clear oil, which is used without further characterization.

Preparation 43

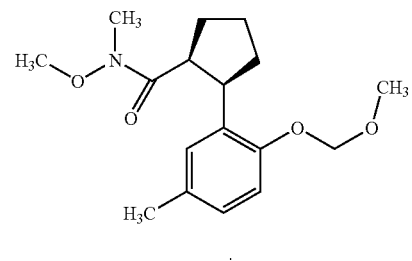

racemic

Cool a suspension of Preparation 31 (0.71 g, 2.55 mmol) and N,O-dimethylhydroxylamine hydrochloride (0.37 g, 3.83 mmol) in anhydrous THF (40 mL) to −10° C. in an ice/acetone bath, add isopropyl magnesium chloride (2.0M, 2.5 mL, 5.10 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 43 (0.36 g, 46%) as a clear oil, which is used without further characterization.

Preparation 44

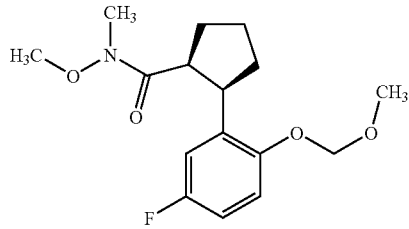

racemic

Cool a suspension of Preparation 32 (0.98 g, 3.48 mmol) and N,O-dimethylhydroxylamine hydrochloride (0.51 g, 5.22 mmol) in anhydrous THF (40 mL) to −10° C. in an ice/acetone bath, add isopropyl magnesium chloride (2.0M, 5.2 mL, 10.42 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 44 (0.61 g, 56%) as a clear oil, which is used without further characterization.

Preparation 45

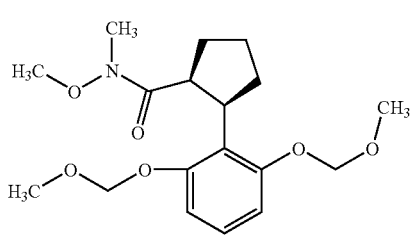

racemic

Cool a suspension of Preparation 33 (0.97 g, 2.99 mmol) and N,O-dimethylhydroxylamine hydrochloride (0.44 g, 4.49 mmol) in anhydrous THF (40 mL) to −10° C. in an ice/acetone bath, add isopropyl magnesium chloride (2.0M, 4.5 mL, 9.00 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 45 (0.71 g, 67%) as a clear oil, which is used without further characterization.

Preparation 46

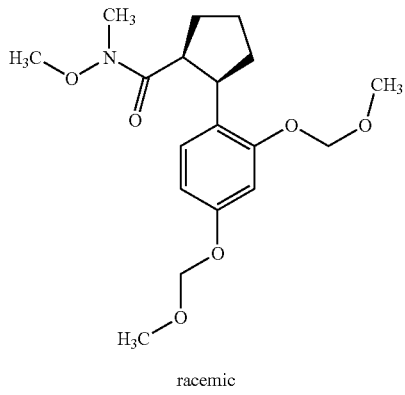

racemic

Cool a suspension of Preparation 34 (0.82 g, 2.53 mmol) and N,O-dimethylhydroxylamine hydrochloride (0.37 g, 3.80 mmol) in anhydrous THF (30 mL) to −10° C. in an ice/acetone bath, add isopropyl magnesium chloride (2.0M, 3.8 mL, 7.60 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 46 (0.80 g, 90%) as a clear oil, which is used without further characterization.

Preparation 47

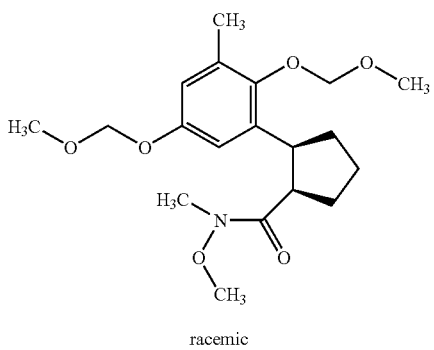

racemic

Cool a suspension of Preparation 35 (0.48 g, 1.42 mmol) and N,O-dimethylhydroxylamine hydrochloride (0.21 g, 2.13 mmol) in anhydrous THE (20 mL) to −10° C. in an ice/acetone bath, add isopropyl magnesium chloride (2.0M, 2.1 mL, 4.20 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 47 (0.46 g, 88%) as a clear oil, which is used without further characterization.

Preparation 48

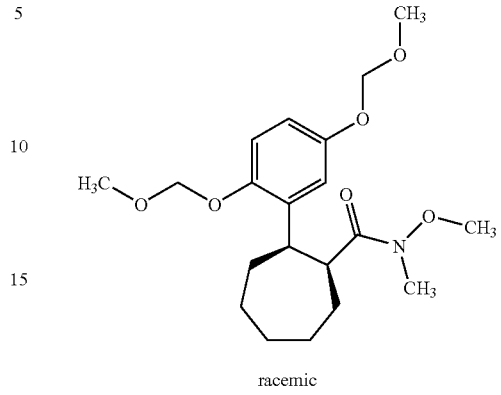

racemic

Cool a suspension of Preparation 36 (0.63 g, 2.53 mmol) and N,O-dimethylhydroxylamine hydrochloride (0.26 g, 2.68 mmol) in anhydrous THF (30 mL) to −10° C. in an ice/acetone bath, add isopropyl magnesium chloride (2.0M, 2.7 mL, 5.40 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 48 (0.54 g, 76%) as a clear oil, which is used without further characterization.

Preparation 49

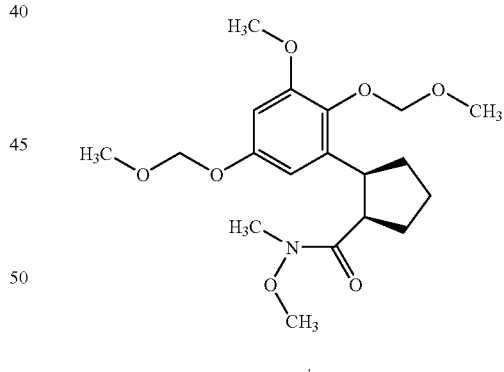

racemic

Cool a suspension of Preparation 37 (0.50 g, 1.41 mmol) and N,O-dimethylhydroxylamine hydrochloride (0.24 g, 2.12 mmol) in anhydrous THF (30 mL) to −10° C. in an ice/acetone bath, add isopropyl magnesium chloride (2.0M, 2.1 mL, 4.20 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 49 (0.31 g, 57%) as a clear oil, which is used without further characterization.

Preparation 50

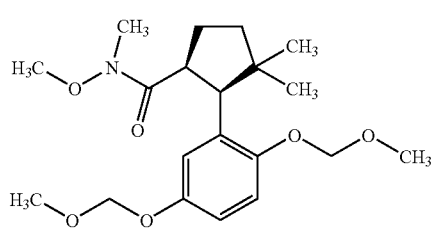

Cool a suspension of Preparation 38 (0.16 g, 0.45 mmol) and N,O-dimethylhydroxylamine hydrochloride (0.07 g, 0.68 mmol) in anhydrous THF (10 mL) to −10° C. in an ice/acetone bath, add isopropyl magnesium chloride (2.0M, 0.7 mL, 1.40 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 50 (0.15 g, 87%) as a clear oil, which is used without further characterization.

Preparation 51

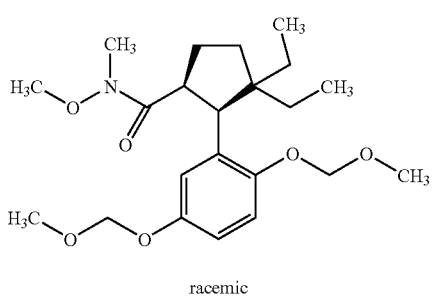

racemic

Cool a suspension of Preparation 39 (0.25 g, 0.77 mmol) and N,O-dimethylhydroxylamine hydrochloride (0.11 g, 1.16 mmol) in anhydrous THF (20 mL) to −10° C. in an ice/acetone bath, add isopropyl magnesium chloride (2.0M, 1.2 mL, 2.40 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 51 (0.20 g, 74%) as a clear oil, which is used without further characterization.

Preparation 52

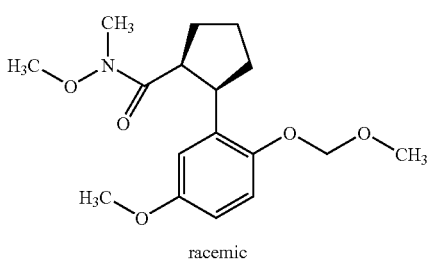

racemic

Cool a suspension of Preparation 40 (0.91 g, 3.07 mmol) and N,O-dimethylhydroxylamine hydrochloride (0.45 g, 4.64 mmol) in anhydrous THF (20 mL) to −10° C. in an ice/acetone bath, add isopropyl magnesium chloride (2.0M, 3.1 mL, 6.20 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield Preparation 52 (0.36 g, 36%) as a clear oil, which is used without further characterization.

Preparation 53

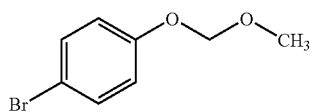

Cool a suspension of sodium hydride (60% in mineral oil, 2.54 g, 63.58 mmol) in anhydrous DMF (50 mL) under nitrogen atmosphere to 0° C. and add a solution of 4-bromophenol (10.00 g, 57.80 mmol) in anhydrous DMF (50 mL) dropwise. Add to this suspension methoxymethyl chloride (4.8 mL, 63.58 mmol) dropwise. Warm the reaction to ambient temperature and stir for one hour. Quench the reaction with water and diethyl ether. Wash the organic layer with 1N sodium hydroxide and brine. Dry the organic layer over sodium sulfate, concentrate in vacuo, and flash chromatograph with 10% ethyl acetate/hexane to yield Preparation 53 (10.42 g, 83%) as a clear oil. $^1$H NMR (CDCl$_3$): 7.38 (d, J=8.8, 2H), 6.93 (d, J=8.7, 2H), 5.14 (s, 2H), 3.43 (s, 3H).

Preparation 54

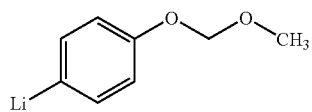

Cool a solution of Preparation 53 (3.03 g, 14.00 mmol) in anhydrous THF (40 ml) to −78° C. under nitrogen atmosphere and add s-butyllithium (1.3 M in cyclohexane, 10.7 mL, 14.00 mmol) dropwise. Stir the solution at −78° C. for 30 minutes resulting in a 0.40M solution. Use immediately, keeping temperature at −78° C.

Preparation 55

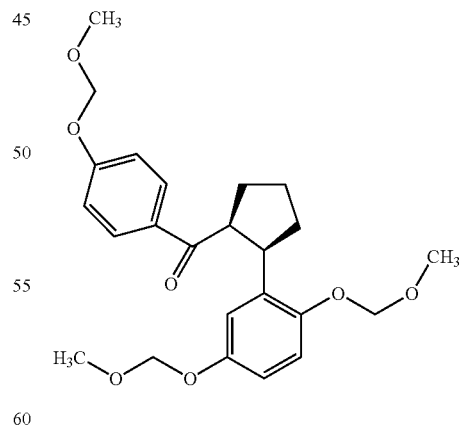

racemic

Add Preparation 54 (0.40M, 42.5 mL, 17.00 mmol) into a solution of Preparation 41 (6.00 g, 17.00 mmol) in anhydrous THF (50 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 55 (7.11 g, 97%) as a colorless foam. $^1$H NMR (CDCl$_3$): 7.61 (d, J=8.6, 2H), 6.83 (d, J=8.6, 2H), 6.76 (d, J=2.7, 1H), 6.71 (d, J=8.7, 1H), 6.60 (dd, J=2.7, 8.6 1H), 5.18 (s, 2H), 5.08–4.95 (m, 4H), 4.27–4.23 (m, 1H), 3.83–3.79 (m, 1H), 3.43 (s, 3H), 3.40 (s, 3H), 3.39 (s, 3H), 2.25–1.93 (m, 5H), 1.79–1.70 (m, 1H).

Preparation 56

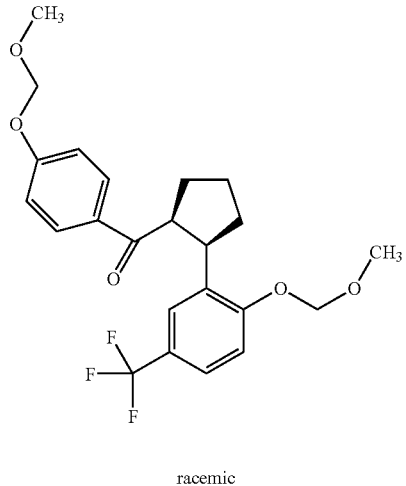

racemic

Add Preparation 54 (0.40 M, 8.9 mL, 3.57 mmol) into a solution of Preparation 42 (0.86 g, 2.38 mmol) in anhydrous THF (50 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 20% ethyl acetate/hexane to yield Preparation 56 (1.03 g, 99%) as a clear oil.

Preparation 57

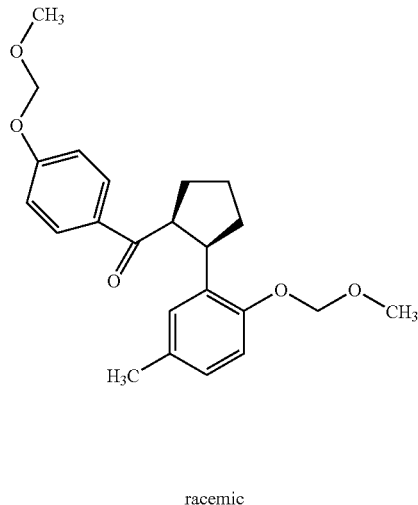

racemic

Add Preparation 54 (0.40 M, 6.1 mL, 2.34 mmol) into a solution of Preparation 43 (0.36 g, 1.17 mmol) in anhydrous THF (20 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 57 (0.41 g, 92%) as a clear oil. $^1$H NMR (CDCl$_3$): 7.61 (d, J=7.4, 2H), 6.92–6.81 (m, 3H), 6.76–6.65 (m, 2H), 5.15 (s, 2H), 4.93 (m, 2H), 4.29–4.23 (m, 1H), 3.82–3.76 (m, 1H), 3.45 (s, 3H), 3.40 (s, 3H), 2.23–1.92 (m, 8H), 1.80–1.69 (m, 1H).

Preparation 58

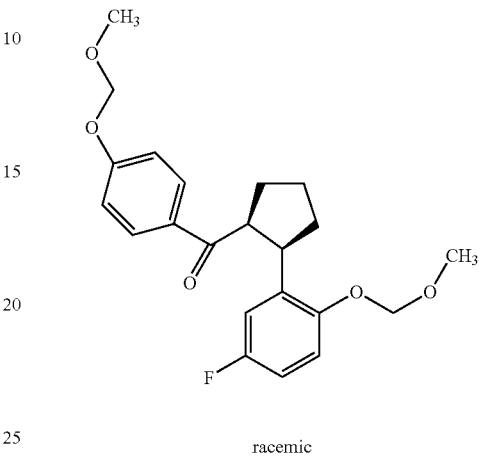

racemic

Add Preparation 54 (0.40 M, 9.8 mL, 3.92 mmol) into a solution of Preparation 44 (0.61 g, 1.96 mmol) in anhydrous THF (20 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 58 (0.59 g, 92%) as a clear oil. $^1$H NMR (CDCl$_3$): 7.61 (d, J=7.4, 2H), 6.92–6.80 (m, 3H), 6.78–0.672 (m, 1H), 6.63–6.59 (m, 1H), 5.17 (dd, J=6.6, 9.4, 2H), 4.90 (dd, J=4.5, 6.6, 2H), 4.30–4.26 (m, 1H), 3.80–3.75 (m, 1H), 3.43 (s, 3H), 3.39 (s, 3H), 2.20–1.91 (m, 5H), 1.80–1.70 (m, 1H).

Preparation 59

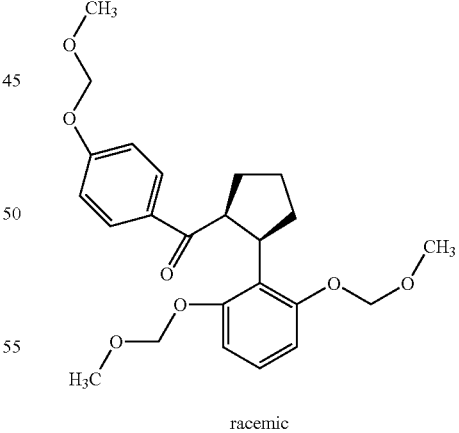

racemic

Add Preparation 54 (0.40 M, 7.5 mL, 3.03 mmol) into a solution of Preparation 45 (0.71 g, 2.01 mmol) in anhydrous THF (20 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 59 (0.80 g, 93%) as a clear oil. $^1$H NMR (CDCl$_3$): 7.55 (d, J=7.0, 2H), 6.80–6.75 (m, 3H), 6.48 (d, J=8.2, 2H), 5.15–5.06 (m, 2H), 4.96 (s, 4H), 4.39–4.31 (m, 1H), 3.80–3.76 (m, 1H), 3.46 (s, 6H), 3.40 (s, 3H), 2.55–2.45 (m, 1H), 2.30–2.20 (m, 1H), 2.15–2.05 (m, 1H), 1.96–1.85 (m, 2H), 1.70–1.60 (m, 1H). MS calcd 430.2; MS (M+1) 431.2.

Preparation 60

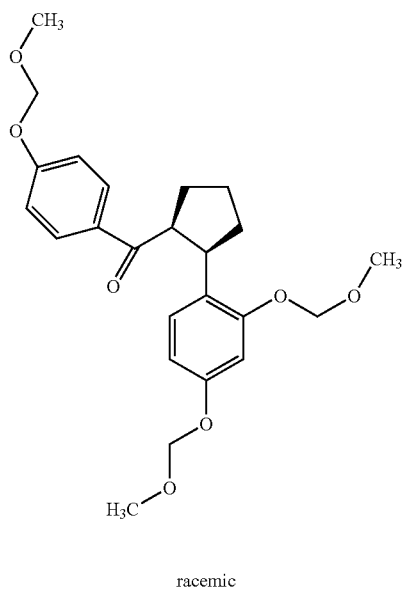

racemic

Add Preparation 54 (0.40 M, 8.5 mL, 3.40 mmol) into a solution of Preparation 46 (0.80 g, 2.26 mmol) in anhydrous THF (20 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 60 (0.87 g, 90%) as a clear oil. $^1$H NMR (CDCl$_3$): 7.61 (d, J=8.6, 2H), 6.99–6.96 (m, 1H), 6.86 (d, 8.7, 2H), 6.50–6.46 (m, 2H), 5.15 (s, 2H), 5.40–4.97 (m, 2H), 4.92 (s, 2H), 4.26–4.21 (m, 1H), 3.80–3.74 (m, 1H), 3.44 (s, 3H), 3.40 (s, 3H), 3.38 (s, 3H), 2.24–1.90 (m, 5H), 1.79–1.71 (m, 1H). MS calcd 430.2; MS (M+1) 431.2.

Preparation 61

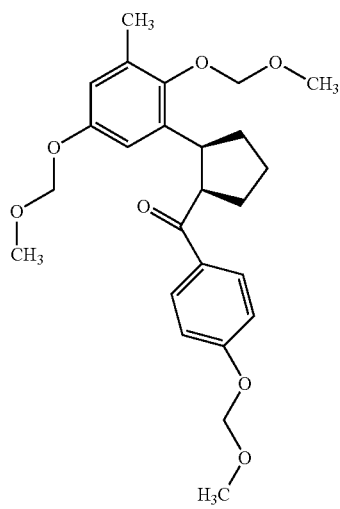

racemic

Add Preparation 54 (0.40 M, 4.7 mL, 1.88 mmol) into a solution of Preparation 47 (0.46 g, 1.25 mmol) in anhydrous THF (20 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 61 (0.43 g, 77%) as a clear oil. $^1$H NMR (CDCl$_3$): 7.61(d, J=8.6, 2H), 6.80 (d, J=9.0, 2H), 6.51 (d, J=2.7, 1H), 6.41 (d, J=2.7, 1H), 5.13 (s, 2H), 4.97–4.85 (m, 4H), 4.26–4.21 (m, 1H), 3.85–3.80 (m, 1H), 3.61 (s, 3H), 3.42 (s, 3H), 3.37 (s, 3H), 2.33–2.22 (m, 1H), 2.15–1.89 (m, 7H), 1.80–1.69 (m, 1H). MS calcd 444.2; MS (M+1) 445.2.

Preparation 62

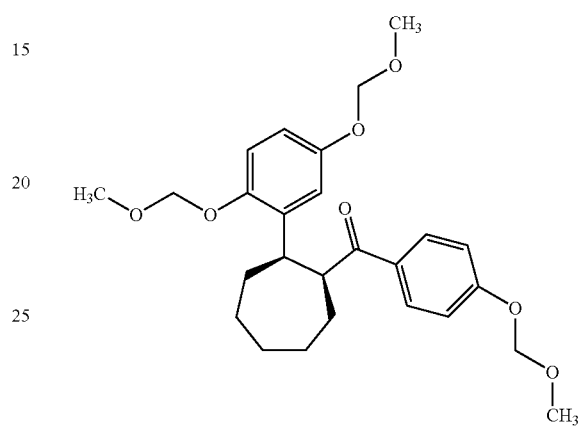

Add Preparation 54 (0.40 M, 6.8 mL, 2.74 mmol) into a solution of Preparation 48 (0.54 g, 1.37 mmol) in anhydrous THF (20 mL) at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 62 (0.25 g, 40%) as a clear oil. $^1$H NMR (CDCl$_3$): 7.55 (d, J=8.6, 2H), 6.83 (d, J=9.0, 1H), 6.76–6.72 (m, 3H), 6.57 (dd, J=3.2, 9.0, 1H), 5.14 (s, 2H), 5.00–4.92 (m, 4H), 4.10–4.03 (m, 1H), 3.70–3.63 (m, 1H), 3.45 (s, 3H), 3.43 (s, 3H), 3.38 (s, 3H), 2.38–2.30 (m, 1H), 2.10–1.82 (m, 8H), 1.55–1.45 (m, 1H).

Preparation 63 racemic

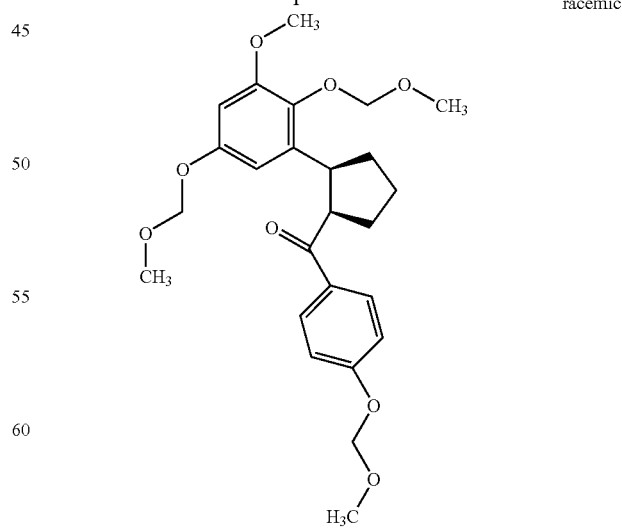

Add Preparation 54 (0.40 M, 4.0 mL, 1.62 mmol) into a solution of Preparation 49 (0.31 g, 0.81 mmol) in anhydrous THF (10 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 63 (0.12 g, 32%) as a clear oil. ¹H NMR (CDCl₃): 7.65 (d, J=8.0, 2H), 6.99–6.96 (m, 1H), 6.80 (d, J=8.0, 2H), 6.29 (d, J=2.7, 1H), 6.23 (d, J=2.7, 1H), 5.13 9S, 2H), 5.02–4.89 (m, 4H), 4.24–4.19 (m, 1H), 3.94–3.89 (m, 1H), 3.67 (s, 3H), 3.60 (s, 3H), 3.44 (s, 3H), 3.39 (s, 3H), 2.30–2.27 (m, 1H), 2.13–2.02 (m, 1H), 1.99–1.90 (m, 2H), 1.80–1.74 (m, 1H).

Preparation 64

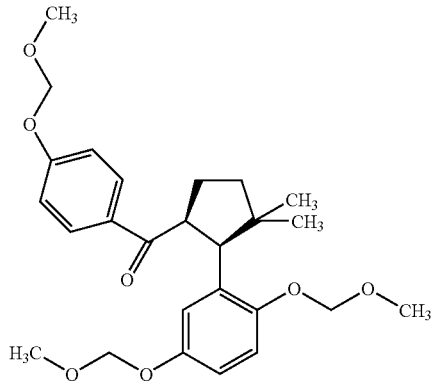

racemic

Add Preparation 54 (0.40 M, 1.5 mL, 0.59 mmol) into a solution of Preparation 50 (0.15 g, 0.39 mmol) in anhydrous THF (10 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 64 (50 mg, 28%) as a clear oil.

Preparation 65

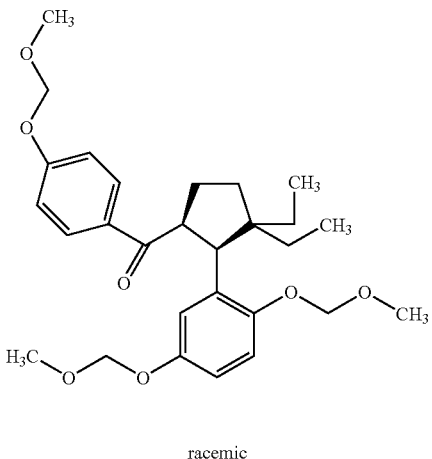

racemic

Add Preparation 54 (0.40 M, 2.1 mL, 0.85 mmol) into a solution of Preparation 51 (0.20 g, 0.57 mmol) in anhydrous THF (10 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 30% ethyl acetate/hexane to yield Preparation 65 (0.21 g, 86%) as a clear oil.

Preparation 66

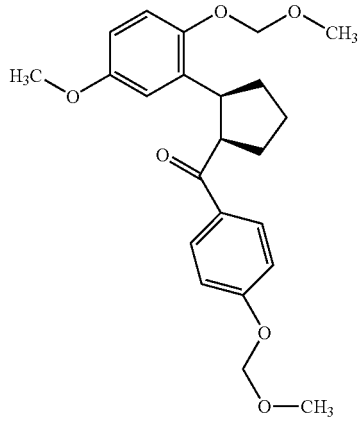

racemic

Add Preparation 52 (0.40 M, 5.5 mL, 2.22 mmol) into a solution of Preparation 50 (0.36 g, 1.11 mmol) in anhydrous THF (20 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 50% ethyl acetate/hexane to yield Preparation 66 (0.41 g, 92%) as a clear oil.

Preparation 67

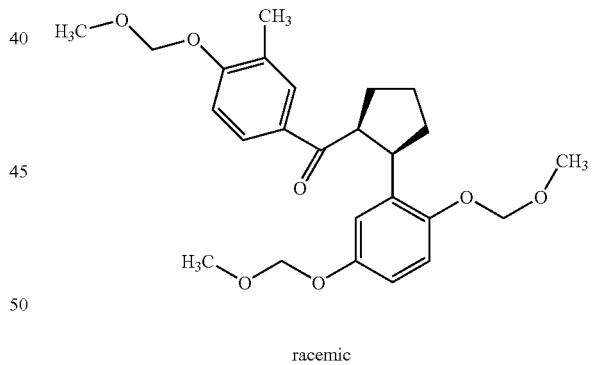

racemic

To 0.92 g (2.8 mmol) of Preparation 11 in 10 mL of THF at −78° C. was added 3.4 mL (5.6 mmol) of 1.7 M tert-butyllithium. The mixture was cannulated into 0.7 g (2.0 mmol) of Preparation 41 in 10 mL of anhydrous THF at −78° C. with magnetic stirring, and all was allowed to come to room temperature. After 5 hours, the mixture was partitioned between diethylether and saturated sodium bicarbonate aqueous. The organic layer was washed with water, saturated brine, dried over anhydrous sodium sulfate, concentrated in vacuo, and flash chromatographed on silica gel with 10% ethylacetate/hexanes to give Preparation 67 (0.51 g, 57%). The product ¹H NMR (CDCl₃) exhibited an arylmethyl singlet at 2.13 ppm, and the product was used as is.

Preparation 68

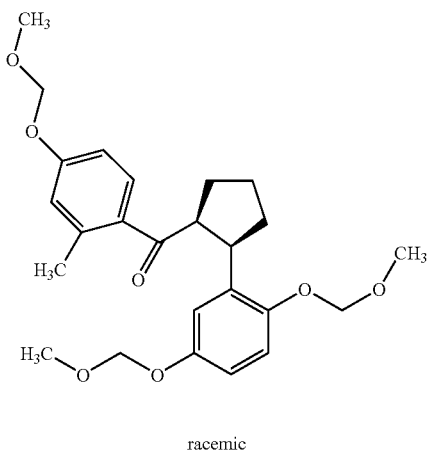

racemic

To 0.70 g (3.0 mmol) of 4-bromo-O-methoxymethyl-m-cresol in 10 mL of THF at −78° C. was added 3.6 mL (6.1 mmol) of 1.7 M tert-butyllithium. The mixture was cannulated into 0.98 g (2.77 mmol) of Preparation 41 in 10 mL of anhydrous THF at −78° C. with magnetic stirring, and all was allowed to come to room temperature. After 5 hours, the mixture was partitioned between diethylether and saturated sodium bicarbonate aqueous. The organic layer was washed with water, saturated brine, dried over anhydrous sodium sulfate, concentrated in vacuo, and flash chromatographed on silica gel with 10% ethylacetate/hexanes/0.1% triethylamine to give Preparation 68 (0.31 g, 25%). $^1$H NMR (CDCl$_3$): 7.39 (d, J=9.5, 1H), 6.83 (s, 1H), 6.70 (dd, J=9.5, 2.5, 1H), 6.68 (s, 1H), 6.61 (d, J=2.5, 1H), 5.15–4.98 (m, 4H), 4.76 (d, J=6.3, 1H), 4.65 (d, J=6.4, 1H), 4.24 (m, 1H), 3.68 (m, 1H), 3.47 (m, 1H), 3.44 (s, 3H), 3.43 (s, 3H), 3.30 (s, 3H), 2.00 (s, 3H), 2.28–1.88 (m, 4H), 1.74 (m, 1H).

EXAMPLE 1

Preparation of (⁺)-2-(4-hydroxyphenyl)-6-hydroxy-cyclopentyl[c]3,4-dihydro-2H-1-benzopyran

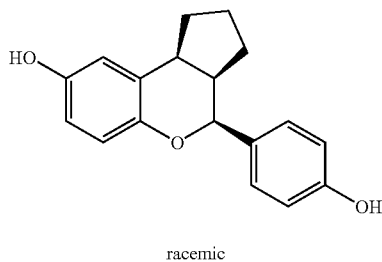

racemic

To a solution of Preparation 55 (7.10 g, 16.51 mmol) in anhydrous methanol (200 mL) add p-toluenesulfonic acid (1.04 g, 16.51 mmol) and heat the resulting solution to 50° C. for 18 hours. Cool the reaction to ambient temperature and add bromocreosol green (10 mg) and sodium cyanoborohydride (5.18 g, 82.55 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 10% diethyl ether/dichloromethane. Redissolve the product in diethyl ether (~2 mL), precipitate with dichloromethane, and filter to yield Example 1 (2.10 g, 45%) as a light purple solid. $^1$H NMR (d$_6$-DMSO): 9.28 (s, 1H), 8.80 (s, 1H), 7.20 (d, J=8.6, 2H), 6.73 (d, J=8.6, 2H), 6.61 (d, J=8.7, 1H), 6.53 (d, J=2.7, 1H), 6.45 (dd, J=2.7, 8.5, 1H), 4.92 (d, J=2.0, 1H), 3.38–3.32 (m, 1H), 2.53–2.47 (m, 1H), 2.07–2.02 (m, 1H), 1.65–1.59 (m, 1H), 1.45–1.22 (m, 4H). MS calcd. 282.1; MS (M−1) 281.1.

EXAMPLE 1A

Preparation of (2R,3R,4R)-(4-hydroxyphenyl)-6-hydroxy-cyclopentyl[c]3,4-dihydro-2H-1-benzopyran and (2S,3S,4S)-(4-hydroxyphenyl)-6-hydroxy-cyclopentyl[c]3,4-dihydro-2H-1-benzopyran

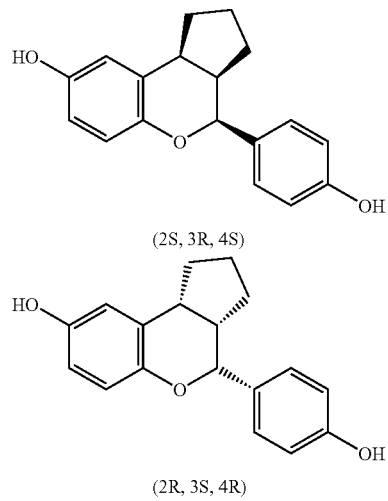

(2S, 3R, 4S)

(2R, 3S, 4R)

Using standard HPLC equipment, chromatograph the product of Example 1 (3.51 g, Chiralpak AD 8×32 cm column, 80% Heptane/isopropyl alcohol eluent, 350 mL/min, 252 nm). Concentration of pure fractions yields (S,S,S) (1.67 g, 99.9% ee, 6.9 min.) and (R, R, R) (1.71 g, 98.9% ee, 9.3 min.) as white foams.

EXAMPLE 2

Preparation of (⁺)-2-(4-hydroxyphenyl)-6-trifluoromethyl-cyclopentyl[c]3,4-dihydro-2H-1-benzopyran

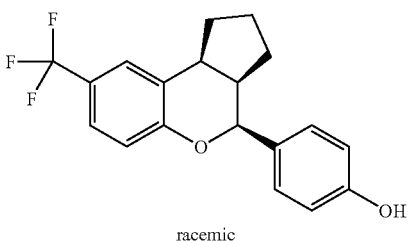

racemic

To a solution of Preparation 56 (1.03 g, 2.35 mmol) in anhydrous methanol (40 mL) add p-toluenesulfonic acid (0.11 g, 1.76 mmol) and heat the resulting solution to 50° C. for 18 hours. Cool the reaction to ambient temperature and add bromocreosol green (10 mg) and sodium cyanoborohydride (0.74 g, 11.75 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 20% ethyl acetate/hexane to yield Example 2 (0.38 g, 48%) as a light pink foam. $^1$H NMR (d$_6$-DMSO): 9.37 (s, 1H), 7.54 (d, J=1.9, 1H), 7.40 (dd, J=1.9, 8.6, 1H), 7.24 (d, J=8.2, 2H), 7.00 (d, J=8.6, 1H), 6.74 (d, J=8.2, 2H), 5.17 (d, J=2.0, 1H), 3.53 (t, J=7.4, 6.6, 1H), 2.65–2.62 (M1H), 2.18–2.10 (m, 1H), 1.78–1.72 (m, 1H), 1.46–1.29 (m, 4H). MS calcd. 334.1; MS (M−1) 333.1.

EXAMPLE 3

Preparation of ($^+$)-2-(4-hydroxyphenyl)-6-methyl-cyclopentyl[c]3,4-dihydro-2H-1-benzopyran

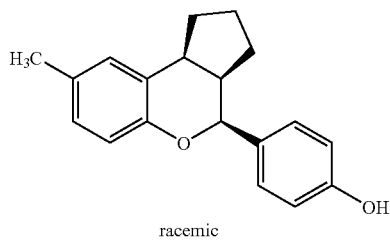
racemic

To a solution of Preparation 57 (0.40 g, 1.04 mmol) in anhydrous methanol (50 mL) add p-toluenesulfonic acid (0.05 g, 0.78 mmol) and heat the resulting solution to 50° C. for 18 hours. Cool the reaction to ambient temperature and add bromocreosol green (10 mg) and sodium cyanoborohydride (0.33 g, 5.20 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 20% ethyl acetate/hexane to yield Example 3 (0.21 g, 72%) as a light purple solid. $^1$H NMR (CDCl$_3$): 7.33 (d, J=9.0, 2H), 7.00 (d, J=1.2, 1H), 6.92 (dd, J=2.0, 8.2, 1H), 6.87–6.81 (m, 3H), 5.44 (s, 1H), 5.09 (d, J=2.0, 1H), 3.50–3.46 (m, 1H), 2.61–2.54 (m, 1H), 2.30 (s, 3H), 2.20–2.10 (m, 1H), 1.90–1.82 (m, 1H), 1.71–1.60 (m, 1H), 1.57–1.36 (m, 3H). MS calcd. 280.1; MS (M−1) 279.1.

EXAMPLE 4

Preparation of ($^+$)-2-(4-hydroxyphenyl)-6-fluoro-cyclopentyl[c]3,4-dihydro-2H-1-benzopyran

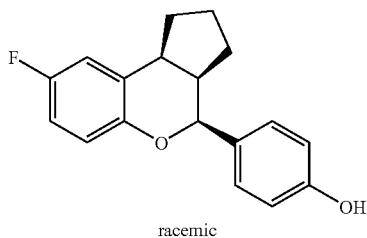
racemic

To a solution of Preparation 58 (0.59 g, 1.52 mmol) in anhydrous methanol (30 mL) add p-toluenesulfonic acid (0.07 g, 1.14 mmol) and heat the resulting solution to 50° C. for 18 hours. Cool the reaction to ambient temperature and add bromocreosol green (10 mg) and sodium cyanoborohydride (0.48 g, 7.60 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 20% ethyl acetate/hexane to yield Example 4 (0.34 g, 79%) as a light purple solid. $^1$H NMR (CDCl$_3$): 7.33 (d, J=8.6, 2H), 6.88–6.76 (m, 5H), 5.13 9s, 1H), 5.08 (d, J=2.3, 1H), 3.49–3.45 (m, 1H), 2.62–2.55 9m, 1H), 2.20–2.11 (m, 1H), 1.83–1.75 (m, 1H), 1.67–1.58 (m, 1H), 1.56–1.39 (m, 3H). MS calcd. 284.1; MS (M−1) 283.1.

EXAMPLE 5

Preparation of ($^+$)-2-(4-hydroxyphenyl)-5-hydroxy-cyclopentyl[c]3,4-dihydro-2H-1-benzopyran

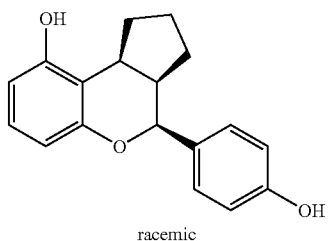
racemic

To a solution of Preparation 59 (0.80 g, 1.86 mmol) in anhydrous methanol (30 mL) add p-toluenesulfonic acid (0.09 g, 1.40 mmol) and heat the resulting solution to 50° C. for 18 hours. Cool the reaction to ambient temperature and add bromocreosol green (10 mg) and sodium cyanoborohydride (0.58 g, 9.30 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 5% diethylether/dichloromethane to yield Example 5 (0.41 g, 78%) as a light pink solid. $^1$H NMR (d$_6$-DMSO): 9.31 (s, 1H), 9.30 (s, 1H), 7.20 (d, J=8.2, 2H), 6.83 (t, J=7.4, 10.0, 1H), 6.75 (d, J=8.6, 2H), 6.39 (d, J=7.9, 1H), 6.28 (d, J=7.9, 1H), 4.87 (d, J=1.0, 1H), 3.46–3.41 (m, 1H), 2.60–2.56 (m, 1H), 2.14–2.09 (m, 1H), 1.62–1.56 (m, 1H), 1.51–1.29 (m, 4H). MS calcd. 282.1; MS (M−1) 281.1.

EXAMPLE 6

Preparation of ($^+$)-2-(4-hydroxyphenyl)-7-hydroxy-cyclopentyl[c]3,4-dihydro-2H-1-benzopyran

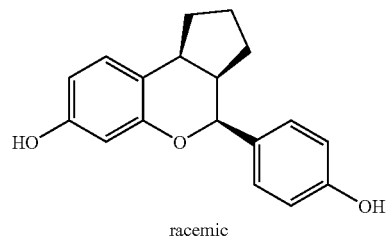
racemic

To a solution of Preparation 60 (0.86 g, 2.00 mmol) in anhydrous methanol (50 mL) add p-toluenesulfonic acid (94 mg, 1.50 mmol) and heat the resulting solution to 50° C. for 18 hours. Cool the reaction to ambient temperature and add bromocreosol green (10 mg) and sodium cyanoborohydride (0.63 g, 10.00 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 5% diethylether/dichloromethane to yield Example 6 (0.32 g, 57%) as a light yellow solid. $^1$H NMR (d$_6$-DMSO): 9.31 (s, 1H), 9.30 (s, 1H), 7.21 (d, J=8.6, 2H), 6.84–6.80 (m, 1H), 6.73 (d, J=8.6, 2H), 6.38 (d, J=7.8, 1H), 6.29 (d, J=8.2, 1H), 4.87 (s, 1H), 3.45–3.41 (m, 1H), 2.62–2.58 (m, 1H), 2.18–2.09 (m, 1H), 1.61–1.54 (m, 1H), 1.50–1.22 (m, 4H). MS calcd. 282.1; MS (M−1) 281.1.

EXAMPLE 7

Preparation of ($^+$)-2-(4-hydroxyphenyl)-6-hydroxy-8-meth 1-cyclopentyl[c]3,4-dihydro-2H-1-benzopyran

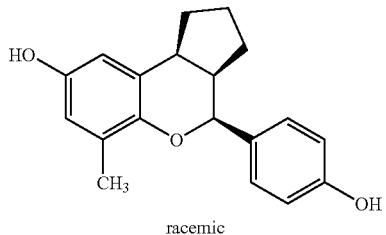

racemic

To a solution of Preparation 61 (0.15 g, 2.00 mmol) in anhydrous methanol (30 mL) add p-toluenesulfonic acid (45 mg, 0.73 mmol) and heat the resulting solution to 50° C. for 18 hours. Cool the reaction to ambient temperature and add bromocreosol green (10 mg) and sodium cyanoborohydride (0.29 g, 4.65 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 5% diethylether/dichloromethane to yield Example 7 (0.15 g, 54%) as a light yellow solid. $^1$H NMR (d$_6$-DMSO): 9.29 (s, 1H), 8.66 (s, 1H), 7.24 (d, J=8.6, 2H), 6.65 (d, J=8.2, 2H), 6.36 (s, 2H), 4.89 (s, 1H), 2.58–2.47 (m, 1H), 2.08 (s, 3H), 2.07–2.00 (m, 1H), 1.62–1.59 (m, 1H), 1.42–1.21 (m, 5H). MS calcd. 296.1; MS (M−1) 295.1.

EXAMPLE 8

Preparation of ($^+$)-2-(4-hydroxyphenyl)-6-hydroxy-cycloheptyl[c]3,4-dihydro-2H-1-benzopyran

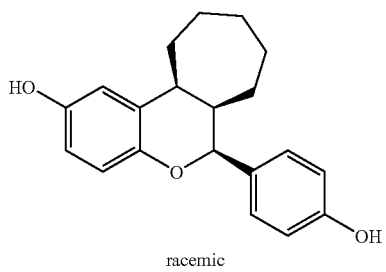

racemic

To a solution of Preparation 62 (0.25 g, 0.54 mmol) in anhydrous methanol (20 mL) add p-toluenesulfonic acid (25 mg, 0.41 mmol) and heat the resulting solution to 50° C. for 18 hours. Cool the reaction to ambient temperature and add bromocreosol green (10 mg) and sodium cyanoborohydride (0.17 g, 2.70 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, flash chromatograph with 5% diethylether/dichloromethane, and chromatograph with HPLC (YMC ODS-A 0.46×5 cm column, 5–95% gradient, 0.1% TFA/water and 0.1% TFA/acetonitrile, 3.0 mL/minute, 214 nm) to yield Example 8 (35 mg, 21%) as a light pink solid. $^1$H NMR (d$_6$-DMSO): 9.31 (s, 1H), 8.77 (s, 1H), 7.21 (d, J=8.6, 2H), 6.75 (d, J=8.6, 2H), 6.49–6.46 (m, 2H), 6.47 (dd, J=2.4, 8.7, 1H), 4.93 (s, 1H), 3.40–3.32 (m, 1H), 2.45–2.37 (m, 1H), 2.19–2.14 (m, 1H), 1.78–1.40 (m, 5H), 1.35–1.26 (m, 1H), 1.20–1.07 (m, 1H), 1.02–0.83 (m, 2H). MS calcd. 310.2; MS (M−1) 309.2.

EXAMPLE 9

Preparation of ($^+$)-2-(4-hydroxyphenyl)-6-hydroxy-8-methoxy-cyclopentyl[c]3,4-dihydro-2H-1-benzopyran

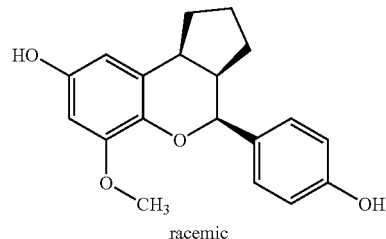

racemic

To a solution of Preparation 63 (0.12 g, 0.26 mmol) in anhydrous methanol (15 mL) add p-toluenesulfonic acid (12 mg, 0.20 mmol) and heat the resulting solution to 50° C. for 18 hours. Cool the reaction to ambient temperature and add bromocreosol green (10 mg) and sodium cyanoborohydride (0.08 g, 1.30 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 40% ethyl acetate/hexane to yield Example 9 (37 mg, 46%) as a light yellow solid. $^1$H NMR (d$_6$-acetone): 8.25 (bs, 1H), 7.90 (bs, 1H), 7.32 (, J=8.3, 2H), 6.85 (d, J=2.7, 2H), 6.30 (d, J=2.7, 1H), 6.24 (d, J=2.4, 1H), 4.94 (d, J=2.3, 1H), 3.74 (s, 3H), 3.44–3.40 (m, 1H), 2.69–2.62 (m, 1H), 2.18–2.10 (m, 1H), 1.85–1.69 (m, 1H), 1.59–1.55 (m, 1H), 1.49–1.41 (m, 2H), 1.39–1.33 (m, 1H). MS calcd. 312.2; MS (M−1) 311.2.

EXAMPLE 10

Preparation of (+)-2-(4-hydroxyphenyl)-6-hydroxy-11,11-dimethyl-cyclopentyl[c]3,4-dihydro-2H-1-benzopyran

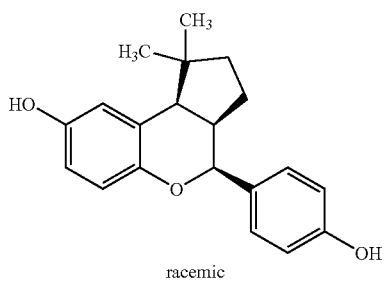

racemic

To a solution of Preparation 64 (40 mg, 0.09 mmol) in anhydrous methanol (10 mL) add p-toluenesulfonic acid (45 mg, 0.73 mmol) and heat the resulting solution to 50° C. for 18 hours. Cool the reaction to ambient temperature and add bromocreosol green (10 mg) and sodium cyanoborohydride (27 mg, 0.43 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and chromatograph using a chromatotron (1 mm plate) with 30% ethyl acetate/hexane to yield Example 10 (16 mg, 59%) as a light pink solid. $^1$H NMR ($d_6$-acetone): 8.20 (s, 1H), 7.80 (s, 1H), 7.28 (d, J=8.2, 2H), 6.84 (d, J=8.6, 2H), 6.72 (d, J=8.6, 1H), 6.64 (d, J=3.2, 1H), 6.60 (dd, J=3.1, 8.6, 1H), 4.73 (d, J=2.7, 1H), 3.04–2.98 (m, 2H), 1.64–1.59 (m, 1H), 1.43–1.37 (m, 2H), 1.25–1.20 (m, 1H), 1.19 (s, 3H), 0.53 (s, 3H). MS calcd. 310.2; MS (M−1) 309.2.

EXAMPLE 11

Preparation of (+)-2-(4-hydroxyphenyl)-6-hydroxy-11,11-diethyl-cyclopentyl[c]3,4-dihydro-2H-1-benzopyran

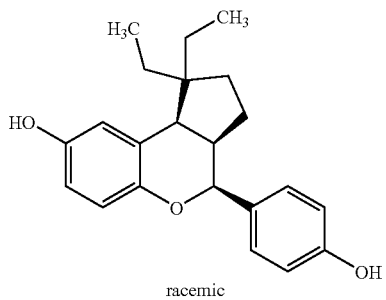

racemic

To a solution of using Preparation 65 (0.21 g, 0.57 mmol) in anhydrous methanol (10 mL) add p-toluenesulfonic acid (31 mg, 0.48 mmol) and heat the resulting solution to 50° C. for 18 hours. Cool the reaction to ambient temperature and add bromocreosol green (10 mg) and sodium cyanoborohydride (150 mg, 2.40 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and chromatograph using a chromatotron (2 mm plate) with 30% ethyl acetate/hexane to yield Example 11 (50 mg, 26%) as a light pink solid. $^1$H NMR (MeOD): 7.20 (d, J=8.2, 2H), 6.75 (d, J=8.2, 2H), 6.70 (d, J=8.2, 1H), 6.56 (d, J=2.8, 1H), 6.52 (dd, J=2.7, 8.2, 1H), 4.70 (d, J=3.5, 1H), 3.20 (d, J=10.5, 1H), 2.92–2.83 (m, 1H), 1.61–1.53 (m, 2H), 1.49–1.20 (m, 5H), 1.05–0.95 (m, 4H), 0.50 (t, J=8.8, 3H). MS calcd. 338.2; MS (M−1) 337.2.

EXAMPLE 12

Preparation of (+)-2-(4-hydroxyphenyl)-6-methoxy-cyclopentyl[c]3,4-dihydro-2H-1-benzopyran

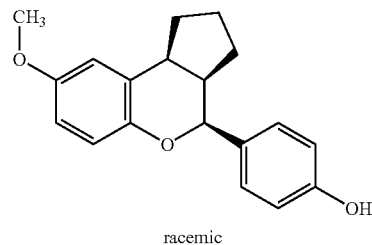

racemic

To a solution of Preparation 66 (0.40 g, 1.00 mmol) in anhydrous methanol (20 mL) add p-toluenesulfonic acid (47 mg, 0.75 mmol) and heat the resulting solution to 50° C. for 18 hours. Cool the reaction to ambient temperature and add bromocreosol green (10 mg) and sodium cyanoborohydride (0.31 g, 5.00 mmol). Add methanol saturated with HCl (gas) dropwise until yellow color is maintained. Stir the reaction one hour past the time when no more color change was observed. Quench the reaction with saturated sodium bicarbonate, add ethyl acetate, and wash the organic layer with sodium bicarbonate and brine. Dry the organic layer over sodium sulfate, concentrate in vacuo, and flash chromatograph with 40% ethyl acetate/hexane to yield Example 12 (0.15 g, 51%) as a light purple solid. $^1$H NMR (CDCl$_3$): 7.33 (d, J=8.2, 2H), 6.85–6.82 (m, 3H), 6.72–6.66 (m, 2H), 5.27 (s, 1H), 5.05 (d, J=2.0, 1H), 3.79 (s, 3H), 3.50–3.45 (m, 1H), 2.58–2.54 (m, 1H), 2.19–2.11 (m, 1H), 1.84–1.79 (m, 2H), 1.67–1.58 (m, 1H), 1.55–1.68 (m, 2H). MS calcd. 296.1; MS (M−1) 295.1.

EXAMPLE 13

Preparation of (+)-2-(4-hydroxy-3-methylphenyl)-6-hydroxy-cyclopentyl[c]3,4-dihydro-2H-1-benzopyran

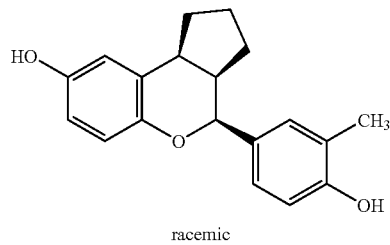

racemic

To a solution of Preparation 67 (0.51 g, 1.10 mmol) in anhydrous methanol (15 mL) under nitrogen gas bubbling to purge of oxygen was added p-toluenesulfonic acid (0.17 g, 0.86 mmol). The bubbler was removed, and the resulting solution was heated to 50° C. for 18 hours under a nitrogen atmosphere. To the mixture at ambient temperature was added bromocreosol green (~1 mg) and sodium cyanoborohydride (0.35 g, 5.50 mmol). Methanol saturated with HCl (gas) was added portionwise over time to maintain the yellow color. After no more spontaneous color change to blue was observed, the mixture was partitioned between diethylether and saturated potassium sodium tartrate aqueous. The organic layer was dried over anhydrous sodium sulfate, concentrated in vacuo, and flash chromatographed on silica gel with 3% diethylether/methylene chloride to give 0.11 g (34%) of a cis/trans mixture (3:2) of stereoisomers. Reverse phase chromatography on a C18 column with an acetonitrile/water gradient plus 0.1% TFA gave 10 mg (3%) of the cis-fused Example 13. $^1$H NMR (DMSO-d$_6$): 9.30 (s, 1H), 8.81 (s, 1H), 7.10 (s, 1H), 7.03 (d, J=8.2, 1H), 6.74 (d, J=8.2, 1H), 6.63 (d, J=8.2, 1H), 6.55 (d, J=2.8, 1H), 6.47 (dd, J=2.7, 8.2, 1H), 4.95 (s, 1H), 3.37 (m, 1H), 2.55 (m, 1H), 2.12 (s, 3H), 2.02 (m, 1H), 1.65–1.24 (m, 5H). MS calcd. 296.3; MS (M−1) 295.1.

EXAMPLE 14

Preparation of ($^+$)-2-(4-hydroxy-3-methylphenyl)-6-hydroxy-cyclopentyl[c]3,4-dihydro-2H-1-benzopyran

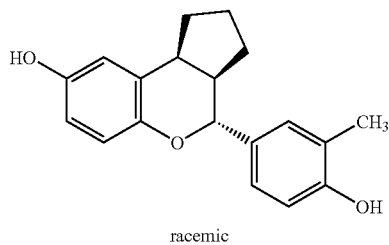

racemic

The trans-fused containing product band was re-chromatographed on a C18 reverse phase column with 40:60 acetonitrile/water to give 8.2 mg (2%) of the trams-fused Example 14. $^1$H NMR (DMSO-d6): 9.05 (s, 1H), 7.10 (s, 1H), 7.03 (d, J=8.2, 1H), 6.74 (d, J=8.2, 1H), 6.62–6.55 (m, 2H), 6.47 (dd, J=2.7, 8.2, 1H), 4.13 (d, J=11.0, 1H), 2.95 (m, 1H), 2.43 (m, 1H), 2.20 (m, 1H), 2.12 (s, 3H), 1.70–1.40 (m, 4H), 1.17 (m, 1H).

EXAMPLE 15

Preparation of ($^+$)-2-(2-methyl-4-hydroxyphenyl)-6-hydroxy-cyclopentyl[c]3,4-dihydro-2H-1-benzopyran

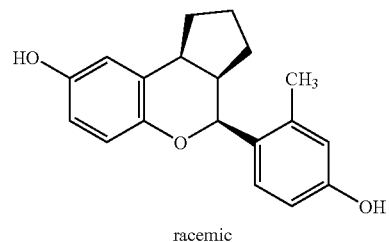

racemic

To a solution of Preparation 68 (0.31 g, 0.70 mmol) in anhydrous methanol (15 mL) under nitrogen gas bubbling to purge of oxygen was added p-toluenesulfonic acid (0.10 g, 0.52 mmol). The bubbler was removed, and the resulting solution was heated to 50° C. for 18 hours under a nitrogen atmosphere. To the mixture at ambient temperature was added bromocreosol green (~1 mg) and sodium cyanoborohydride (0.22 g, 3.5 mmol). Methanol saturated with HCl (gas) was added portionwise over time to maintain the yellow color. After no more spontaneous color change to blue was observed, the mixture was partitioned between ethylether and water. The organic layer was dried over anhydrous sodium sulfate, concentrated in vacuo, and flash chromatographed on silica gel with 3% diethylether/methylene chloride to give 0.07 g of crude product. Reverse phase chromatography on a C18 column with an acetonitrile/water gradient plus 0.1% TFA after lyophilization gave 17 mg (8%) of Example 15 as a red gum. $^1$H NMR (DMSO-d6): 9.21 (s, 1H), 8.83 (s, 1H), 7.26 (d, J=8.0, 1H), 6.60 (d, J=7.6, 2H), 6.56 (s, 2H), 6.47 (dd, J=7.6, 2.8, 2H), 5.04 (s, 1H), 3.42 (m, 1H), 2.50 (m, 1H), 2.19 (s, 3H), 2.07 (m, 1H), 1.64–1.18 (m, 5H).

Preparation 69

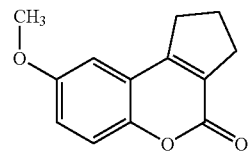

Preparations follow that in Tetrahedron, 53, 39, 1997, pp 13329–13338. Cool a solution of 4-methoxyphenol (7.5 g, 60.67 mmol) in sulfuric acid (12 mL, 121.3 mmol)/TFA (9.0 mL, 121.3 mmol) to 0° C. and add methyl 2-oxocyclopentane carboxylate (17.25 g, 121.3 mmol). Stir at ambient temperature for 48 hours. Pour into saturated sodium bicarbonate until basic, then add ethyl acetate and wash with 1 N sodium hydroxide and brine. Dry the organic layer over sodium sulfate, concentrate in vacuo, and flash chromatograph with 100% dichloromethane. Precipitate resulting crude product from dichloromethane/hexane to yield Preparation 69 (1.84 g, 17%) as a light yellow solid. $^1$H NMR (CDCl$_3$): 7.25 (d, J=7.3, 1H), 7.03 (dd, J=2.9, 8.8, 1H), 6.82 (d, J=2.9, 1H), 3.82 (s, 3H), 3.03 (t, J=5.7, 5.8, 2H), 2.90 (t, J–7.3, 8.1, 2H), 2.23–2.15 (m, 2H). MS calcd. 216.1; MS (M+1) 217.1.

Preparation 70

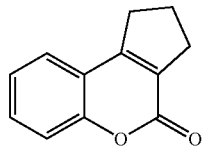

Cool a solution of phenol (5.00 g, 53.19 mmol) in 80% sulfuric acid (60 mL) to 0° C. and add methyl 2-oxocyclopentane carboxylate (18.88 g, 133.97 mmol). Stir at ambient temperature for 48 hours. Pour into saturated sodium bicarbonate until basic, then add ethyl acetate and wash with 1 N sodium hydroxide and brine. Dry the organic layer over sodium sulfate, concentrate in vacuo, and flash chromatograph with 100% dichloromethane. Precipitate resulting crude product from dichloromethane/hexane to yield Preparation 70 (1.32 g, 13%) as a white solid. $^1$H NMR (CDCl$_3$): 7.46–7.40 (m, 2H), 7.35–7.32 (m, 1H), 7.26–7.22 (m, 1H), 3.09–3.4 (m, 2H), 2.93–2.88 (m, 2H), 2.24–2.18 (m, 2H). MS calcd. 186.1; MS (M+1) 187.1.

Preparation 71

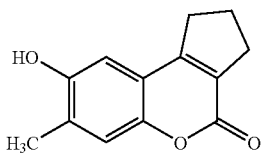

Cool a solution of methyl hydroquinone (4.09 g, 33.00 mmol) in 80% sulfuric acid (40 mL) to 0° C. and add methyl 2-oxocyclopentane carboxylate (11.70 g, 82.50 mmol). Stir at ambient temperature for 48 hours. Pour into saturated sodium bicarbonate until basic, then add ethyl acetate and wash with 1 N sodium hydroxide and brine. Dry the organic layer over sodium sulfate and concentrate in vacuo. Dissolve the crude solid in 1N NaOH, wash with diethyl ether, then precipitate out of aqueous layer with 1N HCl. Filter the mixture to yield Preparation 71 (3.10 g, 43%) as a tan solid. $^1$H NMR (d$_6$-DMSO): 9.61(s, 1H), 7.11 9s, 1H), 6.78 (s, 1H), 2.67 (t, J=6.4, 7.3, 4H), 2.15 (s, 3H), 2.08–2.01 (m, 2H). MS calcd. 216.1; MS (M+1) 217.1.

Preparation 72

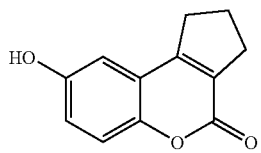

Cool a solution of hydroquinone (3.10 g, 28.17 mmol) in 80% sulfuric acid (40 mL) to 0° C. and add methyl 2-oxo-cyclopentane carboxylate (10.00 g, 70.42 mmol). Stir at ambient temperature for 9 days. Pour into ice water and filter. Dissolve solid in methanol and concentrate in vacuo. Dissolve solid in chloroform, filter hot, and concentrate in vacuo. Chromatograph filtrate with 4% methanol/chloroform to yield Preparation 72 (1.10 g, 19%) as a light yellow solid. $^1$H NMR (d$_6$-DMSO): 9.67 (s, 1H), 7.23 (d, J=8.8, 1H), 6.95 (dd, J=2.9, 8.8, 1H), 6.84 (d, J=2.4, 1H), 2.98 (t, J=6.8, 8.3, 2H), 2.71 (t, J=7.3, 7.3, 2H), 2.10–2.02 (m, 2H). MS calcd. 202.2; MS (M+1) 203.2.

Preparation 73

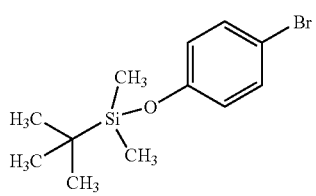

Stir a solution of 4-bromophenol (25.00 g, 144.5 mmol), t-butyldimethylsilyl chloride (23.96 g, 158.95 mmol), and imidazole (10.82 g, 158.95 mmol) in anhydrous DMF (200 mL) for 18 hours. Add diethyl ether, wash with water and brine, and dry the organic layer over sodium sulfate. Concentrate in vacuo and flash chromatograph with 10% ethyl acetate/hexane to yield Preparation 73 (40.98 g, 99%) as a clear oil. $^1$H NMR (CDCl$_3$): 7.24 (d, J=8.8, 2H), 6.73 (d, J=8.8, 2H), 0.99 (s, 9H), 0.20 (s, 6H).

Preparation 74

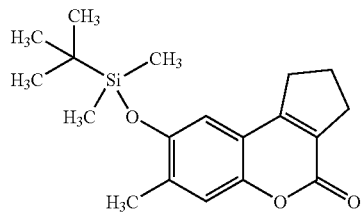

Stir a solution of Preparation 71 (2.20 g, 10.19 mmol), t-butyldimethylsilyl chloride (2.30 g, 15.28 mmol), and imidazole (1.04 g, 15.28 mmol) in anhydrous DMF (200 mL) for 18 hours. Add diethyl ether, wash with water and brine, and dry the organic layer over sodium sulfate. Concentrate in vacuo and flash chromatograph with 20% ethyl acetate/hexane to yield Preparation 74 (3.33 g, 99%) as a white solid. $^1$H NMR (CDCl$_3$): 7.16 (s, 1H), 6.75 (s, 1H), 3.04–3.00 (m, 2H), 2.98–2.90 (m, 2H), 2.29 (s, 3H), 2.25–2.20 (m, 2H), 1.04 (s, 9H), 0.24 (s, 6H).

Preparation 75

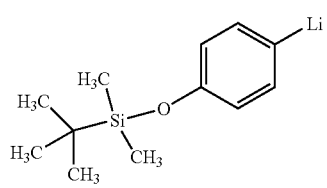

Cool a solution of Preparation 73 (2.04 g, 7.11 mmol) in anhydrous THF (25 mL) to −78° C. and add sBuLi (1.3 M in cyclohexane, 5.5 mL, 7.11 mmol) dropwise. Stir the solution for 15 minutes at −78° C., then use without further purification.

Preparation 76

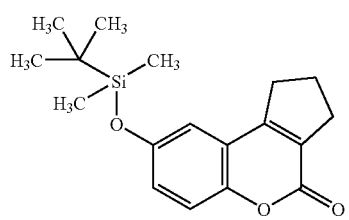

Add t-butyldimethylsilyl chloride (1.00 g, 6.68 mmol) to a stirred solution of Preparation 72 (0.90 g, 4.45 mmol) and imidazole (0.45 g, 6.68 mmol) in anhydrous DMF (15 mL). Stir the resulting solution 48 hours, then quench with saturated sodium bicarbonate. Add diethyl ether, wash with brine, dry organic layer over sodium sulfate, and concentrate in vacuo. Chromatograph the resulting crude material with 10% ethyl acetate/hexanes to yield Preparation 76 (1.01 g, 72%) as a white solid. $^1$H NMR (CDCl$_3$): 7.24 (d, J=4.4, 1H), 6.96 (dd, J=2.9, 9.3, 1H), 6.82 (d, J=2.5, 1H), 3.03 (m, 2H) 2.93 (m, 2H), 2.20 (m, 2H). MS calcd. 314; MS (M+1) 315.

Preparation 77

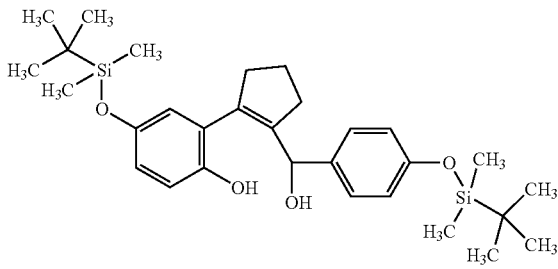

Cool a solution of Preparation 76 (0.50 g, 1.58 mmol) in anhydrous dichloromethane (30 mL) to −78° C. and add diisobutylaluminum hydride (1.0M in toluene, 1.8 mL, 1.81 mmol) and stir 3 hours. Quench with methanol (5.0 mL) and warm to ambient temperature. Add ethyl acetate and wash with bicarbonate and brine. Dry the organic layer over sodium sulfate and concentrate in vacuo. Redissolve the resulting foam in anhydrous THF (10 ml) and cool to −78° C. Add Preparation 75 (0.21 M, 22.5 mL, 4.74 mmol) and stir 10 minutes. Add 1N HCl (50 mL), warm to ambient temperature, and stir 30 minutes. Add ethyl acetate and wash with brine. Dry the organic layer over sodium sulfate and concentrated in vacuo to yield Preparation 77 (0.81 g, 100%) as a red oil. This material was used in the next step without further purification.

EXAMPLE 16

Preparation of (+)-2-(4-hydroxyphenyl)-6-hydroxy-cyclopentyl[c]3,4-dihydro-2H-1-benzopyran

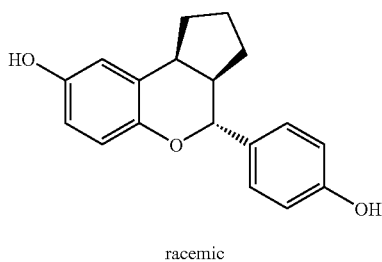

racemic

Stir a solution of Preparation 77 (0.81 g, 1.58 mmol) and tetrabutylammonium fluoride (1.0 M in THF, 6.3 mL, 6.32 mmol) in THF (20 mL) at ambient temperature for 30 minutes, then add 1N HCl (7 mL) and stir 5 minutes. Add ethyl acetate, wash with concentrated bicarbonate and brine, dry the organic layer over sodium sulfate, and concentrate in vacuo. Flash chromatograph the crude product with 5% methanol/dichloromethane. Redissolve the resulting material in methanol (10 mL), add 5% palladium on carbon (60 mg) and ammonia (2.0M in methanol, 0.25 mmol, 0.13 mL), place a hydrogen balloon on the reaction, and stir at ambient temperature overnight. Filter the reaction through celite, concentrate in vacuo, and flash chromatograph with 10% diethylether/dichloromethane to yield Example 16 (40 mg, 10%) as light pink solids. $^1$H NMR (MeOD): 7.19 (d, J=8.8, 2H), 6.75 (d, J=8.3, 2H), 6.62 (m, 2H), 6.47 (dd, J=2.9, 8.8, 1H), 4.14 (d, J=11.3, 1H), 3.00 (m, 1H), 2.48 (m, 1H), 2.28 (m, 1H), 1.70 (m, 2H), 1.56 (m, 2H), 1.28 (m, 1H). MS calcd. 282; MS (M+1) 283.

Preparation 78

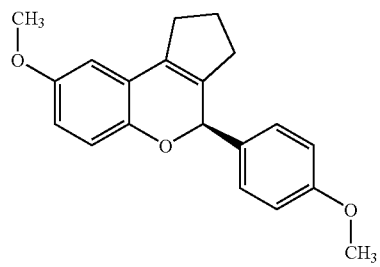

racemic

Cool a solution of Preparation 69 (0.76 g, 3.52 mmol) in anhydrous dichloromethane (60 mL) to −78° C. and add diisobutylaluminum hydride (1.0M in toluene, 3.9 mL, 3.87 mmol) and stir 2 hours. Quench with methanol and warm to ambient temperature. Add ethyl acetate and wash with bicarbonate and brine. Dry the organic layer over sodium sulfate and concentrate in vacuo. Redissolve the resulting foam in anhydrous THF (10 ml) and cool to 0° C. Add aryl griniard (0.51 M, 3.6 mL, 1.84 mmol) and stir 10 minutes. Add 1N HCl (50 mL), warm to ambient temperature, and stir 30 minutes. Add ethyl acetate and wash with brine. Dry the organic layer over sodium sulfate, concentrate in vacuo, and flash chromatograph with 50% dichloromethane/hexane to yield Preparation 78 (0.33 g, 30%) as a red oil. $^1$H NMR (CDCl$_3$): 7.33 (d, J=8.3, 2H), 6.89 (d, J=8.8, 2H), 6.80 (d, J=8.8, 1H), 6.68–6.63 (m, 2H), 5.04 (d, J=2.5, 1H), 3.80 (s, 3H), 3.75 (s, 3H), 3.47–3.43 (m, 1H), 2.60–2.54 (m, 1H), 2.14–2.09 (m, 1H), 1.82–1.76 (m, 1H), 1.67–1.57 (m, 1H), 1.50–1.30 (m, 3H).

Preparation 79

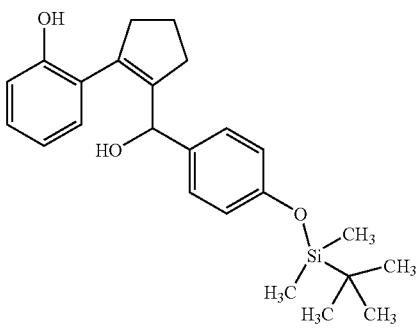

Cool a solution of Preparation 70 (0.44 g, 2.37 mmol) in anhydrous dichloromethane (40 mL) to −78° C. and add diisobutylaluminum hydride (1.0M in toluene, 2.8 mL, 2.84 mmol) and stir 2 hours. Quench with methanol and warm to ambient temperature. Add ethyl acetate and wash with bicarbonate and brine. Dry the organic layer over sodium sulfate and concentrate in vacuo. Redissolve the resulting foam in anhydrous THF (10 ml) and cool to −78° C. Add Preparation 75 (0.21 M, 35.5 mL, 7.11 mmol) and stir 10 minutes. Add 1N HCl (50 mL), warm to ambient temperature, and stir 30 minutes. Add ethyl acetate and wash with brine. Dry the organic layer over sodium sulfate and concentrated in vacuo to yield Preparation 79 (0.40 g, 43%). This material was used in the next step without further purification. $^1$H NMR (MeOD): 7.25–7.18 (m, 2H), 7.1–7.08 (m, 2H), 6.91–6.83 (m, 2H), 6.80–6.75 (m, 2H), 4.90 (m, 2H), 3.35–3.31 (m, 1H), 2.81–2.60 (m, 3H), 2.28–2.17 (m, 1H), 1.98–1.90 (m, 2H0, 1.00 (s, 9H), 0.24 (s, 6H). MS calcd. 396.2; MS (M−1) 395.4.

Preparation 80

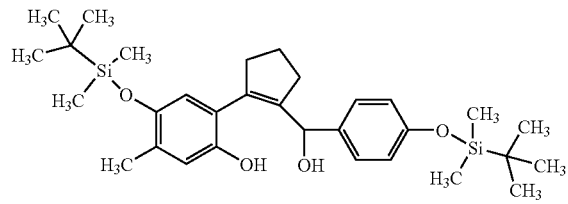

Cool a solution of Preparation 74 (1.00 g, 3.03 mmol) in anhydrous dichloromethane (60 mL) to −78° C. and add diisobutylaluminum hydride (1.0M in toluene, 3.6 mL, 3.63 mmol) and stir 2 hours. Quench with methanol and warm to ambient temperature. Add ethyl acetate and wash with bicarbonate and brine. Dry the organic layer over sodium sulfate and concentrate in vacuo. Redissolve the resulting foam in anhydrous THF (10 ml) and cool to −78° C. Add Preparation 75 (0.21 M, 45.4 mL, 9.09 mmol) and stir 10 minutes. Add 1N HCl (50 mL), warm to ambient temperature, and stir 30 minutes. Add ethyl acetate and wash with brine. Dry the organic layer over sodium sulfate and concentrated in vacuo to yield Preparation 80 (0.51 g, 99%) as a red oil. This material was used in the next step without further purification. $^1$H NMR (CDCl$_3$): 7.30 (d, J=8.2, 2H), 6.87 (d, J=8.6, 2H), 6.70 (s, 1H), 6.60 (s, 1H), 5.50 (s, 1H), 4.99 (s, 2H), 2.93–2.69 (m, 4H), 2.38–2.32 (m, 1H), 2.28 (s, 3H), 2.09–1.95 (m, 2H), 1.09 (s, 9H), 1.08 (s, 9H), 0.32 (s, 6H), 0.22 (s, 6H). MS calcd. 540.3; MS (M−1) 539.1.

Preparation 81

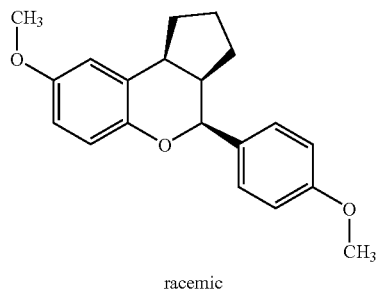

racemic

Preparation 82

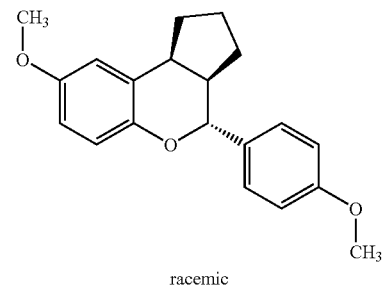

racemic

Place a solution of Preparation 78 (0.33 g, 1.07 mmol) and 5% palladium on carbon (33 mg) in methanol (50 mL) under 60 psi hydrogen at ambient temperature on a parr shaker and shake overnight. Flush the mixture with nitrogen, filter through celite, and concentrate in vacuo. Flash chromatograph the resulting oil with 60% dichloromethane/hexane to yield Preparation 81 (90 mg, 27%) and Preparation 82 (50 mg, 15%) as light pink solids. Preparation 81—$^1$H NMR (CDCl$_3$): 7.35 (d, J=8.6, 2H), 6.90 (d, J=8.6, 2H), 6.81 (d, J=8.8, 1H), 6.68–6.63 (m, 2H), 5.04 (d, J=2.5, 1H), 3.79 (s, 3H), 3.75 (s, 3H), 3.47–3.43 (m, 1H), 2.58–2.52 (m, 1H), 2.17–2.08 (m, 1H), 1.83–1.76 (m, 1H), 1.69–1.58 (m, 1H), 1.52–1.35 (m, 3H). MS calcd. 310.2; MS (M+1) 311.2.

Preparation 82—$^1$H NMR (CDCl$_3$): 7.31 (d, J=8.6, 2H), 6.90 (d, J=8.7, 2H), 6.82 (d, J=8.8, 1H), 6.74 (d, J=2.9, 1H), 6.67 (dd, J=2.9, 8.8, 1H), 4.24 (d, J=10.8, 1H), 3.80 (s, 3H), 3.75 (s, 3H), 3.12–3.06 (m, 1H), 2.58–2.50 (m, 1H), 2.37–2.28 (m, 1H), 1.78–1.70 (m, 2H), 1.63–1.55 (m, 2H), 1.34–1.23 (m, 1H). MS calcd. 310.2; MS (M+1) 311.2.

EXAMPLE 17

Preparation of (+)-2-(4-hydroxyphenyl)-cyclopentyl [c]3,4-dihydro-2H-1-benzopyran

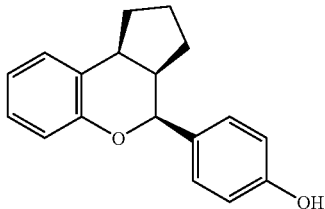

racemic

EXAMPLE 18

Preparation of (+)-2-(4-hydroxyphenyl)-cyclopentyl [c]3,4-dihydro-2H-1-benzopyran

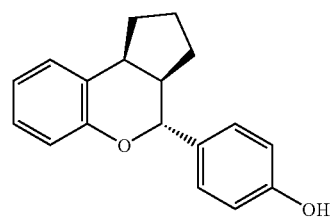

racemic

Stir a solution of Preparation 79 (0.40 g, 1.01 mmol) and tetrabutylammonium fluoride (1.0 M in THF, 1.1 mL, 1.10 mmol) in THF (5 mL) at ambient temperature for 30 minutes, then add 1 N HCl (5 mL) and stir 5 minutes. Add ethyl acetate, wash with concentrated bicarbonate and brine, dry the organic layer over sodium sulfate, and concentrate in vacuo. Redissolve the crude material in methanol (10 mL) and add ammonia (2.0 M in methanol, 0.26 mL, 0.52 mmol). Add 5% palladium on carbon (30 mg), place a hydrogen balloon on the reaction, and stir at ambient temperature overnight. Filter the reaction through celite, concentrate in vacuo, and flash chromatograph with 2% diethyl ether/dichloromethane to yield Examples 17 and 18 as light pink foams.

Example 17—$^1$H NMR (d$_6$-DMSO): 9.41 (s, 1H), 7.24 (d, J=8.6, 2H), 7.10 (d, J=7.5, 1H), 7.02–6.99 (m, 1H), 6.87–6.80 (m, 2H), 6.73 (d, J=8.6, 2H), 5.02 (s, 1H), 3.42–3.38 (m, 1H), 2.55 (m, 1H), 2.11–2.01 (m, 1H), 1.79–1.71 (m, 1H), 1.58–1.49 (m, 1H), 1.42–1.25 (m, 3H). MS calcd. 266.2; MS (M−1) 265.2.

Example 18—$^1$H NMR (d$_6$-DMSO): 9.42 (s, 1H), 7.22 (d, J=7.0, 3H), 7.04 (t, J=7.4, 7.9, 1H), 6.86 (t, J=7.4, 7.4, 1H), 6.76–6.73 (m, 3H), 4.25 (d, J=11.00, 1H), 3.05–2.98 (m, 1H), 2.48–2.41 9M, 1H), 2.35–2.22 (m, 1H), 1.68–1.22 (m, 2H), 1.56–1.48 (m, 1H), 1.21–1.13 (m, 1H). MS calcd. 266.2; MS (M−1) 265.2.

EXAMPLE 19

Preparation of ($^+$)-2-(4-hydroxyphenyl)-6-hydroxy-7-methyl-cyclopentyl[c]3,4-dihydro-2H-1-benzopyran

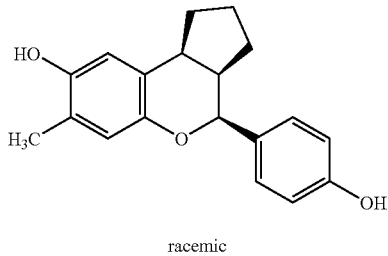

racemic

EXAMPLE 20

Preparation of ($^+$)-2-(4-hydroxyphenyl)-6-hydroxy-7-methyl-cyclopentyl[c]3,4-dihydro-2H-1-benzopyran

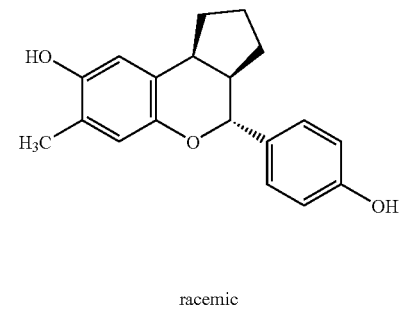

racemic

Stir a solution of Preparation 80 (0.42 g, 0.78 mmol) and tetrabutylammonium fluoride (1.0 M in THF, 1.6 mL, 1.63 mmol) in THF (20 mL) at ambient temperature for 30 minutes, then add 1 N HCl (7 mL) and stir 5 minutes. Add ethyl acetate, wash with concentrated bicarbonate and brine, dry the organic layer over sodium sulfate, and concentrate in vacuo. Flash chromatograph the crude product with 60% ethyl acetate/hexane. Redissolve the resulting material in methanol (10 mL), add 5% palladium on carbon (60 mg), place a hydrogen balloon on the reaction, and stir at ambient temperature overnight. Filter the reaction through celite, concentrate in vacuo, and flash chromatograph with 3% methanol/dichloromethane to yield Examples 19 and 20 as light pink solids.

Example 19—$^1$H NMR (MeOD): 7.24 (d, J=9.0, 2H), 6.77 (d, J=9.3, 2H), 6.56 (s, 1H), 6.54 (s, 1H), 4.92 (d, J=1.6, 1H), 3.39–3.31 (m, 1H), 2.58–2.49 (m, 1H), 2.15–2.03 (m, 4H), 1.79–1.71 (m, 1H), 1.63–1152 (m, 1H), 1.49–1.28 (m, 3H). MS calcd. 296.1; MS (M−1) 295.1.

Example 20—$^1$H NMR (MeOD): 7.22 (d, J=8.6, 2H), 6.78 (d, J=8.7, 2H), 6.59 (s, 1H), 6.52 (s, 1H), 4.17, (10.9, 1H), 3.01–2.92 (m, 1H), 2.56–1.45 (m, 1H), 2.31–2.22 (m, 1H), 2.10 (s, 3H), 1.78–1.62 (m, 2H), 1.59–1.50 (m, 2H), 1.33–1.25 (m, 1H). MS calcd. 296.1; MS (M−1) 295.1.

Preparation 83

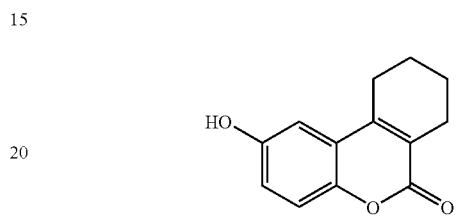

Cool a solution of hydroquinone (6.0 g, 54.49 mmol) in 80% sulfuric acid (20 mL) to 0° C. and add ethyl 2-oxo-cyclohexane carboxylate (19.48 g, 114.43 mmol). Stir at ambient temperature for 24 hours. Pour into ice water and collect precipitate by vacuum filtration. Wash the collected solid with ample H$_2$O. Dissolve solid with 4% methanol/chloroform and chromatograph on flash column (silica gel; 2–5% MeOH gradient in CH$_2$Cl$_2$), to yield the Preparation 83 (3.40 g, 29%) as an off-white amorphous solid. $^1$H NMR (d$_6$-DMSO): 9.59 (s, 1H), 7.13 (app d, J=9.7, 1H), 6.89–6.92 (m, 2H), 2.62–2.65 (m, 2H), 2.33–2.36 (m, 2H), 1.64–1.74 (m, 4H); MS (IS) m/e 217 (M+1).

Preparation 84

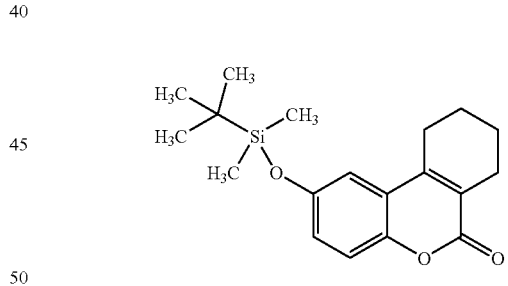

Stir a solution of Preparation 83 (2.82 g, 13.06 mmol), t-butyldimethylsilyl chloride (2.95 g, 19.58 mmol), imidazole (1.78 g, 26.11 mmol) and 4-(dimethylamino)pyridine (0.32 g, 2.61 mmol) in anhydrous DMF (75 mL) for 18 hours at ambient temperature. Add saturated aqueous sodium bicarbonate and extract with ethyl acetate. Wash the combined extracts with saturated aqueous sodium bicarbonate, water and brine, dry (sodium sulfate) and evaporate to provide a light yellow solid. Purify the resulting solid by flash chromatography (silica gel; 10–20 diethyl ether gradient in hexanes) to yield Preparation 84 (3.80 g, 88%) as a white solid. $^1$H NMR (CDCl$_3$): 7.35 (d, J=2.93 Hz, 1H), 7.06 (d, J=8.80 Hz, 1H), 6.90 (dd, J=9.29, 2.94 Hz, 1H), 2.44 (t, J=6.36 Hz, 2H), 2.36 (t, J=6.36 Hz, 2H), 1.62–1.66 (m, 2H), 1.52–1.57 (m, 2H), 0.78 (s, 9H), 0.00 (s, 6H); MS (IS) m/e 331 (M+1).

Preparation 85

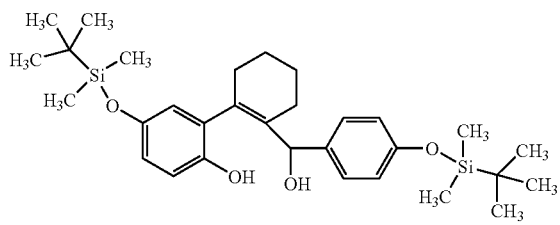

Cool a solution of Preparation 84 (1.00 g, 3.03 mmol) in anhydrous tetrahydrofuran (35 mL) to −78° C. and add a 1.0 molar solution of diisobutylaluminum hydride in toluene (3.48 mL, 3.48 mmol) dropwise, so temperature does not rise above 65° C. Stir the reaction at −78° C. for 3.5 hours. Quench the reaction with saturated aqueous ammonium chloride and saturated aqueous potassium sodium tartrate, then warm the resulting mixture to ambient temperature. Extract the resulting aqueous mixture with ethyl acetate. Wash the combined extracts with saturated aqueous potassium sodium tartrate and brine, then dry (sodium sulfate) and concentrate in vacuo. Dissolve the resulting white crystalline solid in anhydrous THF (30 ml). Add it dropwise over 30 minutes to a −78° C. stirring solution of Preparation 75 (8.91 mmol) in anhydrous THF (18 mL). Stir the reaction at −78° C. for 1.5 hours. Add water (50 mL) and saturated aqueous sodium bicarbonate (50 mL), then warm to ambient temperature, and stir 30 minutes. Extract the resulting aqueous mixture with diethyl ether then ethyl acetate. Wash the combined organics with saturated aqueous potassium sodium tartrate, water and brine, then dry (sodium sulfate) and concentrate in vacuo. Purify the resulting material on a flash column (silica gel; 25–60% ethyl acetate gradient in hexanes) to yield Preparation 85 (1.10 g, 67%) as an off-white foam solid. MS (IS) m/e 539 (M−1);

Preparation 86

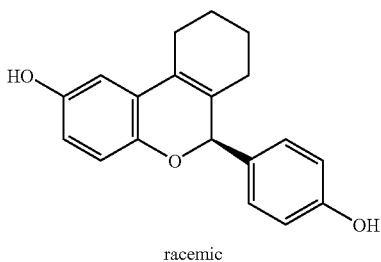

racemic

Stir a solution of Preparation 85 (0.89 g, 1.65 mmol) and tetrabutylammonium fluoride (1.0 M in THF, 3.46 mL, 3.46 mmol) in THF (25 mL) at ambient temperature for 10 minutes, then add TFA (0.65 mL, 8.2 mmol) and stir for 4 hours. Pour reaction mixture over cold saturated aqueous sodium bicarbonate. Extract the resulting aqueous mixture into ethyl acetate. Wash the combined extracts with brine, dry (sodium sulfate) and concentrate in vacuo. Flash chromatograph the crude product (silica gel; 25–50% ethyl acetate gradient in hexanes) to provide the product Preparation 86, 410 mg (85%). MS (IS) m/e 295 (M+1);

EXAMPLE 21

Preparation of (+)-2-(4-hydroxyphenyl)-6-hydroxy-cyclohexyl[c]-3,4-dihydro-2H-1-benzopyran

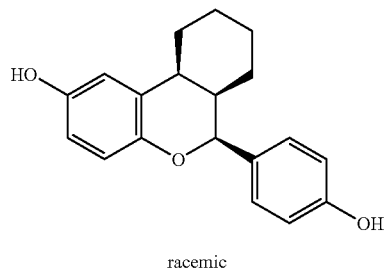

racemic

Dissolve Preparation 86 (380 mg, 1.30 mmol) in methanol (17 mL), add a 2.0 M solution of ammonia in methanol (0.323 mL, 0.65 mmol) and 5% palladium on carbon (225 mg). Place a hydrogen balloon on the reaction, and stir at ambient temperature overnight. Filter the reaction through celite, concentrate in vacuo, and flash chromatograph the resulting material (silica gel; 25–45% ethyl acetate gradient in hexanes) to yield Example 21 as a light pink solid foam, 190 mg (50%). Example 21—$^1$H NMR (DMSO-$d_6$): 9.30 (s, 1H), 8.77 (s, 1H), 7.16 (d, J=8.60 Hz, 2H), 6.73 (d, J=8.60, 2H), 6.67 (app d, J=2.35 Hz, 1H), 6.63 (d, J=8.60 Hz, 1H), 6.49 (app dd, J=9.00, 2.74 Hz, 1H), 4.99 (s, 1H), 3.29–3.34 (m, 1H), 2.24–2.28 (m, 1H), 1.89–1.94 (m, 1H), 1.59–1.65 (m, 1H), 1.47–1.56 (m, 1H), 1.33–1.39 (m, 1H), 0.90–1.12 (m, 4H). MS (IS) m/e 295 (M−1).

EXAMPLE 22

Preparation of (+)-2-(4-methoxyphenyl)-6-methoxy-cyclopentyl[c]3,4-dihydro-2H-1-benzopyran

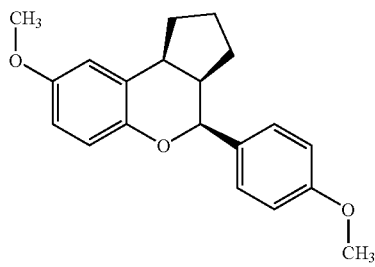

racemic

See preparation 81.

EXAMPLE 23

Preparation of (+)-2-(4-methoxyphenyl)-6-methoxy-cyclopentyl[c]3,4-dihydro-2H-1-benzopyran

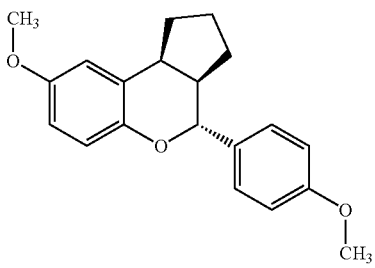

racemic

See preparation 82.

Preparation 87

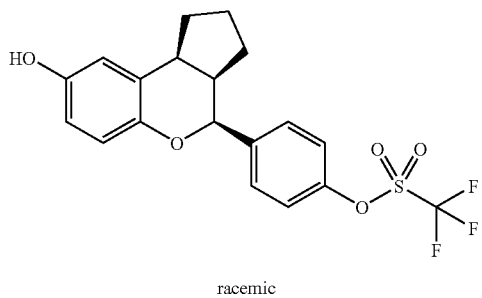

racemic

Preparation 88

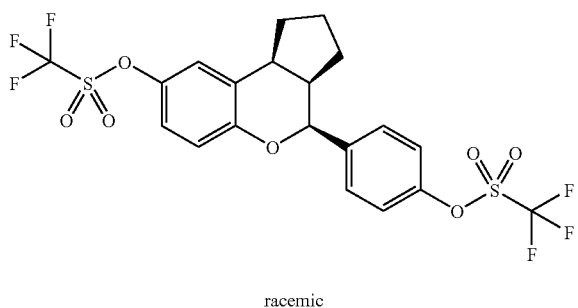

racemic

Stir a solution of Example 1 (0.100 g, 0.354 mmol) and cesium carbonate (0.287 g, 0.88 mmol) in DMF (5 mL) for 5 minutes. Add N-phenyltriflamide (0.136 g, 0.38 mmol) in one portion, and allow the solution to stir for 16 hours. Add saturated aqueous sodium bicarbonate and extract with ethyl acetate. Wash the combined extracts with saturated aqueous sodium bicarbonate, water (2×) and brine, dry (sodium sulfate) and evaporate to provide a yellow solid. Purify the resulting solid by flash chromatography (silica gel; 0-10-25 ethyl acetate gradient in hexanes) to separately yield Preparation 88 (0.038 g, 20%) followed by Preparation 87 (0.052 g, 36%) as white solids. $^1$H NMR of Preparation 88 (CDCl$_3$): 7.54 (d, J=8.4 Hz, 2H), 7.32 (d, J=8.4 Hz, 2H), 7.11 (d, J=2.8 Hz, 1H), 7.02 (dd, J=2.8, 9.0 Hz, 1H), 6.96 (d, J=9.0 Hz, 1H), 5.22 (d, J=2.0 Hz, 1H), 3.57 (dt, J=2.8, 7.8 Hz, 1H), 2.65 (m, 1H), 2.22 (m, 1H), 1.82 (m, 1H), 1.55 (m, 3H), 1.38 (m, 1H). $^1$H NMR of Preparation 87 (CDCl$_3$): 7.54 (d, J=8.0 Hz, 2H), 7.29 (d, J=8.0 Hz, 2H), 6.79 (d, J=8.8 Hz, 1H), 6.67 (d, J=2.8 Hz, 1H), 6.61 (dd, J=2.8, 8.0 Hz, 1H), 5.12 (d, J=2.0 Hz, 1H), 4.55 (br s, 1 h), 3.49 (dt, J=2.8, 7.8 Hz, 1H), 2.62 (dq, J=2.4, 8.4 Hz, 1H), 2.16 (m, 1H), 1.80 (m, 1H), 1.53 (m, 3H), 1.31 (m 1H).

EXAMPLE 24

Preparation of (+)-2-(4-aminocarbonylphenyl)-6-aminocarbonyl-cyclopentyl[c]3,4-dihydro-2H-1-benzopyran

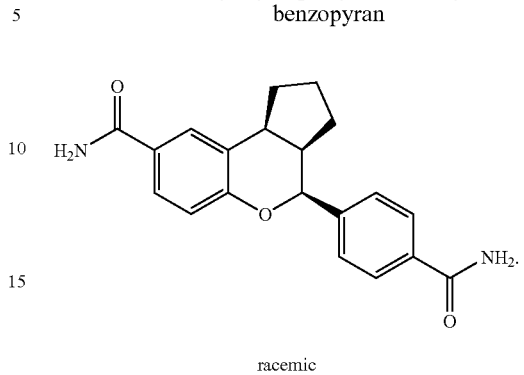

racemic

Stir a solution of Preparation 88 (0.038 g, 0.07 mmol) and palladium(II) bis(triphenylphosphine)-dichloride (0.003 g, 0.0035 mmol) in DMSO (1 mL) and hexamethyldisilylazane (0.25 mL). Add an atmospheric blanket of carbon monoxide and heat the reaction to 80 C for 16 hours. Allow the reaction to cool to room temperature. Add saturated aqueous sodium bicarbonate and extract with ethyl acetate. Wash the combined extracts with saturated aqueous sodium bicarbonate, water (2×) and brine, dry (sodium sulfate) and evaporate to provide a yellow solid. Purify the resulting solid by flash chromatography (silica gel; 0-50-80 ethyl acetate gradient in hexanes) to afford Example 24 (0.011 g, 47%) as a white solid. $^1$H NMR of Example 24 (CDCl$_3$): 7.85 (d, J=8.4 Hz, 2H), 7.54 (d, J=8.4 Hz, 2H), 7.10 (d, J=2.8 Hz, 1H), 7.03 (dd, J=2.8, 8.0 Hz, 1H), 6.97 (d, J=8.0 Hz, 1H), 6.10 (br s, 2H), 5.80 (br s, 2H), 5.24 (d, J=1.6 Hz, 1H), 3.57 (br t, J=7.8 Hz, 1H), 2.68 (m, 1H), 2.21 (m, 1H), 1.80 (m, 1H), 1.53 (m, 3H), 1.34 (m, 1H).

EXAMPLE 25

Preparation of (+)-2-(4-aminocarbonylphenyl)-6-hydroxy-cyclopentyl[c]3,4-dihydro-2H-1-benzopyran

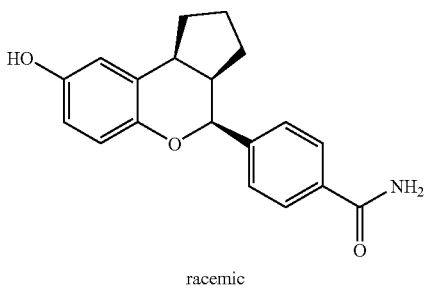

racemic

Stir a solution of Preparation 87 (0.052 g, 0.126 mmol) and palladium(II) bis(triphenylphosphine)-dichloride (0.005 g, 0.006 mmol) in DMSO (1 mL) and hexamethyldisilylazane (0.25 mL). Add an atmospheric blanket of carbon monoxide and heat the reaction to 80 C for 16 hours. Allow the reaction to cool to room temperature. Add saturated aqueous sodium bicarbonate and extract with ethyl acetate. Wash the combined extracts with saturated aqueous sodium bicarbonate, water (2×) and brine, dry (sodium sulfate) and evaporate to provide a yellow solid. Purify the resulting solid by flash chromatography (silica gel; 0-50-80 ethyl acetate gradient in hexanes) to afford Example 25 (0.022 g, 47%) as a white solid. $^1$H NMR of Example 25 (CDCl$_3$): 7.83 (d, J=8.2 Hz, 2H), 7.54 (d, J=8.2 Hz, 2H), 6.79 (d, J=8.4 Hz, 1H), 6.66 (d, J=2.8 Hz, 1H), 6.60 (dd, J=2.8, 8.4 Hz, 1H), 5.9–6.2 (br d, 2H), 5.16 (d, J=2.0H, 1H), 3.49 (dt, J=2.0, 7.8 Hz, 1H), 2.62 (dq, J=2.0, 8.0 Hz, 1H), 2.15 (m, 1H), 1.81 (m, 1H), 1.42–1.65 (m, 3H), 1.29 (m, 1H).

Preparation 89

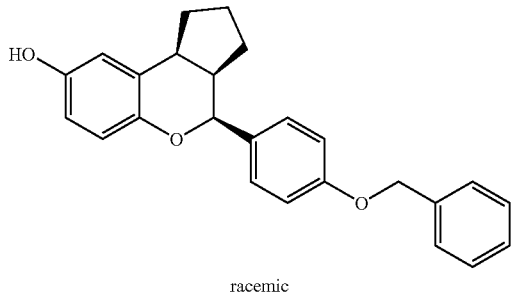

racemic

Stir a solution of Example 1 (0.100 g, 0.354 mmol) and cesium carbonate (0.287 g, 0.88 mmol) in DMF (4 mL) for 5 minutes. Add benzyl chloride (0.045 mL, 0.39 mmol) and allow the solution to stir for 4 hours. Add saturated aqueous sodium bicarbonate and extract with ethyl acetate. Wash the combined extracts with saturated aqueous sodium bicarbonate, water (2×) and brine, dry (sodium sulfate) and evaporate to provide a yellow solid. Purify the resulting solid by flash chromatography (silica gel; 0-15-30 ethyl acetate gradient in hexanes) to afford an inseparable 2:1 mixture of two intermediate monobenzyl ethers (0.062 g, 47%). $^1$H NMR of the major benzyl ether Preparation 89 (CD$_3$OD): 7.46 (m, 2H), 7.38 (d, J=8.0 Hz, 2H), 7.28–7.41 (m, 3H), 7.01 (d, J=8.0 Hz, 2H), 6.72 (d, J=8.8 Hz, 1H), 6.64 (d, J=2.8 Hz, 1H), 6.56 (dd, J=2.8, 8.8 Hz, 1H), 5.11 (s, 2H), 5.02 (d, J=2.2 Hz, 1H), 3.47 (t, J=8.4 Hz, 1H), 2.63 (m, 1H), 2.16 (m, 1H), 1.81 (m, 1H), 1.62 (m, 1H), 1.51 (m, 2H), 1.37 (m, 1H).

EXAMPLE 26

Preparation of (+)-2-(4-hydroxyphenyl)-6-aminocarbonyl-cyclopentyl[c]3,4-dihydro-2H-1-benzopyran

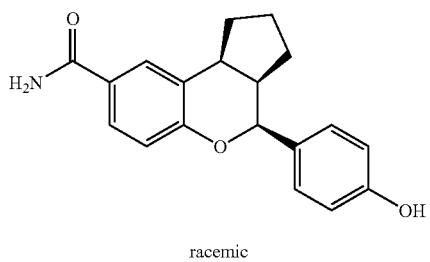

racemic

Stir a solution of the intermediate benzyl ethers from Preparation 89 (0.062 g, 0.166 mmol) and cesium carbonate (0.108 g, 0.33 mmol) in DMF (4 mL) for 5 minutes. Add N-phenyl triflamide (0.089 g, 0.249 mmol) and allow the solution to stir for 4 hours. Add saturated aqueous sodium bicarbonate and extract with ethyl acetate. Wash the combined extracts with saturated aqueous sodium bicarbonate, water (2×) and brine, dry (sodium sulfate) and evaporate to provide a yellow solid. Purification of the resulting solid by flash chromatography (silica gel; 0-10-20 ethyl acetate gradient in hexanes) yields an inseparable 2:1 mixture of two intermediate triflates (0.070 g, 84%). Stir a solution of the resulting triflamides and palladium(II) bis(triphenylphosphine)-dichloride (0.003 g, 0.0035 mmol) in DMF (0.42 mL) and hexamethyldisilylazane (0.12 mL). Add an atmospheric blanket of carbon monoxide and heat the reaction to 80 C for 16 hours. Allow the reaction to cool to room temperature. Add saturated aqueous sodium bicarbonate and extract with ethyl acetate. Wash the combined extracts with saturated aqueous sodium bicarbonate, water (2×) and brine, dry (sodium sulfate) and evaporate to provide a yellow solid. Purify the resulting solid by flash chromatography (silica gel; 0-50-80 ethyl acetate gradient in hexanes) to afford an inseparable 2:1 mixture of carboxamides (0.021 g, 37%) as a white solid. Stir a solution of carboxamides (0.021 g, 0.051 mmol) and 10% Pd on carbon (0.005 g) in THF (4 mL) and MeOH (10 mL) under H2 (40 psi) for 4 hours. Purge with N2, then filter to afford a mixture of the desired Example 26 and Example 25, which are separated by HPLC.

EXAMPLE 27

Preparation of (+)-2-(4-methoxyphenyl)-6-hydroxy-cyclopentyl[c]3,4-dihydro-2H-1-benzopyran

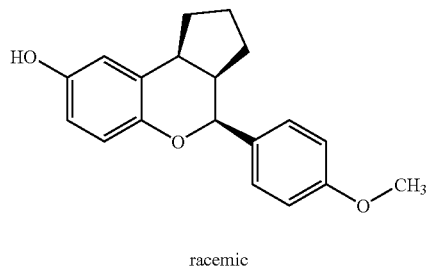

racemic

Stir a solution of Example 1 (0.060 g, 0.21 mmol) and diisopropylethylamine (0.044 mL, 0.25 mmol) in MeOH (0.1 mL) and acetonitrile (1 mL) for 5 minutes. Add a solution of trimethylsilyl diazomethane (0.105 mL, 2.0 M in hexanes, 0.21 mmol), and allow the reaction to stir for 16 hours. Concentrate the mixture to provide a light yellow solid. Purify the resulting solid by flash chromatography (silica gel; 0-10-20 ethyl acetate gradient in hexanes) to yield Example 22 (0.009 g, 14%), Example 27, (0.021 g, 33%) as a white solid, Example 7 (0.008 g, 9%), and recovered starting material (0.018 g, 30%). $^1$H NMR of Example 27 (CDCl$_3$): 7.38 (d, J=8.2 Hz, 2H), 6.92 (d, J=8.2 Hz, 2H), 6.79 (d, J=8.4 Hz, 1H), 6.66 (d, J=3.2 Hz, 1H), 6.59 (dd, J=3.2, 8.4 Hz, 1H), 5.06 (d, J=1.8 Hz, 1H), 3.83 (s, 3H), 3.46 (dt, J=2.4, 8.0 Hz, 1H), 2.58 (m, 1H), 2.13 (m, 1H), 1.81 (m, 1H), 1.36–1.70 (m, 4H). MS calcd 296.2; MS (M−1) 295.1.

Preparation 90

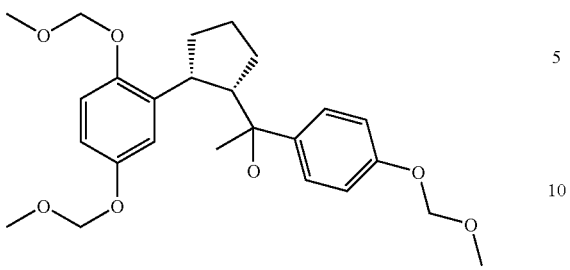

Cool a mixture of Preparation 55 (150 mg, 0.35 mmol) and THF (4 mL) to 0° C. Add methyl lithium (1.6 M in Et$_2$O, 0.31 mL) drop wise. Stir the reaction for 30 minutes and quench with saturated NH$_4$Cl. Extract with EtOAc (2×), dry (Na$_2$SO$_4$), filter and concentrate in vacuo. Product of Preparation 90 is pure and is taken to the next step without further purification. HRMS calcd. 469.2202; found (electrospray, M+Na) 469.2205.

EXAMPLE 28

Preparation of (+)-2-methyl-2-(4-hydroxyphenyl)-6-hydroxy-cyclopentyl[c]3,4-dihydro-2H-1-benzopyran

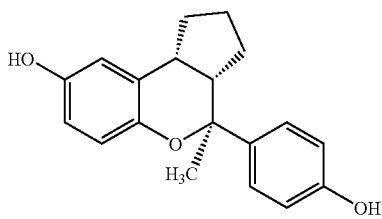

To a solution of Preparation 90 (60 mg, 0.13 mmol) in anhydrous methanol (6 mL) add p-toluenesulfonic acid (25 mg, 0.13 mmol) and heat the resulting solution to 50° C. for 18 hours under nitrogen. Cool the reaction to ambient temperature, concentrate in vacuo and purify by flash chromatography (10 g SiO$_2$, 40 mL/min, 20–50% EtOAc/Hex for 25 minutes) to afford Example 28 (30 mg, 0.1 mmol, 70%) as a yellow solid. HRMS calcd. 296.1412; found (EI+) 296.1436.

Preparation 91

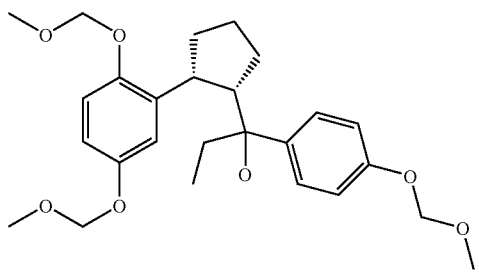

Cool a mixture of Preparation 55 (115 mg, 0.27 mmol) and THF (4 mL) to 0° C. Add EtMgCl (2.0 M in THF, 0.27 mL) drop wise. Stir the reaction for 30 minutes and quench with saturated NH$_4$Cl. Extract with EtOAc (2×), dry (Na$_2$SO$_4$), filter and concentrate in vacuo. Purify by flash chromatography (10 g SiO$_2$, 40 mL/min, 0–30% EtOAc/Hex for 25 min and 30% EtOAc for 7 minutes) to yield Preparation 91 (95 mg, 77%) as a pale yellow oil. HRMS calcd. 483.2359; found (electrospray, M+Na) 483.2325.

EXAMPLE 29

Preparation of (+)-2-ethyl-2-(4-hydroxyphenyl)-6-hydroxy-cyclopentyl[c]3,4-dihydro-2H-1-benzopyran

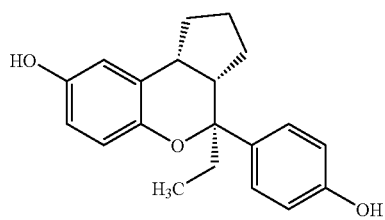

To a solution of Preparation 91 (70 mg, 0.15 mmol) in anhydrous methanol (6 mL) add p-toluenesulfonic acid (29 mg, 0.15 mmol) and heat the resulting solution to 50° C. for 18 hours under nitrogen. Cool the reaction to ambient temperature, concentrate in vacuo and purify by flash chromatography (10 g SiO$_2$, 40 mL/min, 10–40% EtOAc/Hex for 25 minutes) to afford Example 29 (40 mg, 0.13 mmol, 87%) as a pink solid. HRMS calcd. 310.1569; found (EI+) 310.1578.

Preparation 92

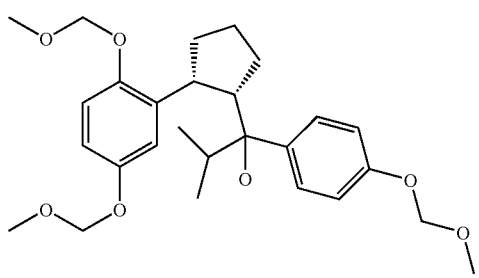

Cool a mixture of Preparation 55 (115 mg, 0.27 mmol) and THF (4 mL) to 0° C. Add i-PrMgCl (2.0 M in THF, 0.27 mL) drop wise. Warm the reaction to room temperature and stir over night. Quench with saturated NH$_4$Cl, extract with EtOAc (2×), dry (Na$_2$SO$_4$), filter and concentrate in vacuo. Purify by flash chromatography (10 g SiO$_2$, 40 mL/min, 0–30% EtOAc/Hex for 25 min and 30% EtOAc for 7 minutes) to afford Preparation 92 (70 mg, 55%) as a pale yellow oil. HRMS calcd. 497.2515; found (electrospray, M+Na) 497.2500.

EXAMPLE 30

Preparation of (+)-2-(1-methylethyl)-2-(4-hydroxyphenyl)-6-hydroxy-cyclopentyl[c]3,4-dihydro-2H-1-benzopyran

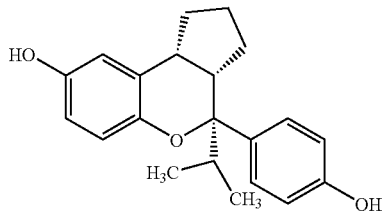

To a solution of Preparation 92 (60 mg, 0.13 mmol) in anhydrous methanol (6 mL) add p-toluenesulfonic acid (25 mg, 0.13 mmol) and heat the resulting solution to 50° C. for 18 hours under nitrogen. Cool the reaction to ambient temperature, concentrate in vacuo and purify by flash chromatography (10 g SiO$_2$, 40 mL/min, 10–40% EtOAc/Hex for 25 minutes) to afford Example 30 (32 mg, 0.1 mmol, 78%) as a pink solid. MS calcd. 323.16; found (electrospray, M−1) 323.1.

Test Procedures

ER Binding Assay

The competition ER binding assay was run in a buffer containing 50 mM N-[2-hydroxyethyl]piperazine-N'-[2-ethanesulfonic acid (Hepes) pH 7.5, 1.5 mM EDTA, 150 mM NaCl, 10% glycerol, 1 mg/mL ovalbumin, 5 mM DTT, 0.025 µCi per well of $^3$H-Estradiol (NEN #NET517 at 118 Ci/mmol, 1 mCi/mL), and 10 ng/well ERAlpha or ERbeta Receptor (Pan Vera). Competing compounds were added at 10 different concentrations. Non-specific binding was determined in the presence of 1 µM of E2 (17-β Estradiol, Sigma, St. Louis, Mo.). The binding reaction (140 µL) was incubated for 4 hours at room temperature, then 70 µL of cold dextran coated charcoal (DCC) buffer was added to each reaction (DCC buffer was prepared by adding 0.75 g of charcoal [Sigma] and 0.25 g of dextran [Pharmacia] per 50 mL of assay buffer). The incubation plates were mixed for 8 minutes on an orbital shaker at 4° C. and then centrifuged at 3,000 rpm for 10 minutes at 4° C. An aliquot of 120 µl of the mix was transferred to another 96-well, white flat bottom plate (Costar) and 175 µl of Wallac Optiphase Hisafe 3 scintillation fluid was added to each well. The plates were sealed and then shaken vigorously on an orbital shaker. After an incubation of 2.5 hrs, the radioactivity was counted in a Wallac Microbeta counter. The IC$_{50}$ and percent inhibition at 10 µM were calculated. The K$_d$ for $^3$H-Estradiol was determined by saturation binding to ERα and ERβ receptors. The IC$_{50}$ values for compounds were converted to K$_i$ values using the Cheng-Prusoff equation and the K$_d$ values were determined by saturation binding assay. Compounds of Examples 1–30 are active in the assay as described. The compounds of Table 1 bind to the ER beta receptor with a K$_i$ of less than 100 nM. Preferred compounds bind to the ER beta receptor with a K$_i$ of less than 20 nM. More preferred compounds bind to the ER beta receptor with a K$_i$ of less than 1 nM. Compounds that are selective for binding to the ER beta receptor compared to the ER alpha receptor bind to the ER beta receptor with a lower K$_i$ compared to the K$_i$ for the ER alpha receptor. Preferred selective ER beta compounds bind to ER beta receptor with a K$_i$(ER alpha)/K$_i$(ER beta) ratio of greater than 4 as shown in Table 1.

Ratio of K$_j$ (nM) ER alpha/K$_i$ (nM) ER beta

| Example | K$_i$ (nM) ER alpha/ K$_i$ (nM) ER beta |
|---|---|
| 1 | 8.0 |
| 2 | 1.4 |
| 3 | 1.2 |
| 4 | 4.7 |
| 5 | 0.5 |
| 6 | 2.3 |
| 7 | 5.1 |
| 8 | 5.3 |
| 9 | 13 |
| 10 | 2.5 |
| 11 | 1.6 |
| 12 | 2.3 |
| 13 | 4.4 |
| 14 | 2.6 |
| 15 | 11 |
| 16 | 1.4 |
| 17 | 1.9 |
| 18 | 3.8 |
| 19 | 2.0 |
| 20 | 0.6 |
| 21 | 4.6 |
| 28 | 4.6 |
| 29 | 1.3 |
| 30 | 1.4 |

LNCaP Human PCa Xenograft Assay

ERbeta agonists are evaluated for their effects on the growth of androgen-sensitive LNCaP human prostatic cancer (PCa) xenografts grown in intact sexually mature (5–6 weeks old) Hsd: Athymic Nude-nu (Athymic Nude) male mice. 2.0×10$^6$ LNCaP tumor cells are injected bilaterally by the subcutaneous route into the pre-tracheal region of testicular intact male mice. Mice are castrated via the scrotal route to serve as the positive control group. Test compounds are administered once per day by subcutaneous or gavage administration at multiple dose levels in a volume of 0.2 ml to xenograft-bearing mice starting on the day following tumor injection. Test compounds are reformulated weekly based on average group mean body weights. The vehicle for these studies is 1% carboxymethyl cellulose (CMC) with 0.25% Tween 80. Body weights and tumor measurements are recorded on a weekly basis and entered directly into a JMP™ (SAS; Cary, N.C.) spreadsheet from electronic caliper measurement. Tumor volumes in mm$^3$ are calculated in JMP using the following formula: L X W X H X 0.5236. Tumor and body weight responses for individual mice are recorded on a weekly basis. When LNCaP tumor volumes enter log-phase expansion, lesions are measured every 3–4 days. Growth rates are determined using linear modeling of the log tumor values and time to treatment failure (tumor vol=1300–1500 mm$^3$) are determined using a linear extrapolation model (SAS; Cary, N.C.). Because of humane animal use considerations, animals are sacrificed when their tumor volumes approach 1200–1400 mm$^3$. At necropsy, final tumor measurement and body weights are recorded and whole blood is obtained via cardiac puncture and allowed to clot on ice. Serum is transferred to appropriately labeled 0.5 ml Eppendorf micro tubes, and samples are stored at −80° C. for biomarker analysis.

General Rat Preparation Procedure

Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily dosing with a compound of formula (I) ("F-I") is initiated. 17α-ethynyl estradiol or F-I is given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine:Xylazine (2:1, v:v) mixture and a blood sample is collected by cardiac puncture. The animals are then sacrificed by asphyxiation with $CO_2$, the uterus is removed through a midline incision, and a wet uterine weight is determined. 17α-ethynyl estradiol is obtained from Sigma Chemical Co., St. Louis, Mo.

Cardiovascular Disease/Hyperlipidemia

The blood samples from above are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

The uteri from above are kept at 4° C. until time of enzymatic analysis. The uteri are then homogenized in 50 volumes of 50 mM Tris buffer (pH 8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosinophils in the uterus is an indication of estrogenic activity of a compound. The maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized X-rays generated and analyzed by an image analysis program (NIH image) at the distal metaphysis. The proximal aspect of the tibiae from these animals are also scanned by quantitative computed tomography. In accordance with the above procedures, F-I or ethynyl estradiol ($EE_2$) in 20% hydroxypropyl β-cyclodextrin are orally administered to test animals.

Therapeutic Methods of Use and Dosages

Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (I).

As used herein, the term "patient" refers to a warm blooded animal such as a mammal that is afflicted with a particular estrogen receptor-beta mediated disease. It is understood that guinea pigs, dogs, cats, rats, mice, horses, cattle, sheep, and humans are examples of animals within the scope of the meaning of the term.

As used herein, the term "therapeutically effective amount" of a compound of formula (I) refers to an amount which is effective in controlling diseases and conditions associated with estrogen receptor-beta mediated diseases such as prostate cancer, benign prostatic hyperplasia, testicular cancer, cardiovascular diseases, neurodegenerative disorders, urinary incontinence, CNS disorders, GI tract disorders, and osteoporosis. The term "controlling" is intended to refer to all processes wherein there may be a slowing, interrupting, arresting, or stopping of the progression of the diseases and conditions described herein, but does not necessarily indicate a total elimination of all disease and condition symptoms, but does include prophylactic treatment of the diseases and conditions associated with estrogen receptor-beta mediated diseases such as prostate cancer, benign prostatic hyperplasia, testicular cancer, cardiovascular diseases, neurodegenerative disorders, urinary incontinence, CNS, GI tract disorders, and osteoporosis.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (I) is expected to vary from about 0.001 milligram per kilogram of body weight per day (mg/kg/day) to about 100 mg/kg/day. Preferred amounts can be determined by one skilled in the art.

In effecting treatment of a patient afflicted with the diseases and conditions described above, a compound of formula (I) can be administered in any form or mode which makes the compound bioavailable in a therapeutically effective amount, including oral, inhalation, and parenteral routes. For example, compounds of formula (I) can be administered orally, by inhalation of an aerosol or dry powder, subcutaneously, intramuscularly, intravenously, transdermally, intranasally, rectally, topically, and the like. Oral or inhalation administration is generally preferred for treatment of respiratory diseases, e.g. asthma. One skilled in the art of preparing formulations can readily select the proper form and mode of administration depending upon the particular characteristics of the compound selected, the disease or condition state to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (I) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system that dispenses the compounds of the present invention or a formulation thereof. Formulations for administration by inhalation of compounds of formula (I) may be delivered in single phase, bi-phasic, or tri-phasic systems. A variety of systems are available for the administration by aerosols of the compounds of formula (I). Dry powder formulations are prepared by either pelletizing or milling the compound of formula (I) to a suitable particle size or by admixing the pelletized or milled compound of formula (I) with a suitable carrier material, such as lactose and the like. Delivery by inhalation includes the necessary container, activators, valves, subcontainers, and the like. Preferred aerosols and dry powder formulations for administration by inhalation are able to be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (I) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

We claim:

1. A compound of the formula I

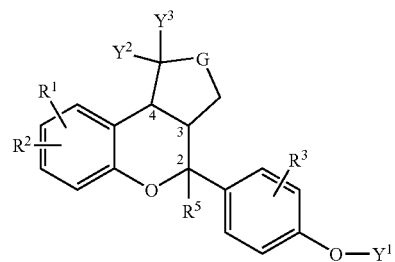

(I)

wherein $R^1$, $R^2$, and $R^3$ are each independently —H, $C_1$–$C_6$ alkyl, —OH, $C_1$–$C_6$ alkoxy, halo, or —$CF_3$;

$R^5$ is hydrogen or $C_1$–$C_6$ alkyl;

$Y^1$, $Y^2$, and $Y^3$ are each independently —H or $C_1$–$C_6$ alkyl; and G is —$CH_2$—, —$CH_2$—$CH_2$—, or —$CH_2$—$CH_2$—$CH_2$—;

or a pharmaceutically acceptable salt thereof.

2. A compound according to claim 1 wherein G is —$CH_2$—.

3. A compound according to claim 1 wherein $Y^2$ and $Y^3$ are both —H.

4. A compound according to claim 1 wherein at least one of $R^1$ and $R^2$ is —OH.

5. A compound according to claim 1 wherein $R^3$ is —H.

6. A compound according to claim 1 wherein $Y^1$ is —H.

7. A compound according to claim 2 wherein one of $R^1$ and $R^2$ is —OH and the other is —H.

8. A compound according to claim 1 of formula III

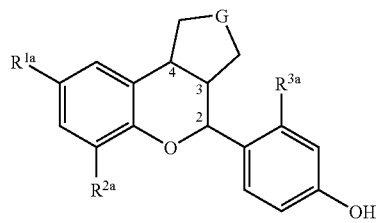

(III)

wherein
$R^{1a}$ is —H, —OH, or —F;
$R^{2a}$ is —H, —CH$_3$, or —OCH$_3$;
$R^{3a}$ is —H or —CH$_3$;
G is —CH$_2$—, —CH$_2$—CH$_2$—, or —CH$_2$—CH$_2$—CH$_2$—;
or a pharmaceutically acceptable salt thereof.

9. A compound according to claim 1 wherein the compound is of the formula IB or IC:

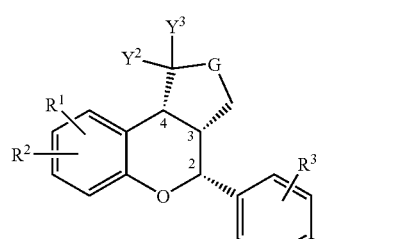

(IB)

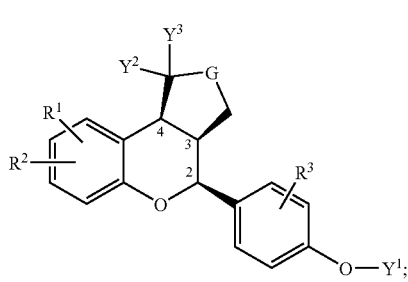

(IC)

or a pharmaceutically acceptable salt thereof.

10. A compound according to claim 1 wherein the compound is of the formula ID or IE:

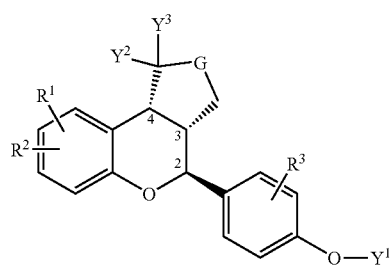

(ID)

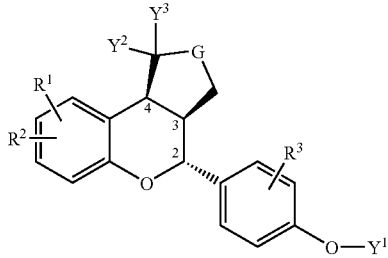

(IE)

or a pharmaceutically acceptable salt thereof.

11. A compound according to claim 1 wherein the compound is an (2S, 3R, 4S) enantiomer of the formula

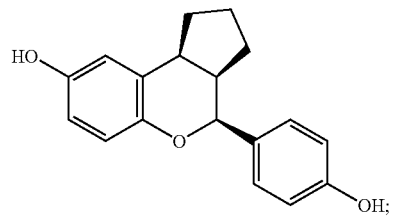

or a pharmaceutically acceptable salt thereof.

12. A compound according to claim 1 wherein the compound is an (2R, 3S, 4R) enantiomer of the formula

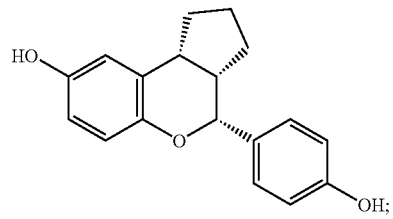

or a pharmaceutically acceptable salt thereof.

13. A compound according to claim 1 wherein the compound is of the formula:

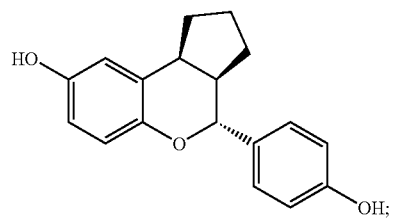

or a pharmaceutically acceptable salt thereof.

14. A compound according to claim 1 wherein the compound is of the formula:

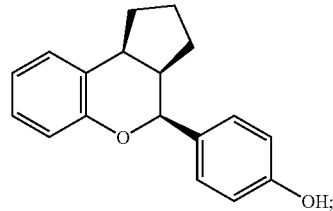

or a pharmaceutically acceptable salt thereof.

15. A compound according to claim 1 wherein the compound is of the formula:

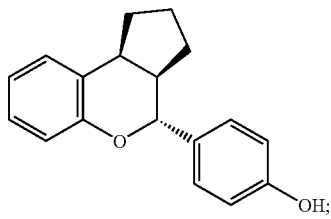

or a pharmaceutically acceptable salt thereof.

16. A compound according to claim 1 wherein the compound is of the formula:

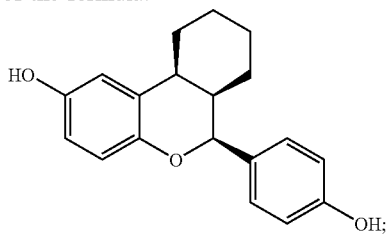

or a pharmaceutically acceptable salt thereof.

17. A compound according to claim 1 wherein the compound is of the formula:

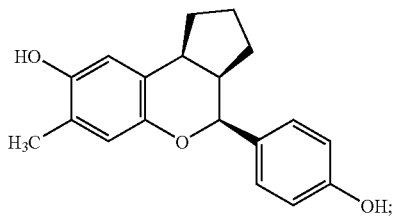

or a pharmaceutically acceptable salt thereof.

18. A compound according to claim 1 wherein the compound is of the formula:

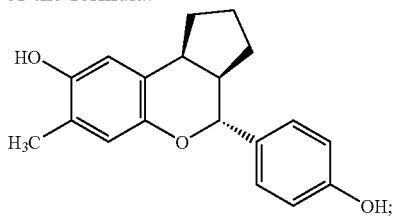

or a pharmaceutically acceptable salt thereof.

19. A compound according to claim 1 wherein the compound is of the formula:

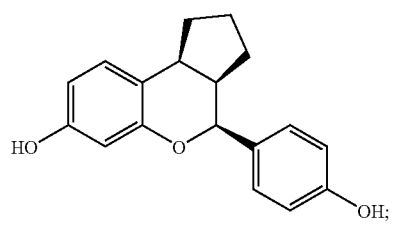

or a pharmaceutically acceptable salt thereof.

20. A compound according to claim 1 wherein the compound is of the formula:

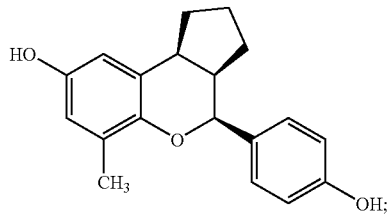

or a pharmaceutically acceptable salt thereof.

21. A compound according to claim 1 wherein the compound is of the formula:

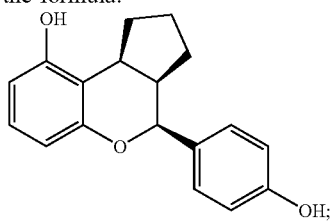

or a pharmaceutically acceptable salt thereof.

22. A compound according to claim 1 wherein the compound is of the formula:

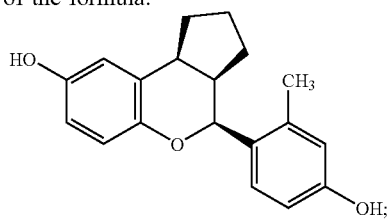

or a pharmaceutically acceptable salt thereof.

23. A compound according to claim 1 wherein the compound is of the formula:

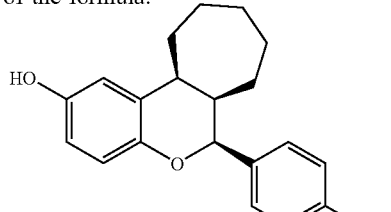

or a pharmaceutically acceptable salt thereof.

24. A compound according to claim 1 wherein the compound is of the formula:

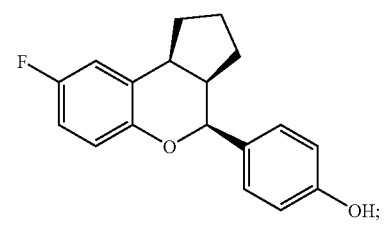

or a pharmaceutically acceptable salt thereof.

25. A compound according to claim 1 wherein the compound is of the formula:

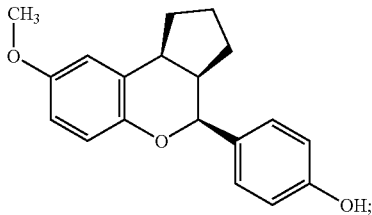

or a pharmaceutically acceptable salt thereof.

26. A compound according to claim 1 wherein the compound is of the formula:

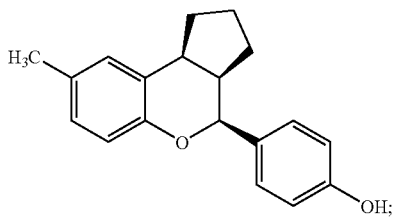

or a pharmaceutically acceptable salt thereof.

27. A compound according to claim 1 wherein the compound is of

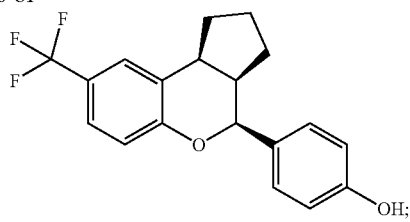

or a pharmaceutically acceptable salt thereof.

28. A compound according to claim 1 wherein the compound is of the formula:

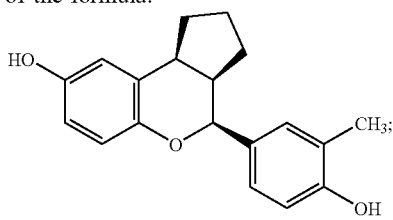

or a pharmaceutically acceptable salt thereof.

29. A compound according to claim 1 wherein the compound is of the formula:

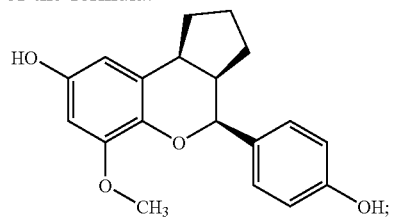

or a pharmaceutically acceptable salt thereof.

30. A compound according to claim 1 wherein the compound is of the formula:

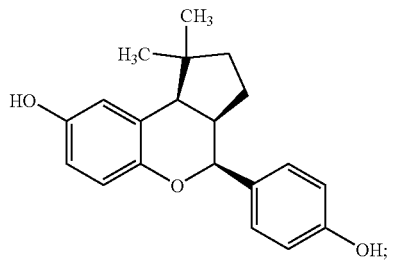

or a pharmaceutically acceptable salt thereof.

31. A compound according to claim 1 wherein the compound is of the formula:

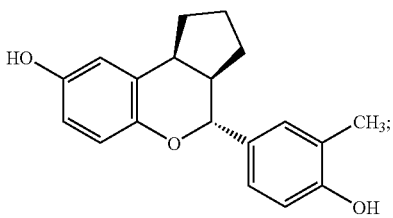

or a pharmaceutically acceptable salt thereof.

32. A compound according to claim 1 wherein the compound is of the formula:

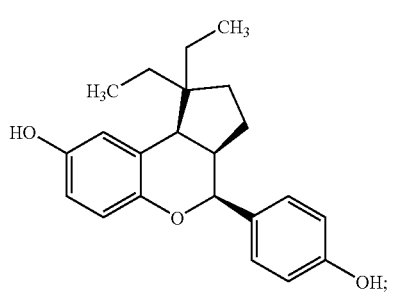

or a pharmaceutically acceptable salt thereof.

33. A compound according to claim 1 wherein the compound is of the formula:

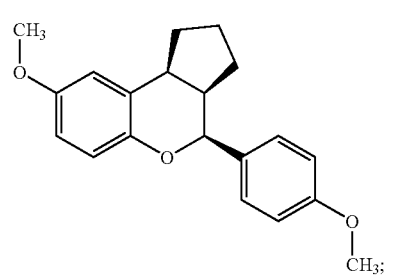

or a pharmaceutically acceptable salt thereof.

34. A compound according to claim 1 wherein the compound is of the formula:

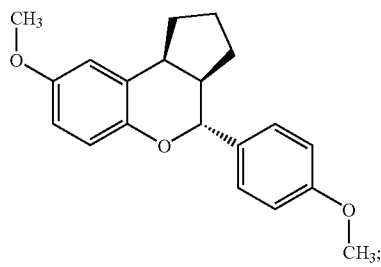

or a pharmaceutically acceptable salt thereof.

35. A compound of formula IV

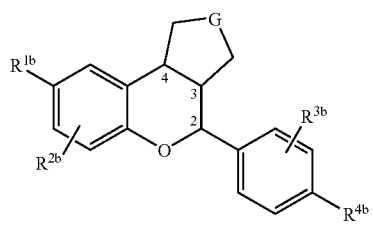

(IV)

wherein
- $R^{1b}$ is amido or hydroxy;
- $R^{2b}$ is —H, or $C_1$–$C_6$alkyl;
- $R^{3b}$ is —H or $C_1$–$C_6$ alkyl;
- $R^{4b}$ is amido or hydroxy; and
- G is —$CH_2$—, —$CH_2CH_2$—, —$CH_2CH_2CH_2$—;

or a pharmaceutically acceptable salt thereof.

36. A compound according to claim 35 wherein the compound is of the formula:

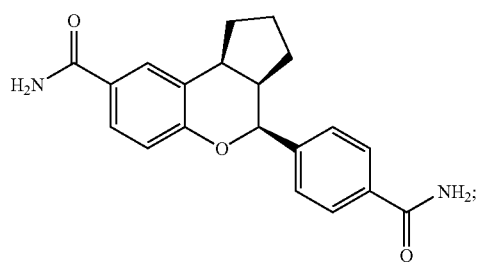

or a pharmaceutically acceptable salt thereof.

37. A compound according to claim 35 wherein the compound is of the formula:

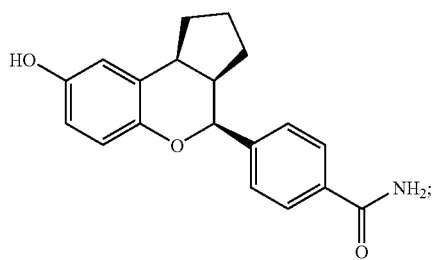

or a pharmaceutically acceptable salt thereof.

38. A compound according to claim 35 wherein the compound is of the formula:

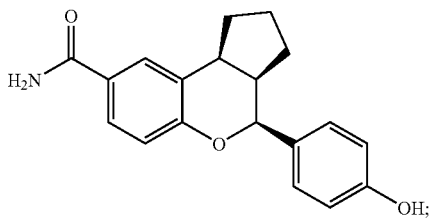

or a pharmaceutically acceptable salt thereof.

39. A compound according to claim 1 wherein the compound is of the formula:

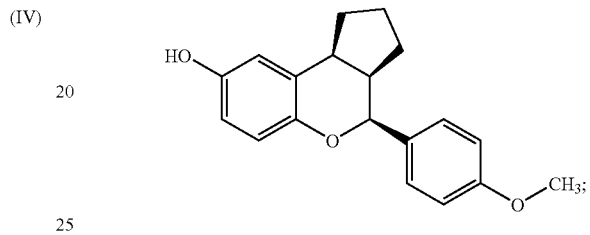

or a pharmaceutically acceptable salt thereof.

40. A compound according to claim 1 wherein the compound is of the formula:

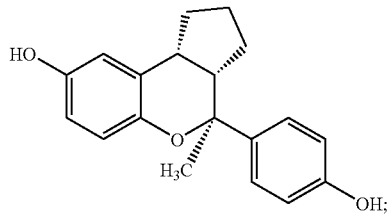

or a pharmaceutically acceptable salt thereof.

41. A compound according to claim 1 wherein the compound is of the formula:

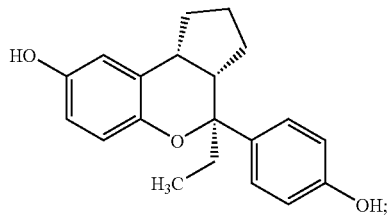

or a pharmaceutically acceptable salt thereof.

42. A compound according to claim 1 wherein the compound is of the formula:

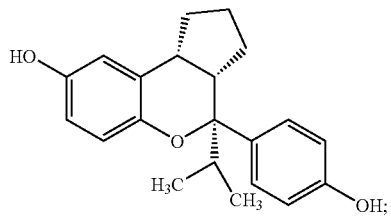

or a pharmaceutically acceptable salt thereof.

43. A compound selected from the group consisting of:
a) (±)-2-(4-hydroxyphenyl)-6-hydroxy-cyclopentyl[c]3,4-dihydro-2H-1-benzopyran
b) (±)-2-(4-hydroxyphenyl)-6-trifluoromethyl-cyclopentyl[c]3,4-dihydro-2H-1-benzopyran
c) (±)-2-(4-hydroxyphenyl)-6-methyl-cyclopentyl[c]3,4-dihydro-2H-1-benzopyran
d) (±)-2-(4-hydroxyphenyl)-6-fluoro-cyclopentyl[c]3,4-dihydro-2H-1-benzopyran
e) (±)-2-(4-hydroxyphenyl)-5-hydroxy-cyclopentyl[c]3,4-dihydro-2H-1-benzopyran
f) (±)-2-(4-hydroxyphenyl)-7-hydroxy-cyclopentyl[c]3,4-dihydro-2H-1-benzopyran
g) (±)-2-(4-hydroxyphenyl)-6-hydroxy-8-methyl-cyclopentyl[c]3,4-dihydro-2H-1-benzopyran
h) (±)-2-(4-hydroxyphenyl)-6-hydroxy-cycloheptyl[c]3,4-dihydro-2H-1-benzopyran
i) (±)-2-(4-hydroxyphenyl)-6-hydroxy-8-methoxy-cyclopentyl[c]3,4-dihydro-2H-1-benzopyran
j) (±)-2-(4-hydroxyphenyl)-6-hydroxy-11,11-dimethyl-cyclopentyl[c]3,4-dihydro-2H-1-benzopyran,
k) (±)-2-(4-hydroxyphenyl)-6-hydroxy-11,11-diethyl-cyclopentyl[c]3,4-dihydro-2H-1-benzopyran,
l) (±)-2-(4-hydroxyphenyl)-6-methoxy-cyclopentyl[c]3,4-dihydro-2H-1-benzopyran,
m) (±)-2-(4-hydroxy-3-methylphenyl)-6-hydroxy-cyclopentyl[c]3,4-dihydro-2H-1-benzopyran,
n) (±)-2-(2-methyl-4-hydroxyphenyl)-6-hydroxy-cyclopentyl[c]3,4-dihydro-2H-1-benzopyran,
o) (±)-2-(4-hydroxyphenyl)-cyclopentyl[c]3,4-dihydro-2H-1-benzopyran,
p) (±)-2-(4-hydroxyphenyl)-6-hydroxy-7-methyl-cyclopentyl[c]3,4-dihydro-2H-1-benzopyran,
q) (±)-2-(4-hydroxyphenyl)-6-hydroxy-cyclohexyl[c]3,4-dihydro-2H-1-benzopyran,
r) (±)-2-(4-methoxyphenyl)-6-methoxy-cyclopentyl[c]3,4-dihydro-2H-1-benzopyran,
s) (±)-2-(4-aminocarbonylphenyl)-6-aminocarbonyl-cyclopentyl[c]3,4-dihydro-2H-1-benzopyran,
t) (±)-2-(4-aminocarbonylphenyl)-6-hydroxy-cyclopentyl[c]3,4-dihydro-2H-1-benzopyran,
u) (±)-2-(4-hydroxyphenyl)-6-aminocarbonyl-cyclopentyl[c]3,4-dihydro-2H-1-benzopyran,
v) (±)-2-(4-methoxyphenyl)-6-hydroxy-cyclopentyl[c]3,4-dihydro-2H-1-benzopyran,
w) (±)-2-methyl-2-(4-hydroxyphenyl)-6-hydroxy-cyclopentyl[c]3,4-dihydro-2H-1-benzopyran, and
x) (±)-2-ethyl-2-(4-hydroxyphenyl)-6-hydroxy-cyclopentyl[c]3,4-dihydro-2H-1-benzopyran,
y) (±)-2-(1-methylethyl)-2-(4-hydroxyphenyl)-6-hydroxy-cyclopentyl[c]3,4-dihydro-2H-1-benzopyran; or
a pharmaceutically acceptable salt thereof.

44. A pharmaceutical composition comprising a compound according to claim 1 and a pharmaceutically acceptable carrier.

45. A pharmaceutical composition comprising a compound according to claim 35 and a pharmaceutically acceptable carrier.

46. A method of treating benign prostatic hyperplasia in a patient in need thereof comprising administering to said patient a therapeutically effective amount of a compound of claim 1.

47. The method of claim 46 wherein said patient is human.

48. A method of treating benign prostatic hyperplasia in a patient in need thereof comprising administering to said patient a therapeutically effective amount of a compound of claim 35.

49. The method of claim 48 wherein said patient is human.

50. A method of treating benign prostatic hyperplasia in a patient in need thereof comprising administering to said patient a therapeutically effective amount of a compound of claim 43.

51. The method of claim 50 wherein said patient is human.

52. A method of treating prostatic cancer in a patient in need thereof comprising administering to said patient a therapeutically effective amount of a compound of claim 1.

* * * * *

UNITED STATES PATENT AND TRADEMARK OFFICE
CERTIFICATE OF CORRECTION

PATENT NO.       : 7,217,734 B2
APPLICATION NO.  : 10/493092
DATED            : May 15, 2007
INVENTOR(S)      : Jeffrey Alan Dodge It is certified that error appears in the above-identified patent and that said Letters Patent is hereby corrected as shown below:

In each of Examples 1 through 27, at each of the identified locations listed below, please delete "$(^+)$" and replace with --($\pm$)--:
column 53, line 41
column 54, line 46
column 55, line 15
column 55, line 50
column 56, line 17
column 56, line 52
column 57, line 18
column 57, line 51
column 58, line 29
column 59, line 3
column 59, line 42
column 60, line 14
column 60, line 50
column 61, line 24
column 61, line 51
column 65, line 37
column 68, line 20
column 68, line 38
column 69, line 16
column 69, line 35
column 72, line 3
column 72, line 33
column 72, line 51
column 74, line 3
column 74, line 42
column 75, line 46; and
column 76, line 34.

In column 54, line 12, please delete "(2R,3R,4R)" and replace with --(2R,3S,4R)--.

In column 54, line 14, please delete "(2S,3S,4S)" and replace with --(2S,3R,4S)--.

In column 54, line 41, please delete "(S,S,S)" and replace with --(S,R,S)--.

In column 54, line 41, please delete "(R,R,R)" and replace with --(R,S,R)--.

UNITED STATES PATENT AND TRADEMARK OFFICE
CERTIFICATE OF CORRECTION

PATENT NO. : 7,217,734 B2
APPLICATION NO. : 10/493092
DATED : May 15, 2007
INVENTOR(S) : Jeffrey Alan Dodge It is certified that error appears in the above-identified patent and that said Letters Patent is hereby corrected as shown below:

In column 89, line 29, after the words "is of" add the words --the formula:--.

Signed and Sealed this

Seventeenth Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,217,734 B2 Page 1 of 1
APPLICATION NO. : 10/493092
DATED : May 15, 2007
INVENTOR(S) : Jeffrey Alan Dodge It is certified that error appears in the above-identified patent and that said Letters Patent is hereby corrected as shown below:

In each of Examples 28, 29 and 30, at each of the identified locations listed below, please delete "(+)" and replace with --(±)--:

Column 77, line 26
Column 78, line 15; and
Column 79, line 3

Signed and Sealed this

Eighteenth Day of March, 2008

JON W. DUDAS
*Director of the United States Patent and Trademark Office*